United States Patent
Marinkovich et al.

(10) Patent No.: US 9,351,914 B2
(45) Date of Patent: May 31, 2016

(54) METHODS FOR MODULATING HAIR GROWTH USING TRUNCATED LAMININ-511

(71) Applicant: The Board of Trustees of the Leland Stanford Junior University, Palo Alto, CA (US)

(72) Inventors: M. Peter Marinkovich, Redwood City, CA (US); Jing Gao, Mountain View, CA (US); Xiaoyu Xu, Foster City, CA (US); Jayakumar Rajadas, Cupertino, CA (US)

(73) Assignee: THE BOARD OF TRUSTEES OF THE LELAND STANFORD JUNIOR UNIVERSITY, Palo Alto, CA (US)

( * ) Notice: Subject to any disclaimer, the term of this patent is extended or adjusted under 35 U.S.C. 154(b) by 56 days.

(21) Appl. No.: 14/385,138

(22) PCT Filed: Mar. 15, 2013

(86) PCT No.: PCT/US2013/032716
§ 371 (c)(1),
(2) Date: Sep. 12, 2014

(87) PCT Pub. No.: WO2013/148377
PCT Pub. Date: Oct. 3, 2013

(65) Prior Publication Data
US 2015/0025452 A1    Jan. 22, 2015

Related U.S. Application Data

(60) Provisional application No. 61/615,330, filed on Mar. 25, 2012.

(51) Int. Cl.
| | |
|---|---|
| *A61K 38/16* | (2006.01) |
| *A61K 8/64* | (2006.01) |
| *A61Q 7/00* | (2006.01) |
| *A61K 8/02* | (2006.01) |
| *A61K 8/60* | (2006.01) |
| *A61M 5/00* | (2006.01) |
| *A61M 37/00* | (2006.01) |
| *A61Q 7/02* | (2006.01) |

(52) U.S. Cl.
CPC .............. *A61K 8/64* (2013.01); *A61K 8/0204* (2013.01); *A61K 8/606* (2013.01); *A61M 5/002* (2013.01); *A61M 37/0015* (2013.01); *A61Q 7/00* (2013.01); *A61Q 7/02* (2013.01); *A61K 2800/91* (2013.01); *A61M 2037/0023* (2013.01); *A61M 2037/0061* (2013.01)

(58) Field of Classification Search
CPC ............................ C12N 2533/52; A61K 38/16
See application file for complete search history.

(56) References Cited

U.S. PATENT DOCUMENTS

| | | |
|---|---|---|
| 2010/0203635 A1 | 8/2010 | Tryggvason et al. |
| 2010/0211325 A1 | 8/2010 | Anstee et al. |
| 2011/0263724 A1 | 10/2011 | Gurtner et al. |

FOREIGN PATENT DOCUMENTS

WO    2012065065 A1    5/2012

OTHER PUBLICATIONS

Absolique Hair Health Clinic. (2011; on the web at trichologistbrisbane.com.au.*
NanoThick, 2009. on the web at nonothick.com/nanogen_scalp_roller.htm.*
Iwai North America Inc, 2016. on the web at iwaichem.com/Laminin-511-E8-fragments.html.*
BioLamina, 2016. on the web at biolaminia.com/ln-511.*
Gao et al. 2009; Laminin-511 is an epithelial message promoting dermal papilla development and function during early hair morphogenesis. Genes & Development 22:2111-2124.*
Imanishi et al. 2010; Laminin-511, inducer of hair growth, is down-regulated and its suppressor in hair growth, laminin-332 upregulated in chemotherapy-induced alopecia. J. Dermatol. Sci. 58(1): 43-54.*
HairLossHelp, 2010. on the web at hairlosshelp.com/forums/messageview.cfm?catid=10&threadid=88358.*
HairLossTalk, 2007. on the web at hairlosstalk.com/interact/showthread.php/37247-laminin-511-qupt-available.*
Ita, 2015. Transdermal delivery of drugs with microneedles—potential and challenges. Pharmaceutics 7: 90-105.*

* cited by examiner

*Primary Examiner* — Karen Cochrane Carlson
(74) *Attorney, Agent, or Firm* — Stanford University; Andrea Blecken

(57) ABSTRACT

Disclosed are methods for the use of a truncated, recombinant laminin-511 for modifying hair growth as well as delivery devices, kits and methods for topically administering truncated, recombinant laminin-511. Furthermore disclosed are delivery devices, kits and methods using modulators of full-length laminin-511 expression or function to decrease hair growth in areas of unwanted hair growth.

21 Claims, 4 Drawing Sheets

SEQUENCE LISTING

<160> NUMBER OF SEQ ID NOS: 8

<210> SEQ ID NO 1
<211> LENGTH: 1162
<212> TYPE: PRT
<213> ORGANISM: Homo sapiens

<220> FEATURE:
<221> NAME/KEY: MISC_FEATURE
<222> LOCATION: (1)..(1162)

<400> SEQUENCE: 1

```
Ala Ala Glu Asp Ala Ala Gly Gln Ala Leu Gln Gln Ala Asp His Thr
1               5                   10                  15

Trp Ala Thr Val Val Arg Gln Gly Leu Val Asp Arg Ala Gln Gln Leu
            20                  25                  30

Leu Ala Asn Ser Thr Ala Leu Glu Ala Met Leu Gln Glu Gln Gln
        35                  40                  45

Arg Leu Gly Leu Val Trp Ala Ala Leu Gln Gly Ala Arg Thr Gln Leu
50                  55                  60

Arg Asp Val Arg Ala Lys Lys Asp Gln Leu Glu Ala His Ile Gln Ala
65                  70                  75                  80

Ala Gln Ala Met Leu Ala Met Asp Thr Asp Glu Thr Ser Lys Lys Ile
                85                  90                  95

Ala His Ala Lys Ala Val Ala Ala Glu Ala Gln Asp Thr Ala Thr Arg
            100                 105                 110

Val Gln Ser Gln Leu Gln Ala Met Gln Glu Asn Val Glu Arg Trp Gln
        115                 120                 125

Gly Gln Tyr Glu Gly Leu Arg Gly Gln Asp Leu Gly Gln Ala Val Leu
130                 135                 140

Asp Ala Gly His Ser Val Ser Thr Leu Glu Lys Thr Leu Pro Gln Leu
145                 150                 155                 160

Leu Ala Lys Leu Ser Ile Leu Glu Asn Arg Gly Val His Asn Ala Ser
                165                 170                 175

Leu Ala Leu Ser Ala Ser Ile Gly Arg Val Arg Glu Leu Ile Ala Gln
            180                 185                 190

Ala Arg Gly Ala Ala Ser Lys Val Lys Val Pro Met Lys Phe Asn Gly
        195                 200                 205

Arg Ser Gly Val Gln Leu Arg Thr Pro Arg Asp Leu Ala Asp Leu Ala
210                 215                 220

Ala Tyr Thr Ala Leu Lys Phe Tyr Leu Gln Gly Pro Glu Pro Glu Pro
225                 230                 235                 240

Gly Gln Gly Thr Glu Asp Arg Phe Val Met Tyr Met Gly Ser Arg Gln
                245                 250                 255

Ala Thr Gly Asp Tyr Met Gly Val Ser Leu Arg Asp Lys Lys Val His
            260                 265                 270

Trp Val Tyr Gln Leu Gly Glu Ala Gly Pro Ala Val Leu Ser Ile Asp
        275                 280                 285

Glu Asp Ile Gly Glu Gln Phe Ala Ala Val Ser Leu Asp Arg Thr Leu
290                 295                 300

Gln Phe Gly His Met Ser Val Thr Val Glu Arg Gln Met Ile Gln Glu
305                 310                 315                 320

Thr Lys Gly Asp Thr Val Ala Pro Gly Ala Glu Gly Leu Leu Asn Leu
                325                 330                 335

Arg Pro Asp Asp Phe Val Phe Tyr Val Gly Gly Tyr Pro Ser Thr Phe
            340                 345                 350

Thr Pro Pro Pro Leu Leu Arg Phe Pro Gly Tyr Arg Gly Cys Ile Glu
        355                 360                 365

Met Asp Thr Leu Asn Glu Glu Val Val Ser Leu Tyr Asn Phe Glu Arg
370                 375                 380

Thr Phe Gln Leu Asp Thr Ala Val Asp Arg Pro Cys Ala Arg Ser Lys
```

-continued

```
            385                 390                 395                 400
Ser Thr Gly Asp Pro Trp Leu Thr Asp Gly Ser Tyr Leu Asp Gly Thr
                    405                 410                 415

Gly Phe Ala Arg Ile Ser Phe Asp Ser Gln Ile Ser Thr Thr Lys Arg
                    420                 425                 430

Phe Glu Gln Glu Leu Arg Leu Val Ser Tyr Ser Gly Val Leu Phe Phe
                    435                 440                 445

Leu Lys Gln Gln Ser Gln Phe Leu Cys Leu Ala Val Gln Glu Gly Ser
            450                 455                 460

Leu Val Leu Leu Tyr Asp Phe Gly Ala Gly Leu Lys Lys Ala Val Pro
465                 470                 475                 480

Leu Gln Pro Pro Pro Leu Thr Ser Ala Ser Lys Ala Ile Gln Val
                    485                 490                 495

Phe Leu Leu Gly Gly Ser Arg Lys Arg Val Leu Val Arg Val Glu Arg
                    500                 505                 510

Ala Thr Val Tyr Ser Val Glu Gln Asp Asn Asp Leu Glu Leu Ala Asp
                    515                 520                 525

Ala Tyr Tyr Leu Gly Gly Val Pro Pro Asp Gln Leu Pro Pro Ser Leu
            530                 535                 540

Arg Arg Leu Phe Pro Thr Gly Gly Ser Val Arg Gly Cys Val Lys Gly
545                 550                 555                 560

Ile Lys Ala Leu Gly Lys Tyr Val Asp Leu Lys Arg Leu Asn Thr Thr
                    565                 570                 575

Gly Val Ser Ala Gly Cys Thr Ala Asp Leu Leu Val Gly Arg Ala Met
                    580                 585                 590

Thr Phe His Gly His Gly Phe Leu Arg Leu Ala Leu Ser Asn Val Ala
                    595                 600                 605

Pro Leu Thr Gly Asn Val Tyr Ser Gly Phe Gly Phe His Ser Ala Gln
            610                 615                 620

Asp Ser Ala Leu Leu Tyr Tyr Arg Ala Ser Pro Asp Gly Leu Cys Gln
625                 630                 635                 640

Val Ser Leu Gln Gln Gly Arg Val Ser Leu Gln Leu Leu Arg Thr Glu
                    645                 650                 655

Val Lys Thr Gln Ala Gly Phe Ala Asp Gly Ala Pro His Tyr Val Ala
                    660                 665                 670

Phe Tyr Ser Asn Ala Thr Gly Val Trp Leu Tyr Val Asp Asp Gln Leu
                    675                 680                 685

Gln Gln Met Lys Pro His Arg Gly Pro Pro Glu Leu Gln Pro Gln
            690                 695                 700

Pro Glu Gly Pro Pro Arg Leu Leu Gly Gly Leu Pro Glu Ser Gly
705                 710                 715                 720

Thr Ile Tyr Asn Phe Ser Gly Cys Ile Ser Asn Val Phe Val Gln Arg
                    725                 730                 735

Leu Leu Gly Pro Gln Arg Val Phe Asp Leu Gln Gln Asn Leu Gly Ser
                    740                 745                 750

Val Asn Val Ser Thr Gly Cys Ala Pro Ala Leu Gln Ala Gln Thr Pro
            755                 760                 765

Gly Leu Gly Pro Arg Gly Leu Gln Ala Thr Ala Arg Lys Ala Ser Arg
            770                 775                 780

Arg Ser Arg Gln Pro Ala Arg His Pro Ala Cys Met Leu Pro Pro His
785                 790                 795                 800

Leu Arg Thr Thr Arg Asp Ser Tyr Gln Phe Gly Gly Ser Leu Ser Ser
                    805                 810                 815
```

His Leu Glu Phe Val Gly Ile Leu Ala Arg His Arg Asn Trp Pro Ser
                820                 825                 830

Leu Ser Met His Val Leu Pro Arg Ser Ser Arg Gly Leu Leu Phe
            835                 840                 845

Thr Ala Arg Leu Arg Pro Gly Ser Pro Ser Leu Ala Leu Phe Leu Ser
850                 855                 860

Asn Gly His Phe Val Ala Gln Met Glu Gly Leu Gly Thr Arg Leu Arg
865                 870                 875                 880

Ala Gln Ser Arg Gln Arg Ser Arg Pro Gly Arg Trp His Lys Val Ser
                885                 890                 895

Val Arg Trp Glu Lys Asn Arg Ile Leu Leu Val Thr Asp Gly Ala Arg
            900                 905                 910

Ala Trp Ser Gln Glu Gly Pro His Arg Gln His Gln Gly Ala Glu His
        915                 920                 925

Pro Gln Pro His Thr Leu Phe Val Gly Gly Leu Pro Ala Ser Ser His
    930                 935                 940

Ser Ser Lys Leu Pro Val Thr Val Gly Phe Ser Gly Cys Val Lys Arg
945                 950                 955                 960

Leu Arg Leu His Gly Arg Pro Leu Gly Ala Pro Thr Arg Met Ala Gly
                965                 970                 975

Val Thr Pro Cys Ile Leu Gly Pro Leu Glu Ala Gly Leu Phe Phe Pro
            980                 985                 990

Gly Ser Gly Gly Val Ile Thr Leu Asp Leu Pro Gly Ala Thr Leu Pro
        995                 1000                1005

Asp Val Gly Leu Glu Leu Glu Val Arg Pro Leu Ala Val Thr Gly
    1010                1015                1020

Leu Ile Phe His Leu Gly Gln Ala Arg Thr Pro Pro Tyr Leu Gln
    1025                1030                1035

Leu Gln Val Thr Glu Lys Gln Val Leu Leu Arg Ala Asp Asp Gly
    1040                1045                1050

Ala Gly Glu Phe Ser Thr Ser Val Thr Arg Pro Ser Val Leu Cys
    1055                1060                1065

Asp Gly Gln Trp His Arg Leu Ala Val Met Lys Ser Gly Asn Val
    1070                1075                1080

Leu Arg Leu Glu Val Asp Ala Gln Ser Asn His Thr Val Gly Pro
    1085                1090                1095

Leu Leu Ala Ala Ala Ala Gly Ala Pro Ala Pro Leu Tyr Leu Gly
    1100                1105                1110

Gly Leu Pro Glu Pro Met Ala Val Gln Pro Trp Pro Pro Ala Tyr
    1115                1120                1125

Cys Gly Cys Met Arg Arg Leu Ala Val Asn Arg Ser Pro Val Ala
    1130                1135                1140

Met Thr Arg Ser Val Glu Val His Gly Ala Val Gly Ala Ser Gly
    1145                1150                1155

Cys Pro Ala Ala
    1160

<210> SEQ ID NO 2
<211> LENGTH: 226
<212> TYPE: PRT
<213> ORGANISM: homo sapiens
<220> FEATURE:
<221> NAME/KEY: MISC_FEATURE
<222> LOCATION: (1)..(226)

```
<400> SEQUENCE: 2

Leu Gln His Ser Ala Ala Asp Ile Ala Arg Ala Glu Met Leu Leu Glu
1               5                   10                  15

Glu Ala Lys Arg Ala Ser Lys Ser Ala Thr Asp Val Lys Val Thr Ala
            20                  25                  30

Asp Met Val Lys Glu Ala Leu Glu Ala Glu Lys Ala Gln Val Ala
        35                  40                  45

Ala Glu Lys Ala Ile Lys Gln Ala Asp Glu Asp Ile Gln Gly Thr Gln
    50                  55                  60

Asn Leu Leu Thr Ser Ile Glu Ser Glu Thr Ala Ala Ser Glu Glu Thr
65                  70                  75                  80

Leu Phe Asn Ala Ser Gln Arg Ile Ser Glu Leu Glu Arg Asn Val Glu
                85                  90                  95

Glu Leu Lys Arg Lys Ala Ala Gln Asn Ser Gly Glu Ala Glu Tyr Ile
            100                 105                 110

Glu Lys Val Val Tyr Thr Val Lys Gln Ser Ala Glu Asp Val Lys Lys
        115                 120                 125

Thr Leu Asp Gly Glu Leu Asp Glu Lys Tyr Lys Lys Val Glu Asn Leu
    130                 135                 140

Ile Ala Lys Lys Thr Glu Glu Ser Ala Asp Ala Arg Arg Lys Ala Glu
145                 150                 155                 160

Met Leu Gln Asn Glu Ala Lys Thr Leu Leu Ala Gln Ala Asn Ser Lys
                165                 170                 175

Leu Gln Leu Leu Lys Asp Leu Glu Arg Lys Tyr Glu Asp Asn Gln Arg
            180                 185                 190

Tyr Leu Glu Asp Lys Ala Gln Glu Leu Ala Arg Leu Glu Gly Glu Val
        195                 200                 205

Arg Ser Leu Leu Lys Asp Ile Ser Gln Lys Val Ala Val Tyr Ser Thr
    210                 215                 220

Cys Leu
225

<210> SEQ ID NO 3
<211> LENGTH: 246
<212> TYPE: PRT
<213> ORGANISM: homo sapiens
<220> FEATURE:
<221> NAME/KEY: MISC_FEATURE
<222> LOCATION: (1)..(246)

<400> SEQUENCE: 3

Asn Asp Ile Leu Asn Asn Leu Lys Asp Phe Asp Arg Arg Val Asn Asp
1               5                   10                  15

Asn Lys Thr Ala Ala Glu Glu Ala Leu Arg Lys Ile Pro Ala Ile Asn
            20                  25                  30

Gln Thr Ile Thr Glu Ala Asn Glu Lys Thr Arg Glu Ala Gln Gln Ala
        35                  40                  45

Leu Gly Ser Ala Ala Ala Asp Ala Thr Glu Ala Lys Asn Lys Ala His
    50                  55                  60

Glu Ala Glu Arg Ile Ala Ser Ala Val Gln Lys Asn Ala Thr Ser Thr
65                  70                  75                  80

Lys Ala Glu Ala Glu Arg Thr Phe Ala Glu Val Thr Asp Leu Asp Asn
                85                  90                  95

Glu Val Asn Asn Met Leu Lys Gln Leu Gln Ala Glu Lys Glu Leu
            100                 105                 110
```

Lys Arg Lys Gln Asp Asp Ala Asp Gln Asp Met Met Ala Gly Met
            115                 120                 125

Ala Ser Gln Ala Ala Gln Glu Ala Glu Ile Asn Ala Arg Lys Ala Lys
        130                 135                 140

Asn Ser Val Thr Ser Leu Leu Ser Ile Ile Asn Asp Leu Leu Glu Gln
145                 150                 155                 160

Leu Gly Gln Leu Asp Thr Val Asp Leu Asn Lys Leu Asn Glu Ile Glu
                165                 170                 175

Gly Thr Leu Asn Lys Ala Lys Asp Glu Met Lys Val Ser Asp Leu Asp
            180                 185                 190

Arg Lys Val Ser Asp Leu Glu Asn Glu Ala Lys Gln Glu Ala Ala
        195                 200                 205

Ile Met Asp Tyr Asn Arg Asp Ile Glu Glu Ile Met Lys Asp Ile Arg
    210                 215                 220

Asn Leu Glu Asp Ile Arg Lys Thr Leu Pro Ser Gly Cys Phe Asn Thr
225                 230                 235                 240

Pro Ser Ile Glu Lys Pro
                245

<210> SEQ ID NO 4
<211> LENGTH: 790
<212> TYPE: PRT
<213> ORGANISM: homo sapiens
<220> FEATURE:
<221> NAME/KEY: MISC_FEATURE
<222> LOCATION: (1)..(790)

<400> SEQUENCE: 4

Ala Ala Glu Asp Ala Ala Gly Gln Ala Leu Gln Gln Ala Asp His Thr
1               5                   10                  15

Trp Ala Thr Val Val Arg Gln Gly Leu Val Asp Arg Ala Gln Gln Leu
                20                  25                  30

Leu Ala Asn Ser Thr Ala Leu Glu Glu Ala Met Leu Gln Gln Gln
            35                  40                  45

Arg Leu Gly Leu Val Trp Ala Ala Leu Gln Gly Ala Arg Thr Gln Leu
    50                  55                  60

Arg Asp Val Arg Ala Lys Lys Asp Gln Leu Glu Ala His Ile Gln Ala
65                  70                  75                  80

Ala Gln Ala Met Leu Ala Met Asp Thr Asp Glu Thr Ser Lys Lys Ile
                85                  90                  95

Ala His Ala Lys Ala Val Ala Ala Glu Ala Gln Asp Thr Ala Thr Arg
            100                 105                 110

Val Gln Ser Gln Leu Gln Ala Met Gln Glu Asn Val Glu Arg Trp Gln
    115                 120                 125

Gly Gln Tyr Glu Gly Leu Arg Gly Gln Asp Leu Gly Gln Ala Val Leu
130                 135                 140

Asp Ala Gly His Ser Val Ser Thr Leu Glu Lys Thr Leu Pro Gln Leu
145                 150                 155                 160

Leu Ala Lys Leu Ser Ile Leu Glu Asn Arg Gly Val His Asn Ala Ser
                165                 170                 175

Leu Ala Leu Ser Ala Ser Ile Gly Arg Val Arg Glu Leu Ile Ala Gln
            180                 185                 190

Ala Arg Gly Ala Ala Ser Lys Val Lys Val Pro Met Lys Phe Asn Gly
    195                 200                 205

Arg Ser Gly Val Gln Leu Arg Thr Pro Arg Asp Leu Ala Asp Leu Ala
210                 215                 220

```
Ala Tyr Thr Ala Leu Lys Phe Tyr Leu Gln Gly Pro Glu Pro Glu Pro
225                 230                 235                 240

Gly Gln Gly Thr Glu Asp Arg Phe Val Met Tyr Met Gly Ser Arg Gln
            245                 250                 255

Ala Thr Gly Asp Tyr Met Gly Val Ser Leu Arg Asp Lys Lys Val His
            260                 265                 270

Trp Val Tyr Gln Leu Gly Glu Ala Gly Pro Ala Val Leu Ser Ile Asp
            275                 280                 285

Glu Asp Ile Gly Glu Gln Phe Ala Ala Val Ser Leu Asp Arg Thr Leu
290                 295                 300

Gln Phe Gly His Met Ser Val Thr Val Glu Arg Gln Met Ile Gln Glu
305                 310                 315                 320

Thr Lys Gly Asp Thr Val Ala Pro Gly Ala Glu Gly Leu Leu Asn Leu
                325                 330                 335

Arg Pro Asp Asp Phe Val Phe Tyr Val Gly Gly Tyr Pro Ser Thr Phe
                340                 345                 350

Thr Pro Pro Pro Leu Leu Arg Phe Pro Gly Tyr Arg Gly Cys Ile Glu
            355                 360                 365

Met Asp Thr Leu Asn Glu Glu Val Val Ser Leu Tyr Asn Phe Glu Arg
370                 375                 380

Thr Phe Gln Leu Asp Thr Ala Val Asp Arg Pro Cys Ala Arg Ser Lys
385                 390                 395                 400

Ser Thr Gly Asp Pro Trp Leu Thr Asp Gly Ser Tyr Leu Asp Gly Thr
                405                 410                 415

Gly Phe Ala Arg Ile Ser Phe Asp Ser Gln Ile Ser Thr Thr Lys Arg
                420                 425                 430

Phe Glu Gln Glu Leu Arg Leu Val Ser Tyr Ser Gly Val Leu Phe Phe
            435                 440                 445

Leu Lys Gln Gln Ser Gln Phe Leu Cys Leu Ala Val Gln Glu Gly Ser
    450                 455                 460

Leu Val Leu Leu Tyr Asp Phe Gly Ala Gly Leu Lys Lys Ala Val Pro
465                 470                 475                 480

Leu Gln Pro Pro Pro Leu Thr Ser Ala Ser Lys Ala Ile Gln Val
                485                 490                 495

Phe Leu Leu Gly Gly Ser Arg Lys Arg Val Leu Val Arg Val Glu Arg
            500                 505                 510

Ala Thr Val Tyr Ser Val Glu Gln Asp Asn Asp Leu Glu Leu Ala Asp
            515                 520                 525

Ala Tyr Tyr Leu Gly Gly Val Pro Pro Asp Gln Leu Pro Pro Ser Leu
            530                 535                 540

Arg Arg Leu Phe Pro Thr Gly Gly Ser Val Arg Gly Cys Val Lys Gly
545                 550                 555                 560

Ile Lys Ala Leu Gly Lys Tyr Val Asp Leu Lys Arg Leu Asn Thr Thr
                565                 570                 575

Gly Val Ser Ala Gly Cys Thr Ala Asp Leu Leu Val Gly Arg Ala Met
            580                 585                 590

Thr Phe His Gly His Gly Phe Leu Arg Leu Ala Leu Ser Asn Val Ala
            595                 600                 605

Pro Leu Thr Gly Asn Val Tyr Ser Gly Phe Gly Phe His Ser Ala Gln
        610                 615                 620

Asp Ser Ala Leu Leu Tyr Tyr Arg Ala Ser Pro Asp Gly Leu Cys Gln
625                 630                 635                 640
```

```
Val Ser Leu Gln Gln Gly Arg Val Ser Leu Gln Leu Leu Arg Thr Glu
                    645                 650                 655

Val Lys Thr Gln Ala Gly Phe Ala Asp Gly Ala Pro His Tyr Val Ala
            660                 665                 670

Phe Tyr Ser Asn Ala Thr Gly Val Trp Leu Tyr Val Asp Asp Gln Leu
        675                 680                 685

Gln Gln Met Lys Pro His Arg Gly Pro Pro Glu Leu Gln Pro Gln
    690                 695                 700

Pro Glu Gly Pro Pro Arg Leu Leu Leu Gly Leu Pro Glu Ser Gly
705                 710                 715                 720

Thr Ile Tyr Asn Phe Ser Gly Cys Ile Ser Asn Val Phe Val Gln Arg
                725                 730                 735

Leu Leu Gly Pro Gln Arg Val Phe Asp Leu Gln Gln Asn Leu Gly Ser
            740                 745                 750

Val Asn Val Ser Thr Gly Cys Ala Pro Ala Leu Gln Ala Gln Thr Pro
        755                 760                 765

Gly Leu Gly Pro Arg Gly Leu Gln Ala Thr Ala Arg Lys Ala Ser Arg
    770                 775                 780

Arg Ser Arg Gln Pro Ala
785                 790

<210> SEQ ID NO 5
<211> LENGTH: 911
<212> TYPE: PRT
<213> ORGANISM: homo sapiens
<220> FEATURE:
<221> NAME/KEY: MISC_FEATURE
<222> LOCATION: (1)..(911)

<400> SEQUENCE: 5

Ala Ala Glu Asp Ala Ala Gly Gln Ala Leu Gln Gln Ala Asp His Thr
1               5                   10                  15

Trp Ala Thr Val Val Arg Gln Gly Leu Val Asp Arg Ala Gln Gln Leu
            20                  25                  30

Leu Ala Asn Ser Thr Ala Leu Glu Glu Ala Met Leu Gln Glu Gln Gln
        35                  40                  45

Arg Leu Gly Leu Val Trp Ala Ala Leu Gln Gly Ala Arg Thr Gln Leu
    50                  55                  60

Arg Asp Val Arg Ala Lys Lys Asp Gln Leu Glu Ala His Ile Gln Ala
65                  70                  75                  80

Ala Gln Ala Met Leu Ala Met Asp Thr Asp Glu Thr Ser Lys Lys Ile
                85                  90                  95

Ala His Ala Lys Ala Val Ala Ala Glu Ala Gln Asp Thr Ala Thr Arg
            100                 105                 110

Val Gln Ser Gln Leu Gln Ala Met Gln Glu Asn Val Glu Arg Trp Gln
        115                 120                 125

Gly Gln Tyr Glu Gly Leu Arg Gly Gln Asp Leu Gly Gln Ala Val Leu
    130                 135                 140

Asp Ala Gly His Ser Val Ser Thr Leu Glu Lys Thr Leu Pro Gln Leu
145                 150                 155                 160

Leu Ala Lys Leu Ser Ile Leu Glu Asn Arg Gly Val His Asn Ala Ser
                165                 170                 175

Leu Ala Leu Ser Ala Ser Ile Gly Arg Val Arg Glu Leu Ile Ala Gln
            180                 185                 190

Ala Arg Gly Ala Ala Ser Lys Val Lys Val Pro Met Lys Phe Asn Gly
        195                 200                 205
```

Arg Ser Gly Val Gln Leu Arg Thr Pro Arg Asp Leu Ala Asp Leu Ala
    210                 215                 220

Ala Tyr Thr Ala Leu Lys Phe Tyr Leu Gln Gly Pro Glu Pro Glu Pro
225                 230                 235                 240

Gly Gln Gly Thr Glu Asp Arg Phe Val Met Tyr Met Gly Ser Arg Gln
                245                 250                 255

Ala Thr Gly Asp Tyr Met Gly Val Ser Leu Arg Asp Lys Lys Val His
                260                 265                 270

Trp Val Tyr Gln Leu Gly Glu Ala Gly Pro Ala Val Leu Ser Ile Asp
                275                 280                 285

Glu Asp Ile Gly Glu Gln Phe Ala Ala Val Ser Leu Asp Arg Thr Leu
290                 295                 300

Gln Phe Gly His Met Ser Val Thr Val Glu Arg Gln Met Ile Gln Glu
305                 310                 315                 320

Thr Lys Gly Asp Thr Val Ala Pro Gly Ala Glu Gly Leu Leu Asn Leu
                325                 330                 335

Arg Pro Asp Asp Phe Val Phe Tyr Val Gly Gly Tyr Pro Ser Thr Phe
                340                 345                 350

Thr Pro Pro Leu Leu Arg Phe Pro Gly Tyr Arg Gly Cys Ile Glu
    355                 360                 365

Met Asp Thr Leu Asn Glu Glu Val Val Ser Leu Tyr Asn Phe Glu Arg
370                 375                 380

Thr Phe Gln Leu Asp Thr Ala Val Asp Arg Pro Cys Ala Arg Ser Lys
385                 390                 395                 400

Ser Thr Gly Asp Pro Trp Leu Thr Asp Gly Ser Tyr Leu Asp Gly Thr
                405                 410                 415

Gly Phe Ala Arg Ile Ser Phe Asp Ser Gln Ile Ser Thr Thr Lys Arg
                420                 425                 430

Phe Glu Gln Glu Leu Arg Leu Val Ser Tyr Ser Gly Val Leu Phe Phe
    435                 440                 445

Leu Lys Gln Gln Ser Gln Phe Leu Cys Leu Ala Val Gln Glu Gly Ser
    450                 455                 460

Leu Val Leu Leu Tyr Asp Phe Gly Ala Gly Leu Lys Lys Ala Val Pro
465                 470                 475                 480

Leu Gln Pro Pro Pro Leu Thr Ser Ala Ser Lys Ala Ile Gln Val
                485                 490                 495

Phe Leu Leu Gly Gly Ser Arg Lys Arg Val Leu Val Arg Val Glu Arg
                500                 505                 510

Ala Thr Val Tyr Ser Val Glu Gln Asp Asn Asp Leu Glu Leu Ala Asp
                515                 520                 525

Ala Tyr Tyr Leu Gly Gly Val Pro Pro Asp Gln Leu Pro Pro Ser Leu
    530                 535                 540

Arg Arg Leu Phe Pro Thr Gly Gly Ser Val Arg Gly Cys Val Lys Gly
545                 550                 555                 560

Ile Lys Ala Leu Gly Lys Tyr Val Asp Leu Lys Arg Leu Asn Thr Thr
                565                 570                 575

Gly Val Ser Ala Gly Cys Thr Ala Asp Leu Leu Val Gly Arg Ala Met
                580                 585                 590

Thr Phe His Gly His Gly Phe Leu Arg Leu Ala Leu Ser Asn Val Ala
    595                 600                 605

Pro Leu Thr Gly Asn Val Tyr Ser Gly Phe Gly Phe His Ser Ala Gln
    610                 615                 620

```
Asp Ser Ala Leu Leu Tyr Tyr Arg Ala Ser Pro Asp Gly Leu Cys Gln
625                 630                 635                 640

Val Ser Leu Gln Gln Gly Arg Val Ser Leu Gln Leu Leu Arg Thr Glu
            645                 650                 655

Val Lys Thr Gln Ala Gly Phe Ala Asp Gly Ala Pro His Tyr Val Ala
            660                 665                 670

Phe Tyr Ser Asn Ala Thr Gly Val Trp Leu Tyr Val Asp Asp Gln Leu
            675                 680                 685

Gln Gln Met Lys Pro His Arg Gly Pro Pro Glu Leu Gln Pro Gln
690                 695                 700

Pro Glu Gly Pro Pro Arg Leu Leu Leu Gly Leu Pro Glu Ser Gly
705                 710                 715                 720

Thr Ile Tyr Asn Phe Ser Gly Cys Ile Ser Asn Val Phe Val Gln Arg
                725                 730                 735

Leu Leu Gly Pro Gln Arg Val Phe Asp Leu Gln Gln Asn Leu Gly Ser
            740                 745                 750

Val Asn Val Ser Thr Gly Cys Ala Pro Ala Leu Gln Ala Gln Thr Pro
            755                 760                 765

Gly Leu Gly Pro Arg Gly Leu Gln Ala Thr Ala Arg Lys Ala Ser Arg
770                 775                 780

Arg Ser Arg Gln Pro Ala Arg His Pro Ala Cys Met Leu Pro Pro His
785                 790                 795                 800

Leu Arg Thr Thr Arg Asp Ser Tyr Gln Phe Gly Gly Ser Leu Ser Ser
                805                 810                 815

His Leu Glu Phe Val Gly Ile Leu Ala Arg His Arg Asn Trp Pro Ser
            820                 825                 830

Leu Ser Met His Val Leu Pro Arg Ser Ser Arg Gly Leu Leu Leu Phe
            835                 840                 845

Thr Ala Arg Leu Arg Pro Gly Ser Pro Ser Leu Ala Leu Phe Leu Ser
850                 855                 860

Asn Gly His Phe Val Ala Gln Met Glu Gly Leu Gly Thr Arg Leu Arg
865                 870                 875                 880

Ala Gln Ser Arg Gln Arg Ser Arg Pro Gly Arg Trp His Lys Val Ser
                885                 890                 895

Val Arg Trp Glu Lys Asn Arg Ile Leu Leu Val Thr Asp Gly Ala
            900                 905                 910

<210> SEQ ID NO 6
<211> LENGTH: 3695
<212> TYPE: PRT
<213> ORGANISM: homo sapiens
<220> FEATURE:
<221> NAME/KEY: MISC_FEATURE
<222> LOCATION: (1)..(3695)

<400> SEQUENCE: 6

Met Ala Lys Arg Leu Cys Ala Gly Ser Ala Leu Cys Val Arg Gly Pro
1               5                   10                  15

Arg Gly Pro Ala Pro Leu Leu Leu Val Gly Leu Ala Leu Leu Gly Ala
            20                  25                  30

Ala Arg Ala Arg Glu Glu Ala Gly Gly Phe Ser Leu His Pro Pro
        35                  40                  45

Tyr Phe Asn Leu Ala Glu Gly Ala Arg Ile Ala Ala Ser Ala Thr Cys
50                  55                  60

Gly Glu Glu Ala Pro Ala Arg Gly Ser Pro Arg Pro Thr Glu Asp Leu
65                  70                  75                  80
```

```
Tyr Cys Lys Leu Val Gly Gly Pro Val Ala Gly Gly Asp Pro Asn Gln
                 85                  90                  95

Thr Ile Arg Gly Gln Tyr Cys Asp Ile Cys Thr Ala Ala Asn Ser Asn
            100                 105                 110

Lys Ala His Pro Ala Ser Asn Ala Ile Asp Gly Thr Glu Arg Trp Trp
            115                 120                 125

Gln Ser Pro Pro Leu Ser Arg Gly Leu Glu Tyr Asn Glu Val Asn Val
    130                 135                 140

Thr Leu Asp Leu Gly Gln Val Phe His Val Ala Tyr Val Leu Ile Lys
145                 150                 155                 160

Phe Ala Asn Ser Pro Arg Pro Asp Leu Trp Val Leu Glu Arg Ser Met
                165                 170                 175

Asp Phe Gly Arg Thr Tyr Gln Pro Trp Gln Phe Phe Ala Ser Ser Lys
            180                 185                 190

Arg Asp Cys Leu Glu Arg Phe Gly Pro Gln Thr Leu Glu Arg Ile Thr
            195                 200                 205

Arg Asp Asp Ala Ala Ile Cys Thr Thr Glu Tyr Ser Arg Ile Val Pro
            210                 215                 220

Leu Glu Asn Gly Glu Ile Val Val Ser Leu Val Asn Gly Arg Pro Gly
225                 230                 235                 240

Ala Met Asn Phe Ser Tyr Ser Pro Leu Leu Arg Glu Phe Thr Lys Ala
                245                 250                 255

Thr Asn Val Arg Leu Arg Phe Leu Arg Thr Asn Thr Leu Leu Gly His
            260                 265                 270

Leu Met Gly Lys Ala Leu Arg Asp Pro Thr Val Thr Arg Arg Tyr Tyr
            275                 280                 285

Tyr Ser Ile Lys Asp Ile Ser Ile Gly Gly Arg Cys Val Cys His Gly
            290                 295                 300

His Ala Asp Ala Cys Asp Ala Lys Asp Pro Thr Asp Pro Phe Arg Leu
305                 310                 315                 320

Gln Cys Thr Cys Gln His Asn Thr Cys Gly Gly Thr Cys Asp Arg Cys
                325                 330                 335

Cys Pro Gly Phe Asn Gln Gln Pro Trp Lys Pro Ala Thr Ala Asn Ser
            340                 345                 350

Ala Asn Glu Cys Gln Ser Cys Asn Cys Tyr Gly His Ala Thr Asp Cys
            355                 360                 365

Tyr Tyr Asp Pro Glu Val Asp Arg Arg Arg Ala Ser Gln Ser Leu Asp
            370                 375                 380

Gly Thr Tyr Gln Gly Gly Gly Val Cys Ile Asp Cys Gln His His Thr
385                 390                 395                 400

Thr Gly Val Asn Cys Glu Arg Cys Leu Pro Gly Phe Tyr Arg Ser Pro
                405                 410                 415

Asn His Pro Leu Asp Ser Pro His Val Cys Arg Arg Cys Asn Cys Glu
            420                 425                 430

Ser Asp Phe Thr Asp Gly Thr Cys Glu Asp Leu Thr Gly Arg Cys Tyr
            435                 440                 445

Cys Arg Pro Asn Phe Ser Gly Glu Arg Cys Asp Val Cys Ala Glu Gly
            450                 455                 460

Phe Thr Gly Phe Pro Ser Cys Tyr Pro Thr Pro Ser Ser Ser Asn Asp
465                 470                 475                 480

Thr Arg Glu Gln Val Leu Pro Ala Gly Gln Ile Val Asn Cys Asp Cys
                485                 490                 495
```

-continued

Ser Ala Ala Gly Thr Gln Gly Asn Ala Cys Arg Lys Asp Pro Arg Val
                500                 505                 510

Gly Arg Cys Leu Cys Lys Pro Asn Phe Gln Gly Thr His Cys Glu Leu
            515                 520                 525

Cys Ala Pro Gly Phe Tyr Gly Pro Gly Cys Gln Pro Cys Gln Cys Ser
        530                 535                 540

Ser Pro Gly Val Ala Asp Asp Arg Cys Asp Pro Asp Thr Gly Gln Cys
545                 550                 555                 560

Arg Cys Arg Val Gly Phe Glu Gly Ala Thr Cys Asp Arg Cys Ala Pro
                565                 570                 575

Gly Tyr Phe His Phe Pro Leu Cys Gln Leu Cys Gly Cys Ser Pro Ala
            580                 585                 590

Gly Thr Leu Pro Glu Gly Cys Asp Glu Ala Gly Arg Cys Leu Cys Gln
        595                 600                 605

Pro Glu Phe Ala Gly Pro His Cys Asp Arg Cys Arg Pro Gly Tyr His
610                 615                 620

Gly Phe Pro Asn Cys Gln Ala Cys Thr Cys Asp Pro Arg Gly Ala Leu
625                 630                 635                 640

Asp Gln Leu Cys Gly Ala Gly Gly Leu Cys Arg Cys Arg Pro Gly Tyr
                645                 650                 655

Thr Gly Thr Ala Cys Gln Glu Cys Ser Pro Gly Phe His Gly Phe Pro
            660                 665                 670

Ser Cys Val Pro Cys His Cys Ser Ala Glu Gly Ser Leu His Ala Ala
        675                 680                 685

Cys Asp Pro Arg Ser Gly Gln Cys Ser Cys Arg Pro Arg Val Thr Gly
        690                 695                 700

Leu Arg Cys Asp Thr Cys Val Pro Gly Ala Tyr Asn Phe Pro Tyr Cys
705                 710                 715                 720

Glu Ala Gly Ser Cys His Pro Ala Gly Leu Ala Pro Val Asp Pro Ala
                725                 730                 735

Leu Pro Glu Ala Gln Val Pro Cys Met Cys Arg Ala His Val Glu Gly
            740                 745                 750

Pro Ser Cys Asp Arg Cys Lys Pro Gly Phe Trp Gly Leu Ser Pro Ser
        755                 760                 765

Asn Pro Glu Gly Cys Thr Arg Cys Ser Cys Asp Leu Arg Gly Thr Leu
770                 775                 780

Gly Gly Val Ala Glu Cys Gln Pro Gly Thr Gly Gln Cys Phe Cys Lys
785                 790                 795                 800

Pro His Val Cys Gly Gln Ala Cys Ala Ser Cys Lys Asp Gly Phe Phe
                805                 810                 815

Gly Leu Asp Gln Ala Asp Tyr Phe Gly Cys Arg Ser Cys Arg Cys Asp
            820                 825                 830

Ile Gly Gly Ala Leu Gly Gln Ser Cys Glu Pro Arg Thr Gly Val Cys
        835                 840                 845

Arg Cys Arg Pro Asn Thr Gln Gly Pro Thr Cys Ser Glu Pro Ala Arg
        850                 855                 860

Asp His Tyr Leu Pro Asp Leu His His Leu Arg Leu Glu Leu Glu Glu
865                 870                 875                 880

Ala Ala Thr Pro Glu Gly His Ala Val Arg Phe Gly Phe Asn Pro Leu
                885                 890                 895

Glu Phe Glu Asn Phe Ser Trp Arg Gly Tyr Ala Gln Met Ala Pro Val
            900                 905                 910

Gln Pro Arg Ile Val Ala Arg Leu Asn Leu Thr Ser Pro Asp Leu Phe

```
                915                 920                 925
Trp Leu Val Phe Arg Tyr Val Asn Arg Gly Ala Met Ser Val Ser Gly
        930                 935                 940

Arg Val Ser Val Arg Glu Glu Gly Arg Ser Ala Thr Cys Ala Asn Cys
945                 950                 955                 960

Thr Ala Gln Ser Gln Pro Val Ala Phe Pro Ser Thr Glu Pro Ala
                965                 970                 975

Phe Ile Thr Val Pro Gln Arg Gly Phe Gly Glu Pro Phe Val Leu Asn
            980                 985                 990

Pro Gly Thr Trp Ala Leu Arg Val Glu Ala Glu Gly Val Leu Leu Asp
                995                1000                1005

Tyr Val Val Leu Leu Pro Ser Ala Tyr Glu Ala Ala Leu Leu
    1010                1015                1020

Gln Leu Arg Val Thr Glu Ala Cys Thr Tyr Arg Pro Ser Ala Gln
    1025                1030                1035

Gln Ser Gly Asp Asn Cys Leu Leu Tyr Thr His Leu Pro Leu Asp
    1040                1045                1050

Gly Phe Pro Ser Ala Ala Gly Leu Glu Ala Leu Cys Arg Gln Asp
    1055                1060                1065

Asn Ser Leu Pro Arg Pro Cys Pro Thr Glu Gln Leu Ser Pro Ser
    1070                1075                1080

His Pro Pro Leu Ile Thr Cys Thr Gly Ser Asp Val Asp Val Gln
    1085                1090                1095

Leu Gln Val Ala Val Pro Gln Pro Gly Arg Tyr Ala Leu Val Val
    1100                1105                1110

Glu Tyr Ala Asn Glu Asp Ala Arg Gln Glu Val Gly Val Ala Val
    1115                1120                1125

His Thr Pro Gln Arg Ala Pro Gln Gln Gly Leu Leu Ser Leu His
    1130                1135                1140

Pro Cys Leu Tyr Ser Thr Leu Cys Arg Gly Thr Ala Arg Asp Thr
    1145                1150                1155

Gln Asp His Leu Ala Val Phe His Leu Asp Ser Glu Ala Ser Val
    1160                1165                1170

Arg Leu Thr Ala Glu Gln Ala Arg Phe Phe Leu His Gly Val Thr
    1175                1180                1185

Leu Val Pro Ile Glu Glu Phe Ser Pro Glu Phe Val Glu Pro Arg
    1190                1195                1200

Val Ser Cys Ile Ser Ser His Gly Ala Phe Gly Pro Asn Ser Ala
    1205                1210                1215

Ala Cys Leu Pro Ser Arg Phe Pro Lys Pro Pro Gln Pro Ile Ile
    1220                1225                1230

Leu Arg Asp Cys Gln Val Ile Pro Leu Pro Pro Gly Leu Pro Leu
    1235                1240                1245

Thr His Ala Gln Asp Leu Thr Pro Ala Met Ser Pro Ala Gly Pro
    1250                1255                1260

Arg Pro Arg Pro Pro Thr Ala Val Asp Pro Asp Ala Glu Pro Thr
    1265                1270                1275

Leu Leu Arg Glu Pro Gln Ala Thr Val Val Phe Thr Thr His Val
    1280                1285                1290

Pro Thr Leu Gly Arg Tyr Ala Phe Leu Leu His Gly Tyr Gln Pro
    1295                1300                1305

Ala His Pro Thr Phe Pro Val Glu Val Leu Ile Asn Ala Gly Arg
    1310                1315                1320
```

```
Val Trp Gln Gly His Ala Asn Ala Ser Phe Cys Pro His Gly Tyr
1325                1330                1335

Gly Cys Arg Thr Leu Val Val Cys Glu Gly Gln Ala Leu Leu Asp
1340                1345                1350

Val Thr His Ser Glu Leu Thr Val Thr Val Arg Val Pro Lys Gly
1355                1360                1365

Arg Trp Leu Trp Leu Asp Tyr Val Leu Val Val Pro Glu Asn Val
1370                1375                1380

Tyr Ser Phe Gly Tyr Leu Arg Glu Glu Pro Leu Asp Lys Ser Tyr
1385                1390                1395

Asp Phe Ile Ser His Cys Ala Ala Gln Gly Tyr His Ile Ser Pro
1400                1405                1410

Ser Ser Ser Ser Leu Phe Cys Arg Asn Ala Ala Ala Ser Leu Ser
1415                1420                1425

Leu Phe Tyr Asn Asn Gly Ala Arg Pro Cys Gly Cys His Glu Val
1430                1435                1440

Gly Ala Thr Gly Pro Thr Cys Glu Pro Phe Gly Gly Gln Cys Pro
1445                1450                1455

Cys His Ala His Val Ile Gly Arg Asp Cys Ser Arg Cys Ala Thr
1460                1465                1470

Gly Tyr Trp Gly Phe Pro Asn Cys Arg Pro Cys Asp Cys Gly Ala
1475                1480                1485

Arg Leu Cys Asp Glu Leu Thr Gly Gln Cys Ile Cys Pro Pro Arg
1490                1495                1500

Thr Ile Pro Pro Asp Cys Leu Cys Gln Pro Gln Thr Phe Gly
1505                1510                1515

Cys His Pro Leu Val Gly Cys Glu Glu Cys Asn Cys Ser Gly Pro
1520                1525                1530

Gly Ile Gln Glu Leu Thr Asp Pro Thr Cys Asp Thr Asp Ser Gly
1535                1540                1545

Gln Cys Lys Cys Arg Pro Asn Val Thr Gly Arg Arg Cys Asp Thr
1550                1555                1560

Cys Ser Pro Gly Phe His Gly Tyr Pro Arg Cys Arg Pro Cys Asp
1565                1570                1575

Cys His Glu Ala Gly Thr Ala Pro Gly Val Cys Asp Pro Leu Thr
1580                1585                1590

Gly Gln Cys Tyr Cys Lys Glu Asn Val Gln Gly Pro Lys Cys Asp
1595                1600                1605

Gln Cys Ser Leu Gly Thr Phe Ser Leu Asp Ala Ala Asn Pro Lys
1610                1615                1620

Gly Cys Thr Arg Cys Phe Cys Phe Gly Ala Thr Glu Arg Cys Arg
1625                1630                1635

Ser Ser Ser Tyr Thr Arg Gln Glu Phe Val Asp Met Glu Gly Trp
1640                1645                1650

Val Leu Leu Ser Thr Asp Arg Gln Val Val Pro His Glu Arg Gln
1655                1660                1665

Pro Gly Thr Glu Met Leu Arg Ala Asp Leu Arg His Val Pro Glu
1670                1675                1680

Ala Val Pro Glu Ala Phe Pro Glu Leu Tyr Trp Gln Ala Pro Pro
1685                1690                1695

Ser Tyr Leu Gly Asp Arg Val Ser Ser Tyr Gly Gly Thr Leu Arg
1700                1705                1710
```

```
Tyr Glu Leu His Ser Glu Thr Gln Arg Gly Asp Val Phe Val Pro
1715                1720                1725

Met Glu Ser Arg Pro Asp Val Val Leu Gln Gly Asn Gln Met Ser
1730                1735                1740

Ile Thr Phe Leu Glu Pro Ala Tyr Pro Thr Pro Gly His Val His
1745                1750                1755

Arg Gly Gln Leu Gln Leu Val Glu Gly Asn Phe Arg His Thr Glu
1760                1765                1770

Thr Arg Asn Thr Val Ser Arg Glu Glu Leu Met Met Val Leu Ala
1775                1780                1785

Ser Leu Glu Gln Leu Gln Ile Arg Ala Leu Phe Ser Gln Ile Ser
1790                1795                1800

Ser Ala Val Phe Leu Arg Arg Val Ala Leu Glu Val Ala Ser Pro
1805                1810                1815

Ala Gly Gln Gly Ala Leu Ala Ser Asn Val Glu Leu Cys Leu Cys
1820                1825                1830

Pro Ala Ser Tyr Arg Gly Asp Ser Cys Gln Glu Cys Ala Pro Gly
1835                1840                1845

Phe Tyr Arg Asp Val Lys Gly Leu Phe Leu Gly Arg Cys Val Pro
1850                1855                1860

Cys Gln Cys His Gly His Ser Asp Arg Cys Leu Pro Gly Ser Gly
1865                1870                1875

Val Cys Val Asp Cys Gln His Asn Thr Glu Gly Ala His Cys Glu
1880                1885                1890

Arg Cys Gln Ala Gly Phe Val Ser Ser Arg Asp Asp Pro Ser Ala
1895                1900                1905

Pro Cys Val Ser Cys Pro Cys Pro Leu Ser Val Pro Ser Asn Asn
1910                1915                1920

Phe Ala Glu Gly Cys Val Leu Arg Gly Gly Arg Thr Gln Cys Leu
1925                1930                1935

Cys Lys Pro Gly Tyr Ala Gly Ala Ser Cys Glu Arg Cys Ala Pro
1940                1945                1950

Gly Phe Phe Gly Asn Pro Leu Val Leu Gly Ser Ser Cys Gln Pro
1955                1960                1965

Cys Asp Cys Ser Gly Asn Gly Asp Pro Asn Leu Leu Phe Ser Asp
1970                1975                1980

Cys Asp Pro Leu Thr Gly Ala Cys Arg Gly Cys Leu Arg His Thr
1985                1990                1995

Thr Gly Pro Arg Cys Glu Ile Cys Ala Pro Gly Phe Tyr Gly Asn
2000                2005                2010

Ala Leu Leu Pro Gly Asn Cys Thr Arg Cys Asp Cys Thr Pro Cys
2015                2020                2025

Gly Thr Glu Ala Cys Asp Pro His Ser Gly His Cys Leu Cys Lys
2030                2035                2040

Ala Gly Val Thr Gly Arg Arg Cys Asp Arg Cys Gln Glu Gly His
2045                2050                2055

Phe Gly Phe Asp Gly Cys Gly Cys Arg Pro Cys Ala Cys Gly
2060                2065                2070

Pro Ala Ala Glu Gly Ser Glu Cys His Pro Gln Ser Gly Gln Cys
2075                2080                2085

His Cys Arg Pro Gly Thr Met Gly Pro Gln Cys Arg Glu Cys Ala
2090                2095                2100

Pro Gly Tyr Trp Gly Leu Pro Glu Gln Gly Cys Arg Arg Cys Gln
```

```
                2105                2110                2115
Cys Pro Gly Gly Arg Cys Asp Pro His Thr Gly Arg Cys Asn Cys
        2120                2125                2130
Pro Pro Gly Leu Ser Gly Glu Arg Cys Asp Thr Cys Ser Gln Gln
        2135                2140                2145
His Gln Val Pro Val Pro Gly Pro Val Gly His Ser Ile His
        2150                2155                2160
Cys Glu Val Cys Asp His Cys Val Val Leu Leu Asp Asp Leu
        2165                2170                2175
Glu Arg Ala Gly Ala Leu Leu Pro Ala Ile His Glu Gln Leu Arg
        2180                2185                2190
Gly Ile Asn Ala Ser Ser Met Ala Trp Ala Arg Leu His Arg Leu
        2195                2200                2205
Asn Ala Ser Ile Ala Asp Leu Gln Ser Gln Leu Arg Ser Pro Leu
        2210                2215                2220
Gly Pro Arg His Glu Thr Ala Gln Gln Leu Glu Val Leu Glu Gln
        2225                2230                2235
Gln Ser Thr Ser Leu Gly Gln Asp Ala Arg Arg Leu Gly Gly Gln
        2240                2245                2250
Ala Val Gly Thr Arg Asp Gln Ala Ser Gln Leu Leu Ala Gly Thr
        2255                2260                2265
Glu Ala Thr Leu Gly His Ala Lys Thr Leu Leu Ala Ala Ile Arg
        2270                2275                2280
Ala Val Asp Arg Thr Leu Ser Glu Leu Met Ser Gln Thr Gly His
        2285                2290                2295
Leu Gly Leu Ala Asn Ala Ser Ala Pro Ser Gly Glu Gln Leu Leu
        2300                2305                2310
Arg Thr Leu Ala Glu Val Glu Arg Leu Leu Trp Glu Met Arg Ala
        2315                2320                2325
Arg Asp Leu Gly Ala Pro Gln Ala Ala Glu Ala Glu Leu Ala
        2330                2335                2340
Ala Ala Gln Arg Leu Leu Ala Arg Val Gln Glu Gln Leu Ser Ser
        2345                2350                2355
Leu Trp Glu Glu Asn Gln Ala Leu Ala Thr Gln Thr Arg Asp Arg
        2360                2365                2370
Leu Ala Gln His Glu Ala Gly Leu Met Asp Leu Arg Glu Ala Leu
        2375                2380                2385
Asn Arg Ala Val Asp Ala Thr Arg Glu Ala Gln Glu Leu Asn Ser
        2390                2395                2400
Arg Asn Gln Glu Arg Leu Glu Glu Ala Leu Gln Arg Lys Gln Glu
        2405                2410                2415
Leu Ser Arg Asp Asn Ala Thr Leu Gln Ala Thr Leu His Ala Ala
        2420                2425                2430
Arg Asp Thr Leu Ala Ser Val Phe Arg Leu Leu His Ser Leu Asp
        2435                2440                2445
Gln Ala Lys Glu Glu Leu Glu Arg Leu Ala Ala Ser Leu Asp Gly
        2450                2455                2460
Ala Arg Thr Pro Leu Leu Gln Arg Met Gln Thr Phe Ser Pro Ala
        2465                2470                2475
Gly Ser Lys Leu Arg Leu Val Glu Ala Ala Glu Ala His Ala Gln
        2480                2485                2490
Gln Leu Gly Gln Leu Ala Leu Asn Leu Ser Ser Ile Ile Leu Asp
        2495                2500                2505
```

```
Val Asn Gln Asp Arg Leu Thr Gln Arg Ala Ile Glu Ala Ser Asn
2510                2515                2520

Ala Tyr Ser Arg Ile Leu Gln Ala Val Gln Ala Glu Asp Ala
2525                2530                2535

Ala Gly Gln Ala Leu Gln Gln Ala Asp His Thr Trp Ala Thr Val
2540                2545                2550

Val Arg Gln Gly Leu Val Asp Arg Ala Gln Gln Leu Leu Ala Asn
2555                2560                2565

Ser Thr Ala Leu Glu Glu Ala Met Leu Gln Glu Gln Gln Arg Leu
2570                2575                2580

Gly Leu Val Trp Ala Ala Leu Gln Gly Ala Arg Thr Gln Leu Arg
2585                2590                2595

Asp Val Arg Ala Lys Lys Asp Gln Leu Glu Ala His Ile Gln Ala
2600                2605                2610

Ala Gln Ala Met Leu Ala Met Asp Thr Asp Glu Thr Ser Lys Lys
2615                2620                2625

Ile Ala His Ala Lys Ala Val Ala Ala Glu Ala Gln Asp Thr Ala
2630                2635                2640

Thr Arg Val Gln Ser Gln Leu Gln Ala Met Gln Glu Asn Val Glu
2645                2650                2655

Arg Trp Gln Gly Gln Tyr Glu Gly Leu Arg Gly Gln Asp Leu Gly
2660                2665                2670

Gln Ala Val Leu Asp Ala Gly His Ser Val Ser Thr Leu Glu Lys
2675                2680                2685

Thr Leu Pro Gln Leu Leu Ala Lys Leu Ser Ile Leu Glu Asn Arg
2690                2695                2700

Gly Val His Asn Ala Ser Leu Ala Leu Ser Ala Ser Ile Gly Arg
2705                2710                2715

Val Arg Glu Leu Ile Ala Gln Ala Arg Gly Ala Ala Ser Lys Val
2720                2725                2730

Lys Val Pro Met Lys Phe Asn Gly Arg Ser Gly Val Gln Leu Arg
2735                2740                2745

Thr Pro Arg Asp Leu Ala Asp Leu Ala Ala Tyr Thr Ala Leu Lys
2750                2755                2760

Phe Tyr Leu Gln Gly Pro Glu Pro Glu Pro Gly Gln Gly Thr Glu
2765                2770                2775

Asp Arg Phe Val Met Tyr Met Gly Ser Arg Gln Ala Thr Gly Asp
2780                2785                2790

Tyr Met Gly Val Ser Leu Arg Asp Lys Lys Val His Trp Val Tyr
2795                2800                2805

Gln Leu Gly Glu Ala Gly Pro Ala Val Leu Ser Ile Asp Glu Asp
2810                2815                2820

Ile Gly Glu Gln Phe Ala Ala Val Ser Leu Asp Arg Thr Leu Gln
2825                2830                2835

Phe Gly His Met Ser Val Thr Val Glu Arg Gln Met Ile Gln Glu
2840                2845                2850

Thr Lys Gly Asp Thr Val Ala Pro Gly Ala Glu Gly Leu Leu Asn
2855                2860                2865

Leu Arg Pro Asp Asp Phe Val Phe Tyr Val Gly Gly Tyr Pro Ser
2870                2875                2880

Thr Phe Thr Pro Pro Pro Leu Leu Arg Phe Pro Gly Tyr Arg Gly
2885                2890                2895
```

```
Cys Ile Glu Met Asp Thr Leu Asn Glu Glu Val Val Ser Leu Tyr
2900                2905                2910

Asn Phe Glu Arg Thr Phe Gln Leu Asp Thr Ala Val Asp Arg Pro
2915                2920                2925

Cys Ala Arg Ser Lys Ser Thr Gly Asp Pro Trp Leu Thr Asp Gly
2930                2935                2940

Ser Tyr Leu Asp Gly Thr Gly Phe Ala Arg Ile Ser Phe Asp Ser
2945                2950                2955

Gln Ile Ser Thr Thr Lys Arg Phe Glu Gln Glu Leu Arg Leu Val
2960                2965                2970

Ser Tyr Ser Gly Val Leu Phe Phe Leu Lys Gln Gln Ser Gln Phe
2975                2980                2985

Leu Cys Leu Ala Val Gln Glu Gly Ser Leu Val Leu Leu Tyr Asp
2990                2995                3000

Phe Gly Ala Gly Leu Lys Lys Ala Val Pro Leu Gln Pro Pro Pro
3005                3010                3015

Pro Leu Thr Ser Ala Ser Lys Ala Ile Gln Val Phe Leu Leu Gly
3020                3025                3030

Gly Ser Arg Lys Arg Val Leu Val Arg Val Glu Arg Ala Thr Val
3035                3040                3045

Tyr Ser Val Glu Gln Asp Asn Asp Leu Glu Leu Ala Asp Ala Tyr
3050                3055                3060

Tyr Leu Gly Gly Val Pro Pro Asp Gln Leu Pro Pro Ser Leu Arg
3065                3070                3075

Arg Leu Phe Pro Thr Gly Gly Ser Val Arg Gly Cys Val Lys Gly
3080                3085                3090

Ile Lys Ala Leu Gly Lys Tyr Val Asp Leu Lys Arg Leu Asn Thr
3095                3100                3105

Thr Gly Val Ser Ala Gly Cys Thr Ala Asp Leu Leu Val Gly Arg
3110                3115                3120

Ala Met Thr Phe His Gly His Gly Phe Leu Arg Leu Ala Leu Ser
3125                3130                3135

Asn Val Ala Pro Leu Thr Gly Asn Val Tyr Ser Gly Phe Gly Phe
3140                3145                3150

His Ser Ala Gln Asp Ser Ala Leu Leu Tyr Tyr Arg Ala Ser Pro
3155                3160                3165

Asp Gly Leu Cys Gln Val Ser Leu Gln Gln Gly Arg Val Ser Leu
3170                3175                3180

Gln Leu Leu Arg Thr Glu Val Lys Thr Gln Ala Gly Phe Ala Asp
3185                3190                3195

Gly Ala Pro His Tyr Val Ala Phe Tyr Ser Asn Ala Thr Gly Val
3200                3205                3210

Trp Leu Tyr Val Asp Asp Gln Leu Gln Gln Met Lys Pro His Arg
3215                3220                3225

Gly Pro Pro Pro Glu Leu Gln Pro Gln Pro Glu Gly Pro Pro Arg
3230                3235                3240

Leu Leu Leu Gly Gly Leu Pro Glu Ser Gly Thr Ile Tyr Asn Phe
3245                3250                3255

Ser Gly Cys Ile Ser Asn Val Phe Val Gln Arg Leu Leu Gly Pro
3260                3265                3270

Gln Arg Val Phe Asp Leu Gln Asn Leu Gly Ser Val Asn Val
3275                3280                3285

Ser Thr Gly Cys Ala Pro Ala Leu Gln Ala Gln Thr Pro Gly Leu
```

-continued

```
            3290                3295                3300
Gly Pro Arg Gly Leu Gln Ala Thr Ala Arg Lys Ala Ser Arg Arg
        3305                3310                3315
Ser Arg Gln Pro Ala Arg His Pro Ala Cys Met Leu Pro Pro His
        3320                3325                3330
Leu Arg Thr Thr Arg Asp Ser Tyr Gln Phe Gly Gly Ser Leu Ser
        3335                3340                3345
Ser His Leu Glu Phe Val Gly Ile Leu Ala Arg His Arg Asn Trp
        3350                3355                3360
Pro Ser Leu Ser Met His Val Leu Pro Arg Ser Ser Arg Gly Leu
        3365                3370                3375
Leu Leu Phe Thr Ala Arg Leu Arg Pro Gly Ser Pro Ser Leu Ala
        3380                3385                3390
Leu Phe Leu Ser Asn Gly His Phe Val Ala Gln Met Glu Gly Leu
        3395                3400                3405
Gly Thr Arg Leu Arg Ala Gln Ser Arg Gln Arg Ser Arg Pro Gly
        3410                3415                3420
Arg Trp His Lys Val Ser Val Arg Trp Glu Lys Asn Arg Ile Leu
        3425                3430                3435
Leu Val Thr Asp Gly Ala Arg Ala Trp Ser Gln Glu Gly Pro His
        3440                3445                3450
Arg Gln His Gln Gly Ala Glu His Pro Gln Pro His Thr Leu Phe
        3455                3460                3465
Val Gly Gly Leu Pro Ala Ser Ser His Ser Ser Lys Leu Pro Val
        3470                3475                3480
Thr Val Gly Phe Ser Gly Cys Val Lys Arg Leu Arg Leu His Gly
        3485                3490                3495
Arg Pro Leu Gly Ala Pro Thr Arg Met Ala Gly Val Thr Pro Cys
        3500                3505                3510
Ile Leu Gly Pro Leu Glu Ala Gly Leu Phe Phe Pro Gly Ser Gly
        3515                3520                3525
Gly Val Ile Thr Leu Asp Leu Pro Gly Ala Thr Leu Pro Asp Val
        3530                3535                3540
Gly Leu Glu Leu Glu Val Arg Pro Leu Ala Val Thr Gly Leu Ile
        3545                3550                3555
Phe His Leu Gly Gln Ala Arg Thr Pro Pro Tyr Leu Gln Leu Gln
        3560                3565                3570
Val Thr Glu Lys Gln Val Leu Leu Arg Ala Asp Asp Gly Ala Gly
        3575                3580                3585
Glu Phe Ser Thr Ser Val Thr Arg Pro Ser Val Leu Cys Asp Gly
        3590                3595                3600
Gln Trp His Arg Leu Ala Val Met Lys Ser Gly Asn Val Leu Arg
        3605                3610                3615
Leu Glu Val Asp Ala Gln Ser Asn His Thr Val Gly Pro Leu Leu
        3620                3625                3630
Ala Ala Ala Ala Gly Ala Pro Ala Pro Leu Tyr Leu Gly Gly Leu
        3635                3640                3645
Pro Glu Pro Met Ala Val Gln Pro Trp Pro Pro Ala Tyr Cys Gly
        3650                3655                3660
Cys Met Arg Arg Leu Ala Val Asn Arg Ser Pro Val Ala Met Thr
        3665                3670                3675
Arg Ser Val Glu Val His Gly Ala Val Gly Ala Ser Gly Cys Pro
        3680                3685                3690
```

Ala Ala
    3695

<210> SEQ ID NO 7
<211> LENGTH: 1786
<212> TYPE: PRT
<213> ORGANISM: homo sapiens
<220> FEATURE:
<221> NAME/KEY: MISC_FEATURE
<222> LOCATION: (1)..(1786)

<400> SEQUENCE: 7

Met Gly Leu Leu Gln Leu Leu Ala Phe Ser Phe Leu Ala Leu Cys Arg
1               5                   10                  15

Ala Arg Val Arg Ala Gln Glu Pro Glu Phe Ser Tyr Gly Cys Ala Glu
            20                  25                  30

Gly Ser Cys Tyr Pro Ala Thr Gly Asp Leu Leu Ile Gly Arg Ala Gln
        35                  40                  45

Lys Leu Ser Val Thr Ser Thr Cys Gly Leu His Lys Pro Glu Pro Tyr
    50                  55                  60

Cys Ile Val Ser His Leu Gln Glu Asp Lys Lys Cys Phe Ile Cys Asn
65                  70                  75                  80

Ser Gln Asp Pro Tyr His Glu Thr Leu Asn Pro Asp Ser His Leu Ile
                85                  90                  95

Glu Asn Val Val Thr Thr Phe Ala Pro Asn Arg Leu Lys Ile Trp Trp
            100                 105                 110

Gln Ser Glu Asn Gly Val Glu Asn Val Thr Ile Gln Leu Asp Leu Glu
        115                 120                 125

Ala Glu Phe His Phe Thr His Leu Ile Met Thr Phe Lys Thr Phe Arg
    130                 135                 140

Pro Ala Ala Met Leu Ile Glu Arg Ser Ser Asp Phe Gly Lys Thr Trp
145                 150                 155                 160

Gly Val Tyr Arg Tyr Phe Ala Tyr Asp Cys Glu Ala Ser Phe Pro Gly
                165                 170                 175

Ile Ser Thr Gly Pro Met Lys Lys Val Asp Asp Ile Ile Cys Asp Ser
            180                 185                 190

Arg Tyr Ser Asp Ile Glu Pro Ser Thr Glu Gly Glu Val Ile Phe Arg
        195                 200                 205

Ala Leu Asp Pro Ala Phe Lys Ile Glu Asp Pro Tyr Ser Pro Arg Ile
    210                 215                 220

Gln Asn Leu Leu Lys Ile Thr Asn Leu Arg Ile Lys Phe Val Lys Leu
225                 230                 235                 240

His Thr Leu Gly Asp Asn Leu Leu Asp Ser Arg Met Glu Ile Arg Glu
                245                 250                 255

Lys Tyr Tyr Tyr Ala Val Tyr Asp Met Val Val Arg Gly Asn Cys Phe
            260                 265                 270

Cys Tyr Gly His Ala Ser Glu Cys Ala Pro Val Asp Gly Phe Asn Glu
        275                 280                 285

Glu Val Glu Gly Met Val His Gly His Cys Met Cys Arg His Asn Thr
    290                 295                 300

Lys Gly Leu Asn Cys Glu Leu Cys Met Asp Phe Tyr His Asp Leu Pro
305                 310                 315                 320

Trp Arg Pro Ala Glu Gly Arg Asn Ser Asn Ala Cys Lys Lys Cys Asn
                325                 330                 335

Cys Asn Glu His Ser Ile Ser Cys His Phe Asp Met Ala Val Tyr Leu

```
                340             345             350
Ala Thr Gly Asn Val Ser Gly Val Cys Asp Asp Cys Gln His Asn
            355             360             365
Thr Met Gly Arg Asn Cys Glu Gln Cys Lys Pro Phe Tyr Tyr Gln His
        370             375             380
Pro Glu Arg Asp Ile Arg Asp Pro Asn Phe Cys Glu Arg Cys Thr Cys
385             390             395             400
Asp Pro Ala Gly Ser Gln Asn Glu Gly Ile Cys Asp Ser Tyr Thr Asp
                405             410             415
Phe Ser Thr Gly Leu Ile Ala Gly Gln Cys Arg Cys Lys Leu Asn Val
            420             425             430
Glu Gly Glu His Cys Asp Val Cys Lys Glu Gly Phe Tyr Asp Leu Ser
        435             440             445
Ser Glu Asp Pro Phe Gly Cys Lys Ser Cys Ala Cys Asn Pro Leu Gly
    450             455             460
Thr Ile Pro Gly Gly Asn Pro Cys Asp Ser Glu Thr Gly His Cys Tyr
465             470             475             480
Cys Lys Arg Leu Val Thr Gly Gln His Cys Asp Gln Cys Leu Pro Glu
            485             490             495
His Trp Gly Leu Ser Asn Asp Leu Asp Gly Cys Arg Pro Cys Asp Cys
        500             505             510
Asp Leu Gly Gly Ala Leu Asn Asn Ser Cys Phe Ala Glu Ser Gly Gln
    515             520             525
Cys Ser Cys Arg Pro His Met Ile Gly Arg Gln Cys Asn Glu Val Glu
    530             535             540
Pro Gly Tyr Tyr Phe Ala Thr Leu Asp His Tyr Leu Tyr Glu Ala Glu
545             550             555             560
Glu Ala Asn Leu Gly Pro Gly Val Ser Ile Val Glu Arg Gln Tyr Ile
            565             570             575
Gln Asp Arg Ile Pro Ser Trp Thr Gly Ala Gly Phe Val Arg Val Pro
        580             585             590
Glu Gly Ala Tyr Leu Glu Phe Phe Ile Asp Asn Ile Pro Tyr Ser Met
    595             600             605
Glu Tyr Asp Ile Leu Ile Arg Tyr Glu Pro Gln Leu Pro Asp His Trp
    610             615             620
Glu Lys Ala Val Ile Thr Val Gln Arg Pro Gly Arg Ile Pro Thr Ser
625             630             635             640
Ser Arg Cys Gly Asn Thr Ile Pro Asp Asp Asn Gln Val Val Ser
            645             650             655
Leu Ser Pro Gly Ser Arg Tyr Val Val Leu Pro Arg Pro Val Cys Phe
        660             665             670
Glu Lys Gly Thr Asn Tyr Thr Val Arg Leu Glu Leu Pro Gln Tyr Thr
    675             680             685
Ser Ser Asp Ser Asp Val Glu Ser Pro Tyr Thr Leu Ile Asp Ser Leu
    690             695             700
Val Leu Met Pro Tyr Cys Lys Ser Leu Asp Ile Phe Thr Val Gly Gly
705             710             715             720
Ser Gly Asp Gly Val Val Thr Asn Ser Ala Trp Glu Thr Phe Gln Arg
            725             730             735
Tyr Arg Cys Leu Glu Asn Ser Arg Ser Val Val Lys Thr Pro Met Thr
        740             745             750
Asp Val Cys Arg Asn Ile Ile Phe Ser Ile Ser Ala Leu Leu His Gln
    755             760             765
```

-continued

```
Thr Gly Leu Ala Cys Glu Cys Asp Pro Gln Gly Ser Leu Ser Ser Val
        770             775             780
Cys Asp Pro Asn Gly Gly Gln Cys Gln Cys Arg Pro Asn Val Val Gly
785             790             795             800
Arg Thr Cys Asn Arg Cys Ala Pro Gly Thr Phe Gly Phe Gly Pro Ser
                805             810             815
Gly Cys Lys Pro Cys Glu Cys His Leu Gln Gly Ser Val Asn Ala Phe
            820             825             830
Cys Asn Pro Val Thr Gly Gln Cys His Cys Phe Gln Gly Val Tyr Ala
        835             840             845
Arg Gln Cys Asp Arg Cys Leu Pro Gly His Trp Gly Phe Pro Ser Cys
    850             855             860
Gln Pro Cys Gln Cys Asn Gly His Ala Asp Asp Cys Asp Pro Val Thr
865             870             875             880
Gly Glu Cys Leu Asn Cys Gln Asp Tyr Thr Met Gly His Asn Cys Glu
                885             890             895
Arg Cys Leu Ala Gly Tyr Tyr Gly Asp Pro Ile Ile Gly Ser Gly Asp
            900             905             910
His Cys Arg Pro Cys Pro Cys Pro Asp Gly Pro Asp Ser Gly Arg Gln
        915             920             925
Phe Ala Arg Ser Cys Tyr Gln Asp Pro Val Thr Leu Gln Leu Ala Cys
    930             935             940
Val Cys Asp Pro Gly Tyr Ile Gly Ser Arg Cys Asp Asp Cys Ala Ser
945             950             955             960
Gly Tyr Phe Gly Asn Pro Ser Glu Val Gly Gly Ser Cys Gln Pro Cys
                965             970             975
Gln Cys His Asn Asn Ile Asp Thr Thr Asp Pro Glu Ala Cys Asp Lys
            980             985             990
Glu Thr Gly Arg Cys Leu Lys Cys Leu Tyr His Thr Glu Gly Glu His
        995             1000            1005
Cys Gln Phe Cys Arg Phe Gly Tyr Tyr Gly Asp Ala Leu Gln Gln
    1010            1015            1020
Asp Cys Arg Lys Cys Val Cys Asn Tyr Leu Gly Thr Val Gln Glu
    1025            1030            1035
His Cys Asn Gly Ser Asp Cys Gln Cys Asp Lys Ala Thr Gly Gln
    1040            1045            1050
Cys Leu Cys Leu Pro Asn Val Ile Gly Gln Asn Cys Asp Arg Cys
    1055            1060            1065
Ala Pro Asn Thr Trp Gln Leu Ala Ser Gly Thr Gly Cys Asp Pro
    1070            1075            1080
Cys Asn Cys Asn Ala Ala His Ser Phe Gly Pro Ser Cys Asn Glu
    1085            1090            1095
Phe Thr Gly Gln Cys Gln Cys Met Pro Gly Phe Gly Gly Arg Thr
    1100            1105            1110
Cys Ser Glu Cys Gln Glu Leu Phe Trp Gly Asp Pro Asp Val Glu
    1115            1120            1125
Cys Arg Ala Cys Asp Cys Asp Pro Arg Gly Ile Glu Thr Pro Gln
    1130            1135            1140
Cys Asp Gln Ser Thr Gly Gln Cys Val Cys Val Glu Gly Val Glu
    1145            1150            1155
Gly Pro Arg Cys Asp Lys Cys Thr Arg Gly Tyr Ser Gly Val Phe
    1160            1165            1170
```

```
Pro Asp Cys Thr Pro Cys His Gln Cys Phe Ala Leu Trp Asp Val
1175                 1180                1185

Ile Ile Ala Glu Leu Thr Asn Arg Thr His Arg Phe Leu Glu Lys
1190                 1195                1200

Ala Lys Ala Leu Lys Ile Ser Gly Val Ile Gly Pro Tyr Arg Glu
1205                 1210                1215

Thr Val Asp Ser Val Glu Arg Lys Val Ser Glu Ile Lys Asp Ile
1220                 1225                1230

Leu Ala Gln Ser Pro Ala Ala Glu Pro Leu Lys Asn Ile Gly Asn
1235                 1240                1245

Leu Phe Glu Glu Ala Glu Lys Leu Ile Lys Asp Val Thr Glu Met
1250                 1255                1260

Met Ala Gln Val Glu Val Lys Leu Ser Asp Thr Thr Ser Gln Ser
1265                 1270                1275

Asn Ser Thr Ala Lys Glu Leu Asp Ser Leu Gln Thr Glu Ala Glu
1280                 1285                1290

Ser Leu Asp Asn Thr Val Lys Glu Leu Ala Glu Gln Leu Glu Phe
1295                 1300                1305

Ile Lys Asn Ser Asp Ile Arg Gly Ala Leu Asp Ser Ile Thr Lys
1310                 1315                1320

Tyr Phe Gln Met Ser Leu Glu Ala Glu Glu Arg Val Asn Ala Ser
1325                 1330                1335

Thr Thr Glu Pro Asn Ser Thr Val Glu Gln Ser Ala Leu Met Arg
1340                 1345                1350

Asp Arg Val Glu Asp Val Met Met Glu Arg Glu Ser Gln Phe Lys
1355                 1360                1365

Glu Lys Gln Glu Glu Gln Ala Arg Leu Leu Asp Glu Leu Ala Gly
1370                 1375                1380

Lys Leu Gln Ser Leu Asp Leu Ser Ala Ala Ala Glu Met Thr Cys
1385                 1390                1395

Gly Thr Pro Pro Gly Ala Ser Cys Ser Glu Thr Glu Cys Gly Gly
1400                 1405                1410

Pro Asn Cys Arg Thr Asp Glu Gly Glu Arg Lys Cys Gly Gly Pro
1415                 1420                1425

Gly Cys Gly Gly Leu Val Thr Val Ala His Asn Ala Trp Gln Lys
1430                 1435                1440

Ala Met Asp Leu Asp Gln Asp Val Leu Ser Ala Leu Ala Glu Val
1445                 1450                1455

Glu Gln Leu Ser Lys Met Val Ser Glu Ala Lys Leu Arg Ala Asp
1460                 1465                1470

Glu Ala Lys Gln Ser Ala Glu Asp Ile Leu Leu Lys Thr Asn Ala
1475                 1480                1485

Thr Lys Glu Lys Met Asp Lys Ser Asn Glu Glu Leu Arg Asn Leu
1490                 1495                1500

Ile Lys Gln Ile Arg Asn Phe Leu Thr Gln Asp Ser Ala Asp Leu
1505                 1510                1515

Asp Ser Ile Glu Ala Val Ala Asn Glu Val Leu Lys Met Glu Met
1520                 1525                1530

Pro Ser Thr Pro Gln Gln Leu Gln Asn Leu Thr Glu Asp Ile Arg
1535                 1540                1545

Glu Arg Val Glu Ser Leu Ser Gln Val Glu Val Ile Leu Gln His
1550                 1555                1560

Ser Ala Ala Asp Ile Ala Arg Ala Glu Met Leu Leu Glu Glu Ala
```

```
                 1565                1570                1575

Lys Arg Ala Ser Lys Ser Ala Thr Asp Val Lys Val Thr Ala Asp
            1580                1585                1590

Met Val Lys Glu Ala Leu Glu Ala Glu Lys Ala Gln Val Ala
        1595                1600                1605

Ala Glu Lys Ala Ile Lys Gln Ala Asp Glu Asp Ile Gln Gly Thr
        1610                1615                1620

Gln Asn Leu Leu Thr Ser Ile Glu Ser Glu Thr Ala Ala Ser Glu
        1625                1630                1635

Glu Thr Leu Phe Asn Ala Ser Gln Arg Ile Ser Glu Leu Glu Arg
        1640                1645                1650

Asn Val Glu Glu Leu Lys Arg Lys Ala Ala Gln Asn Ser Gly Glu
        1655                1660                1665

Ala Glu Tyr Ile Glu Lys Val Val Tyr Thr Val Lys Gln Ser Ala
        1670                1675                1680

Glu Asp Val Lys Lys Thr Leu Asp Gly Glu Leu Asp Glu Lys Tyr
        1685                1690                1695

Lys Lys Val Glu Asn Leu Ile Ala Lys Lys Thr Glu Glu Ser Ala
        1700                1705                1710

Asp Ala Arg Arg Lys Ala Glu Met Leu Gln Asn Glu Ala Lys Thr
        1715                1720                1725

Leu Leu Ala Gln Ala Asn Ser Lys Leu Gln Leu Leu Lys Asp Leu
        1730                1735                1740

Glu Arg Lys Tyr Glu Asp Asn Gln Arg Tyr Leu Glu Asp Lys Ala
        1745                1750                1755

Gln Glu Leu Ala Arg Leu Glu Gly Glu Val Arg Ser Leu Leu Lys
        1760                1765                1770

Asp Ile Ser Gln Lys Val Ala Val Tyr Ser Thr Cys Leu
        1775                1780                1785

<210> SEQ ID NO 8
<211> LENGTH: 1609
<212> TYPE: PRT
<213> ORGANISM: homo sapiens
<220> FEATURE:
<221> NAME/KEY: MISC_FEATURE
<222> LOCATION: (1)..(1609)

<400> SEQUENCE: 8

Met Arg Gly Ser His Arg Ala Ala Pro Ala Leu Arg Pro Gly Arg
1               5                   10                  15

Leu Trp Pro Val Leu Ala Val Leu Ala Ala Ala Ala Ala Gly Cys
            20                  25                  30

Ala Gln Ala Ala Met Asp Glu Cys Thr Asp Glu Gly Gly Arg Pro Gln
        35                  40                  45

Arg Cys Met Pro Glu Phe Val Asn Ala Ala Phe Asn Val Thr Val Val
    50                  55                  60

Ala Thr Asn Thr Cys Gly Thr Pro Pro Glu Glu Tyr Cys Val Gln Thr
65                  70                  75                  80

Gly Val Thr Gly Val Thr Lys Ser Cys His Leu Cys Asp Ala Gly Gln
                85                  90                  95

Pro His Leu Gln His Gly Ala Ala Phe Leu Thr Asp Tyr Asn Asn Gln
            100                 105                 110

Ala Asp Thr Thr Trp Trp Gln Ser Gln Thr Met Leu Ala Gly Val Gln
        115                 120                 125
```

```
Tyr Pro Ser Ser Ile Asn Leu Thr Leu His Leu Gly Lys Ala Phe Asp
    130                 135                 140

Ile Thr Tyr Val Arg Leu Lys Phe His Thr Ser Arg Pro Glu Ser Phe
145                 150                 155                 160

Ala Ile Tyr Lys Arg Thr Arg Glu Asp Gly Pro Trp Ile Pro Tyr Gln
                165                 170                 175

Tyr Tyr Ser Gly Ser Cys Glu Asn Thr Tyr Ser Lys Ala Asn Arg Gly
            180                 185                 190

Phe Ile Arg Thr Gly Gly Asp Glu Gln Gln Ala Leu Cys Thr Asp Glu
                195                 200                 205

Phe Ser Asp Ile Ser Pro Leu Thr Gly Gly Asn Val Ala Phe Ser Thr
    210                 215                 220

Leu Glu Gly Arg Pro Ser Ala Tyr Asn Phe Asp Asn Ser Pro Val Leu
225                 230                 235                 240

Gln Glu Trp Val Thr Ala Thr Asp Ile Arg Val Thr Leu Asn Arg Leu
                245                 250                 255

Asn Thr Phe Gly Asp Glu Val Phe Asn Asp Pro Lys Val Leu Lys Ser
            260                 265                 270

Tyr Tyr Tyr Ala Ile Ser Asp Phe Ala Val Gly Gly Arg Cys Lys Cys
    275                 280                 285

Asn Gly His Ala Ser Glu Cys Met Lys Asn Glu Phe Asp Lys Leu Val
    290                 295                 300

Cys Asn Cys Lys His Asn Thr Tyr Gly Val Asp Cys Glu Lys Cys Leu
305                 310                 315                 320

Pro Phe Phe Asn Asp Arg Pro Trp Arg Arg Ala Thr Ala Glu Ser Ala
                325                 330                 335

Ser Glu Cys Leu Pro Cys Asp Cys Asn Gly Arg Ser Gln Glu Cys Tyr
            340                 345                 350

Phe Asp Pro Glu Leu Tyr Arg Ser Thr Gly His Gly Gly His Cys Thr
            355                 360                 365

Asn Cys Gln Asp Asn Thr Asp Gly Ala His Cys Glu Arg Cys Arg Glu
    370                 375                 380

Asn Phe Phe Arg Leu Gly Asn Asn Glu Ala Cys Ser Ser Cys His Cys
385                 390                 395                 400

Ser Pro Val Gly Ser Leu Ser Thr Gln Cys Asp Ser Tyr Gly Arg Cys
                405                 410                 415

Ser Cys Lys Pro Gly Val Met Gly Asp Lys Cys Asp Arg Cys Gln Pro
            420                 425                 430

Gly Phe His Ser Leu Thr Glu Ala Gly Cys Arg Pro Cys Ser Cys Asp
            435                 440                 445

Pro Ser Gly Ser Ile Asp Glu Cys Asn Ile Glu Thr Gly Arg Cys Val
    450                 455                 460

Cys Lys Asp Asn Val Glu Gly Phe Asn Cys Glu Arg Cys Lys Pro Gly
465                 470                 475                 480

Phe Phe Asn Leu Glu Ser Ser Asn Pro Arg Gly Cys Thr Pro Cys Phe
                485                 490                 495

Cys Phe Gly His Ser Ser Val Cys Thr Asn Ala Val Gly Tyr Ser Val
            500                 505                 510

Tyr Ser Ile Ser Ser Thr Phe Gln Ile Asp Glu Asp Gly Trp Arg Ala
            515                 520                 525

Glu Gln Arg Asp Gly Ser Glu Ala Ser Leu Glu Trp Ser Ser Glu Arg
    530                 535                 540

Gln Asp Ile Ala Val Ile Ser Asp Ser Tyr Phe Pro Arg Tyr Phe Ile
```

```
                545                 550                 555                 560
        Ala Pro Ala Lys Phe Leu Gly Lys Gln Val Leu Ser Tyr Gly Gln Asn
                        565                 570                 575
        Leu Ser Phe Ser Phe Arg Val Asp Arg Arg Asp Thr Arg Leu Ser Ala
                        580                 585                 590
        Glu Asp Leu Val Leu Glu Gly Ala Gly Leu Arg Val Ser Val Pro Leu
                        595                 600                 605
        Ile Ala Gln Gly Asn Ser Tyr Pro Ser Glu Thr Thr Val Lys Tyr Val
                        610                 615                 620
        Phe Arg Leu His Glu Ala Thr Asp Tyr Pro Trp Arg Pro Ala Leu Thr
        625                 630                 635                 640
        Pro Phe Glu Phe Gln Lys Leu Leu Asn Asn Leu Thr Ser Ile Lys Ile
                        645                 650                 655
        Arg Gly Thr Tyr Ser Glu Arg Ser Ala Gly Tyr Leu Asp Asp Val Thr
                        660                 665                 670
        Leu Ala Ser Ala Arg Pro Gly Pro Gly Val Pro Ala Thr Trp Val Glu
                        675                 680                 685
        Ser Cys Thr Cys Pro Val Gly Tyr Gly Gly Gln Phe Cys Glu Met Cys
                        690                 695                 700
        Leu Ser Gly Tyr Arg Arg Glu Thr Pro Asn Leu Gly Pro Tyr Ser Pro
        705                 710                 715                 720
        Cys Val Leu Cys Ala Cys Asn Gly His Ser Glu Thr Cys Asp Pro Glu
                        725                 730                 735
        Thr Gly Val Cys Asn Cys Arg Asp Asn Thr Ala Gly Pro His Cys Glu
                        740                 745                 750
        Lys Cys Ser Asp Gly Tyr Tyr Gly Asp Ser Thr Ala Gly Thr Ser Ser
                        755                 760                 765
        Asp Cys Gln Pro Cys Pro Cys Pro Gly Gly Ser Ser Cys Ala Val Val
                        770                 775                 780
        Pro Lys Thr Lys Glu Val Val Cys Thr Asn Cys Pro Thr Gly Thr Thr
        785                 790                 795                 800
        Gly Lys Arg Cys Glu Leu Cys Asp Asp Gly Tyr Phe Gly Asp Pro Leu
                        805                 810                 815
        Gly Arg Asn Gly Pro Val Arg Leu Cys Arg Leu Cys Gln Cys Ser Asp
                        820                 825                 830
        Asn Ile Asp Pro Asn Ala Val Gly Asn Cys Asn Arg Leu Thr Gly Glu
                        835                 840                 845
        Cys Leu Lys Cys Ile Tyr Asn Thr Ala Gly Phe Tyr Cys Asp Arg Cys
                        850                 855                 860
        Lys Asp Gly Phe Phe Gly Asn Pro Leu Ala Pro Asn Pro Ala Asp Lys
        865                 870                 875                 880
        Cys Lys Ala Cys Asn Cys Asn Leu Tyr Gly Thr Met Lys Gln Gln Ser
                        885                 890                 895
        Ser Cys Asn Pro Val Thr Gly Gln Cys Glu Cys Leu Pro His Val Thr
                        900                 905                 910
        Gly Gln Asp Cys Gly Ala Cys Asp Pro Gly Phe Tyr Asn Leu Gln Ser
                        915                 920                 925
        Gly Gln Gly Cys Glu Arg Cys Asp Cys His Ala Leu Gly Ser Thr Asn
                        930                 935                 940
        Gly Gln Cys Asp Ile Arg Thr Gly Gln Cys Glu Cys Gln Pro Gly Ile
        945                 950                 955                 960
        Thr Gly Gln His Cys Glu Arg Cys Glu Val Asn His Phe Gly Phe Gly
                        965                 970                 975
```

```
Pro Glu Gly Cys Lys Pro Cys Asp Cys His Pro Glu Gly Ser Leu Ser
            980                 985                 990

Leu Gln Cys Lys Asp Asp Gly Arg Cys Glu Cys Arg Glu Gly Phe Val
        995                1000               1005

Gly Asn Arg Cys Asp Gln Cys Glu Glu Asn Tyr Phe Tyr Asn Arg
        1010                1015               1020

Ser Trp Pro Gly Cys Gln Glu Cys Pro Ala Cys Tyr Arg Leu Val
        1025                1030               1035

Lys Asp Lys Val Ala Asp His Arg Val Lys Leu Gln Glu Leu Glu
        1040                1045               1050

Ser Leu Ile Ala Asn Leu Gly Thr Gly Asp Glu Met Val Thr Asp
        1055                1060               1065

Gln Ala Phe Glu Asp Arg Leu Lys Glu Ala Glu Arg Glu Val Met
        1070                1075               1080

Asp Leu Leu Arg Glu Ala Gln Asp Val Lys Asp Val Asp Gln Asn
        1085                1090               1095

Leu Met Asp Arg Leu Gln Arg Val Asn Asn Thr Leu Ser Ser Gln
        1100                1105               1110

Ile Ser Arg Leu Gln Asn Ile Arg Asn Thr Ile Glu Glu Thr Gly
        1115                1120               1125

Asn Leu Ala Glu Gln Ala Arg Ala His Val Glu Asn Thr Glu Arg
        1130                1135               1140

Leu Ile Glu Ile Ala Ser Arg Glu Leu Glu Lys Ala Lys Val Ala
        1145                1150               1155

Ala Ala Asn Val Ser Val Thr Gln Pro Glu Ser Thr Gly Asp Pro
        1160                1165               1170

Asn Asn Met Thr Leu Leu Ala Glu Glu Ala Arg Lys Leu Ala Glu
        1175                1180               1185

Arg His Lys Gln Glu Ala Asp Asp Ile Val Arg Val Ala Lys Thr
        1190                1195               1200

Ala Asn Asp Thr Ser Thr Glu Ala Tyr Asn Leu Leu Leu Arg Thr
        1205                1210               1215

Leu Ala Gly Glu Asn Gln Thr Ala Phe Glu Ile Glu Glu Leu Asn
        1220                1225               1230

Arg Lys Tyr Glu Gln Ala Lys Asn Ile Ser Gln Asp Leu Glu Lys
        1235                1240               1245

Gln Ala Ala Arg Val His Glu Glu Ala Lys Arg Ala Gly Asp Lys
        1250                1255               1260

Ala Val Glu Ile Tyr Ala Ser Val Ala Gln Leu Ser Pro Leu Asp
        1265                1270               1275

Ser Glu Thr Leu Glu Asn Glu Ala Asn Asn Ile Lys Met Glu Ala
        1280                1285               1290

Glu Asn Leu Glu Gln Leu Ile Asp Gln Lys Leu Lys Asp Tyr Glu
        1295                1300               1305

Asp Leu Arg Glu Asp Met Arg Gly Lys Glu Leu Glu Val Lys Asn
        1310                1315               1320

Leu Leu Glu Lys Gly Lys Thr Glu Gln Gln Thr Ala Asp Gln Leu
        1325                1330               1335

Leu Ala Arg Ala Asp Ala Ala Lys Ala Leu Ala Glu Glu Ala Ala
        1340                1345               1350

Lys Lys Gly Arg Asp Thr Leu Gln Glu Ala Asn Asp Ile Leu Asn
        1355                1360               1365
```

-continued

```
Asn Leu Lys Asp Phe Asp Arg Arg Val Asn Asp Asn Lys Thr Ala
    1370            1375            1380

Ala Glu Glu Ala Leu Arg Lys Ile Pro Ala Ile Asn Gln Thr Ile
    1385            1390            1395

Thr Glu Ala Asn Glu Lys Thr Arg Glu Ala Gln Gln Ala Leu Gly
    1400            1405            1410

Ser Ala Ala Ala Asp Ala Thr Glu Ala Lys Asn Lys Ala His Glu
    1415            1420            1425

Ala Glu Arg Ile Ala Ser Ala Val Gln Lys Asn Ala Thr Ser Thr
    1430            1435            1440

Lys Ala Glu Ala Glu Arg Thr Phe Ala Glu Val Thr Asp Leu Asp
    1445            1450            1455

Asn Glu Val Asn Asn Met Leu Lys Gln Leu Gln Glu Ala Glu Lys
    1460            1465            1470

Glu Leu Lys Arg Lys Gln Asp Asp Ala Asp Gln Asp Met Met Met
    1475            1480            1485

Ala Gly Met Ala Ser Gln Ala Ala Gln Glu Ala Glu Ile Asn Ala
    1490            1495            1500

Arg Lys Ala Lys Asn Ser Val Thr Ser Leu Leu Ser Ile Ile Asn
    1505            1510            1515

Asp Leu Leu Glu Gln Leu Gly Gln Leu Asp Thr Val Asp Leu Asn
    1520            1525            1530

Lys Leu Asn Glu Ile Glu Gly Thr Leu Asn Lys Ala Lys Asp Glu
    1535            1540            1545

Met Lys Val Ser Asp Leu Asp Arg Lys Val Ser Asp Leu Glu Asn
    1550            1555            1560

Glu Ala Lys Lys Gln Glu Ala Ala Ile Met Asp Tyr Asn Arg Asp
    1565            1570            1575

Ile Glu Glu Ile Met Lys Asp Ile Arg Asn Leu Glu Asp Ile Arg
    1580            1585            1590

Lys Thr Leu Pro Ser Gly Cys Phe Asn Thr Pro Ser Ile Glu Lys
    1595            1600            1605

Pro
```

METHODS FOR MODULATING HAIR GROWTH USING TRUNCATED LAMININ-511

RELATED APPLICATION

This application claims priority and other benefits from U.S. Provisional Patent Application Ser. No. 61/615,330 filed Mar. 25, 2012, entitled "Methods For Modulating Hair Growth Using Truncated Laminin-511". Its entire content is specifically incorporated herein by reference. Furthermore, this application claims priority as the U.S. national stage application of PCT/US13/32716, having an international filing date of Mar. 15, 2013, which is hereby incorporated in its entirety.

STATEMENT OF GOVERNMENTAL SUPPORT

This invention was made with government support under AR047223 awarded by the National Institutes of Health. The government has certain rights in this invention.

TECHNICAL FIELD OF THE INVENTION

The present invention relates to methods for promoting hair growth in cases of alopecia and other hair deficiency disorders, using a truncated, recombinant laminin-511; the present invention, furthermore, relates to methods for decreasing hair growth in areas of unwanted hair growth, using modulators of full-length laminin-511 expression or function.

BACKGROUND

Hair is one of the defining characteristics of humans and mammals in general. With the exception of mucus membranes and glabrous skin, hair grows everywhere on a mammal's skin. Fine, short, light colored and barely noticeable 'vellus hair' growths initially during childhood, which is then gradually replaced by thick, long and colorful terminal hair from puberty onwards. The increase in androgenic hormone levels, particularly from the testosterone family, during puberty causes vellus hair to be replaced with terminal hair, as evidenced in the growth of terminal hair in the axillary, facial and pubic areas as well as on legs, arms and chest.

Changes in the levels of testosterone and testosterone derivatives drive both the change from vellus to terminal hair during puberty and, later in life, the more or less gradual onset of hair loss, which in either case naturally affect males more than females.

Hair growth begins inside the hair follicle, a minuscular, highly regenerative organ located in the dermis layer of mammalian skin that contains numerous mesenchymal stem cells for regrowing hair, once it has fallen out, as well as for regrowing skin, if it gets wounded. Each hair consists of a shaft, which is the hard filamentous part that extends above the skin or scalp surface, and a root or bulb that is embedded in the hair follicle. The human scalp contains in average about 100,000 to 150,000 hairs, with each hair having an average life span of several years.

The hair follicle perpetually undergoes cyclic transformations between phases of a) rapid growth where the hair shaft is produced and growths in length (anagen phase), b) a short transition stage that occurs at the end of the anagen phase (catagen phase) and c) a resting phase (telogen phase). It is the activity of the hair follicles that primarily determines hair growth and renewal (Krause & Foitzik, 2006). Typically, up to 90% of the hair follicles are in the anagen phase, about 1-2% in the catagen phase and about 8% in the telogen phase. For scalp hair, such a cycle takes several years to finish.

The final product of a hair follicle in the telogen stage is dead, fully keratinized hair (club hair); in average, 50-100 club hairs are daily shed from a regular scalp. Disturbances in the hair follicle cycling and hair morphogenesis can lead to unwanted hair loss or unwanted excessive hair growth with often profound impact on an individual's well-being far beyond the purely cosmetic aspect.

Alopecia, an androgen-mediated thinning of the scalp hair in men and women, is caused by a progressive shortening of the anagen growth cycle due to an oversensitivity to dihydrotestosterone. In men and women, a usually small percentage of testosterone undergoes reduction by the 5α-reductase to dihydrotestosterone. Depending on the genetic make-up of an individual, a higher percentage of testosterone can be converted to dihydrotestosterone, making the individual, thus, more prone to hair loss. An oversensitivity to dihydrotestosterone results in increased hair loss and by a gradual miniaturization and conversion of the hair follicles into vellus hair follicles which no longer produce thick, terminal hair, but hardly visible, depigmented hair. Loss of scalp hair starts usually at the temples and on the crown of the head and is more pronounced in men than in women. Alopecia can also be induced by chemical agents and is a frequently experienced adverse effect during anti-cancer chemotherapy. While alopecia is a serious disorder of hair growth and causes great psychological stress among the concerned, hair follicles are still present and are still cycling, which is critical, if reversal of hair loss is attempted.

Currently available treatments to address alopecia include the topical or oral application of pharmaceuticals, such as minoxidil (De Villez, 1985) or finasteride. Minoxidil, a vasodilating agent whose first indication is to lower arterial blood pressure, seems to only be effective at the start of androgenic alopecia and seems only to prevent hair loss, but does not seem to be able to effect new hair growth. Finasteride, a synthetic antiandrogen and specific inhibitor of type II 5α-reductase that transforms testosterone into dihydrotestosterone, has been shown to effectively decrease serum and scalp dihydrotestosterone (Leyden et al., 1999). However, since Finasteride is contraindicated in women and since it might also carry the risk for increased incidence of prostate cancer in men, its use is limited to men, carries risks and is not suited for long-term use.

Abnormally increased hair growth, as it is the case with hirsutism, an excessive androgen-dependent hair growth in women, and hypertrichosis, an excessive androgen-independent hair growth, results from an extended anagen phase with an unusual enlargement of hair follicles accompanied by the conversion of terminal to vellus hair follicles and consequential growth of terminal, thick hair instead of hardly visible, depigmented hair.

Cosmetic adjustment of hair growth is a further reason in today's society to modulate hair growth. Current methods for hair removal include shaving, electrolysis, depilatory creams and waxing, while the local application of herbal mixtures has been tried to encourage hair growth.

Far beyond posing a purely cosmetic problem, abnormal hair growth can seriously affect an individual's self-esteem and overall well-being. Currently available methods for modulating hair growth are not effective to achieve a measureable and sustainable improvement in hair growth. It would be highly desirable to have improved methods for

SUMMARY

In one aspect, the present invention relates to biodegradable or biocompatible microneedle array devices and methods of their use for the topical, including dermal, application of a laminin-511 peptide or protein to a subject in order to increase scalp hair growth and, additionally or alternatively, to decrease scalp hair loss in a subject. In one embodiment, the laminin-511 is a truncated, recombinant laminin-511 trimer comprising an alpha-5 chain comprising a sequence substantially identical to SEQ ID NO:1; a beta-1 chain comprising a sequence substantially identical to SEQ ID NO:2; and a gamma-1 chain comprising a sequence substantially identical to SEQ ID NO:3. In another embodiment, the laminin-511 is a truncated, recombinant laminin-511 trimer comprising an alpha-5 chain comprising a sequence substantially identical to SEQ ID NO:4; a beta-1 chain comprising a sequence substantially identical to SEQ ID NO:2; and a gamma-1 chain comprising a sequence substantially identical to SEQ ID NO:3. In a further embodiment, the laminin-511 is a truncated, recombinant laminin-511 trimer comprising an alpha-5 chain comprising a sequence substantially identical to SEQ ID NO:5; a beta-1 chain comprising a sequence substantially identical to SEQ ID NO:2; and a gamma-1 chain comprising a sequence substantially identical to SEQ ID NO:3. In another embodiment, the laminin-511 is a full-length laminin-511 trimer comprising an alpha-5 chain comprising a sequence substantially identical to SEQ ID NO:6; a beta-1 chain comprising a sequence substantially identical to SEQ ID NO:7; and a gamma-1 chain comprising a sequence substantially identical to SEQ ID NO:8. In the various embodiments, the microneedle array devices may, in addition, comprise at least one secondary treatment product.

In another aspect, the present invention relates to biodegradable or biocompatible microneedle array devices and methods of their use for the topical, including dermal, application of an agent capable of reducing expression of endogenous full-length laminin-511 trimer, which comprises an alpha-5 chain consisting of SEQ ID NO:6, a beta-1 chain consisting of SEQ ID NO:7 and a gamma-1 chain consisting of SEQ ID NO:8, to a subject in order to decrease hair growth. In one embodiment, the agent is a small interfering ribonucleic acid (siRNA) against endogenous full-length laminin-511. In another embodiment, the agent is a small hairpin ribonucleic acid (shRNA) against endogenous full-length laminin-511. In yet another embodiment, the agent is an antisense oligonucleotide against endogenous full-length laminin-511. In the various embodiments, the microneedle array devices may, in addition, comprise at least one secondary treatment product.

In a further aspect, the present invention relates to biodegradable or biocompatible microneedle array devices and methods of their use for the topical, including dermal, application of a small molecule, that is capable of blocking the interaction between endogenous full-length laminin-511 and integrin receptors, to decrease hair growth in a subject. In the various embodiments, the microneedle array devices may, in addition, comprise at least one secondary treatment product.

In another aspect, the present invention relates to methods for increasing scalp hair growth and, additionally or alternatively, for decreasing scalp hair loss in a subject using a topically, including dermally, administered truncated, recombinant laminin-511 peptide or protein. In one embodiment, the truncated, recombinant laminin-511 comprises an alpha-5 chain comprising a sequence substantially identical to SEQ ID NO:1, a beta-1 chain comprising a sequence substantially identical to SEQ ID NO:2, and a gamma-1 chain comprising a sequence substantially identical to SEQ ID NO:3. In another embodiment, the truncated, recombinant laminin-511 comprises an alpha-5 chain comprising a sequence substantially identical to SEQ ID NO:4, a beta-1 chain comprising a sequence substantially identical to SEQ ID NO:2, and a gamma-1 chain comprising a sequence substantially identical to SEQ ID NO:3. In a further embodiment, the truncated, recombinant laminin-511 comprises an alpha-5 chain comprising a sequence substantially identical to SEQ ID NO:5, a beta-1 chain comprising a sequence substantially identical to SEQ ID NO:2, and a gamma-1 chain comprising a sequence substantially identical to SEQ ID NO:3.

It is contemplated in the various embodiments that the truncated, recombinant laminin-511 can have at least one substitution in at least one alpha, beta or gamma chain in which a residue is replaced with a structurally related residue. Furthermore, in the various embodiments, the truncated, recombinant laminin-511 may be administered before, after or together with at least one secondary treatment product.

In another aspect, the present invention relates to methods for decreasing hair growth in a subject at areas where hair growth is undesired, using a topically, including dermally, administered agent that is capable of reducing the expression of endogenous full-length laminin-511. In one embodiment, the agent is a small interfering ribonucleic acid against endogenous full-length laminin-511. In another embodiment, the agent is a small hairpin ribonucleic acid against endogenous full-length laminin-511. In yet another embodiment, the agent is an antisense oligonucleotide against endogenous full-length laminin-511. In the various embodiments, the agents may be administered before, after or together with at least one secondary treatment product.

In a further aspect, the present invention relates to methods for decreasing hair growth in a subject at areas where hair growth is undesired, using a topically, including dermally, administered small molecule that is capable of blocking the interaction between endogenous full-length laminin-511 and integrin receptors. In the various embodiments, the agent may be administered before, after or together with at least one secondary treatment product.

In another aspect, the present invention provides kits for carrying out procedures to increase scalp hair growth and, additionally or alternatively, to decrease scalp hair loss in a subject, using a suitable microneedle device, as described earlier, and a truncated, recombinant laminin-511 peptide or protein. In the various embodiments, the kit may additionally contain at least one secondary treatment product.

In yet another aspect, the present invention provides kits for carrying out procedures to decrease hair growth in a subject in areas where hair growth is undesired, using a suitable microneedle device, as described earlier, and an agent that is capable of reducing the expression of endogenous full-length laminin-511. In the various embodiments, the kit may additionally contain at least one secondary treatment product.

In a further aspect, the present invention provides kits for carrying out procedures to decrease hair growth in a subject in areas where hair growth is undesired, using a suitable microneedle device, as described earlier, and a small molecule that is capable of blocking the interaction between endogenous full-length laminin-511 and integrin receptors. In the various embodiments, the kit may additionally contain at least one secondary treatment product.

The above summary is not intended to include all features and aspects of the present invention nor does it imply that the invention must include all features and aspects discussed in this summary.

INCORPORATION BY REFERENCE

All publications mentioned in this specification are herein incorporated by reference to the same extent as if each individual publication or patent application was specifically and individually indicated to be incorporated by reference.

BRIEF DESCRIPTION OF THE DRAWINGS

The accompanying drawings illustrate embodiments of the invention and, together with the description, serve to explain the invention. These drawings are offered by way of illustration and not by way of limitation; it is emphasized that the various features of the drawings may not be to-scale.

FIG. 1A shows hematoxylin and eosin (H&E)-stained cross-sectional views of control (left), while FIG. 1B shows dorsal skin regions that were treated with truncated, recombinant laminin-511. FIG. 1C shows a comparison of the number of hair follicles grown in control mice with the number of hair follicles in mice following treatment with truncated, recombinant laminin-511. Treatment with the truncated, recombinant laminin-511 had significantly increased hair follicle growth.

DETAILED DESCRIPTION

Figure 1:
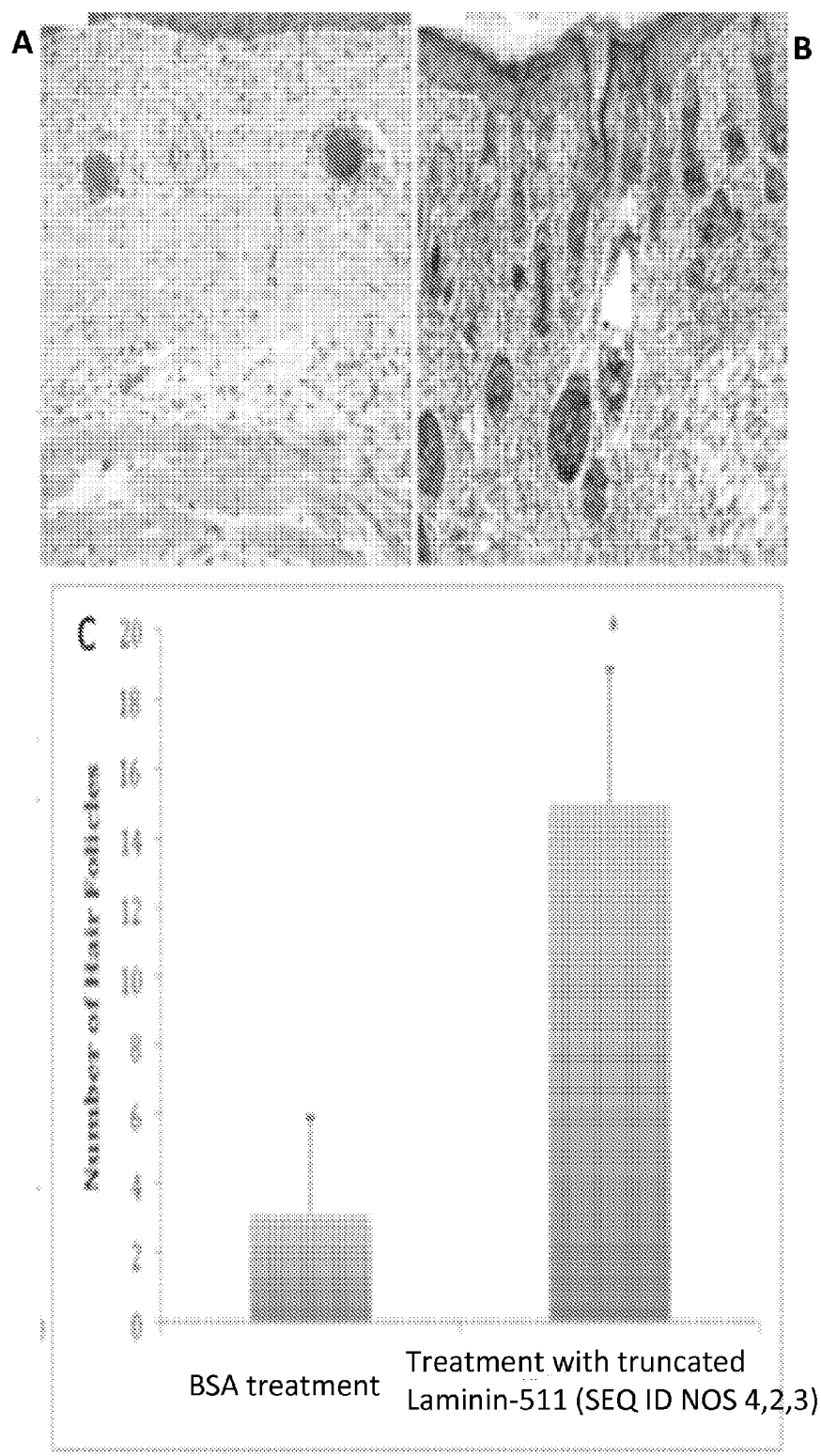
FIG. 1 illustrates that truncated, recombinant laminin-511 (trimer of SEQ ID NOS: 4, 2, 3) promotes hair growth in nude mice. Freshly isolated E16.5 lama5−/− null dorsal skin was incubated with either 80 μg/ml of truncated, recombinant laminin-511 or phosphate buffered saline (PBS) as negative control overnight at 4° C. (n=6). Soaked skin was grafted onto the back of nude mice, and skins were harvested after 9 to 12 days following grafting.

The present invention provides methods related to the use of a truncated, recombinant laminin-511 protein or peptide for modifying hair growth, based on the unexpected discovery that the full-length laminin-511 protein may be significantly reduced in size (also referred to herein as "truncated" or "truncated laminin-511") and yet retain its capability to promote hair growth and/or to reduce hair loss. The present invention, furthermore, provides methods related to the use of agents that modify the expression of the full-length laminin-511 protein or its function for decreasing hair growth in areas where hair growth is undesired.

Before describing specific embodiments of the invention, definitions are set forth that are utilized in describing the present invention.

DEFINITIONS

The practice of the present invention may employ conventional techniques of molecular biology, recombinant DNA, cell biology, immunology and biochemistry, which are within the capabilities of a person of ordinary skill in the art. Such techniques are fully explained in the literature. For definitions, terms of art and standard methods known in the art, see, for example, Sambrook and Russell 'Molecular Cloning: A Laboratory Manual', Cold Spring Harbor Laboratory Press (2001); 'Current Protocols in Molecular Biology', John Wiley & Sons (2007); William Paul 'Fundamental Immunology', Lippincott Williams & Wilkins (1999); 'Current Protocols in Cell Biology', John Wiley & Sons (2007); Wilson & Walker 'Principles and Techniques of Practical Biochemistry', Cambridge University Press (2000). Each of these general texts is herein incorporated by reference.

Unless defined otherwise, all technical and scientific terms used herein have the same meaning as commonly understood by a person of ordinary skill in the art to which this invention belongs. The following definitions are intended to also include their various grammatical forms, where applicable. As used herein, the singular forms "a" and "the" include plural referents, unless the context clearly dictates otherwise. Thus, for example, reference to a "structurally related residue" includes a combination of various residues, and the like.

The term "about", as used herein, particularly in reference to a given quantity, is meant to encompass deviations of plus or minus ten percent.

The term "therapeutic effect", as used herein, refers to a consequence of treatment in a subject, including a human, that is intended either to result in increased hair growth, in decreased hair loss or in decreased hair growth.

The therapeutic agents referred to herein encompass truncated, recombinant laminin-511 trimers, as exemplified in SEQ ID NOS 1-3; 4, 2, 3; and 5, 2, 3; their variants in accordance to sequence identity or substantial sequence identity; full-length laminin-511 trimer (SEQ ID NOS 6-8); modulators of full-length laminin-511 expression including siRNA, shRNA and antisense oligonucleotides; and modulators of full-length laminin-511 function including small molecules that affect full-length laminin-511 interaction with integrin receptors.

The term "therapeutically effective amount", as used herein, is an amount that is sufficient to provide a desired therapeutic effect in a subject, including a human. Naturally, dosage levels of the particular agent employed to provide a therapeutically effective amount vary in dependence of the type of disorder, the age, the weight, the gender, the medical condition of the subject, the severity of the condition, the route of administration, and the particular agent employed. Therapeutically effective amounts of a truncated, recombinant laminin-511 or of modulators of full-length laminin-511 expression or function, as described herein, can be estimated initially from animal models. For example, $I_{C50}$ values determined in animal models, such as in nude mice, as described herein, can be used to find a therapeutically effective dose in a subject, including a human. Schedules for administering a truncated, recombinant laminin-511, full-length laminin-511 or a modulator of full-length laminin-511 expression or function may be determined empirically, and making such determinations is within the skill in the art.

The terms "protein", "peptide" and "polypeptide" are used interchangeably and in their conventional meaning herein and relate to polymers in which the monomers are amino acids and are joined together through amide bonds. In case of optically active amino acids, both the L-isomer and the D-isomer are contemplated.

The term "recombinant", as used herein, relates to a protein or peptide that is obtained by expression in a host. A host can either be a prokaryotic host cell such as a cultivated E. coli strain or an eukaryotic host cell such as a mammalian cell or a stem cell. A host can also be a transgenic animal that expresses a truncated, recombinant laminin-511, such as a fly, worm or mouse.

The term "truncated laminin-511", as used herein, relates primarily to trimeric variants of a laminin-511 peptide or protein that are significantly reduced in size in comparison to the full-length laminin-511, yet have retained the capability of promoting hair growth. Representative amino acid sequences are shown in SEQ ID NOS 1-3; 4, 2, 3; and 5, 2, 3. Accordingly, truncated laminin-511 trimers of the present invention also include addition, substitution and deletion variants of the amino acid sequences represented in SEQ ID NOS 1-3; 4, 2, 3; and 5, 2, 3. The truncated laminin-511 proteins may be made in glycosylated or non-glycosylated forms. Variants of truncated laminin-511 protein may also involve attachment to a water soluble polymer. For example, the truncated laminin-511 proteins may be conjugated to one or more polyethylene glycol molecules to decrease the precipitation of the respective truncated laminin-511 in an aqueous environment.

The term "secondary treatment product", as used herein, relates to agents that can be administered in combination with a truncated laminin-511 or a modulator of full-length laminin-511 function or expression in order to enhance the bioavailability and/or efficacy of the laminin-511 or a modulator of full-length laminin-511 function or expression. For example, a secondary treatment product could be an absorption enhancer such as N-methyl-2-pyrrolidone or isopropylmyristate.

Yet another aspect of the present invention includes the various polynucleotides encoding truncated laminin-511 proteins. These nucleic acid sequences are generally used in the expression of truncated, recombinant laminin-511 in a eukaryotic or prokaryotic host cell, wherein the expression product or a derivative thereof is characterized by the ability to promote, i.e. to increase, hair growth and/or to decrease hair loss. A person of ordinary skill in the art will understand that truncated laminin-511 can be encoded by various nucleic acids, since each amino acid in the protein is represented by one or more sets of 3 nucleic acids (codons). Since many amino acids are represented by more than one codon, there is not a unique nucleic acid sequence that codes for a given protein. The codon systems in different organisms can be slightly different; when the expression of a given protein in a particular organism is desired, the nucleic acid sequence can be modified to be suitable for expression in that particular organism. In one embodiment, the host cell is a cultivated E. coli strain. In other embodiments, the host cell is a mammalian cell or a stem cell. In another embodiment, the host cell is a transgenic animal that expresses truncated, recombinant laminin-511, such as a fly, worm or mouse.

A further aspect of the present invention involves vectors containing the polynucleotides encoding truncated laminin-511 protein operatively linked to amplification and/or expression control sequences. Both prokaryotic and eukaryotic host cells may be stably transformed or transfected with such vectors to express the alpha-5, beta-1 and/or gamma-1 chains of a truncated laminin-511. The present invention further includes the recombinant production of a truncated laminin-511 wherein such transformed or transfected host cells are grown in a suitable nutrient medium, and the truncated laminin-511 expressed by the cells is, optionally, isolated from the host cells and/or the nutrient medium. Suitable cloning vectors include bacterial artificial chromosomes (BAC) or yeast artificial chromosomes (YAC); suitable expression vectors include viruses such as lentivirus or retrovirus. A general purpose promoter allows expression of the alpha-5, beta-1 and/or gamma-1 chains of a truncated laminin-511 in a wide variety of cell types. A promoter can also be inducible, for example, by an exogenously administered drug.

The terms "isolated" and "purified", as used herein, relate to molecules that have been manipulated to exist in a higher concentration or purer form than naturally occurring.

The term "pharmaceutically acceptable carrier", as used herein, refers to a diluent or carrier or to a mixture of diluents or carriers used in the formulation of therapeutic agents. Pharmaceutically acceptable carriers, in a pharmaceutical composition, serve to facilitate solubility, formulability, storage, handling, delivery and/or efficacy of therapeutic agents; they are pharmaceutically inert, do not cause unacceptable adverse side effects and do not prevent a therapeutic agent from exerting a therapeutic effect. Pharmaceutically acceptable carriers may be in solution or suspension, for example, incorporated into microparticles, liposomes, or cells, or embedded into an injectable, biodegradable polymer, e.g., a hydrogel, for controlled, sustained release. Examples of pharmaceutically acceptable carriers include, but are not limited to, water, saline, binding agents such as hydroxypropyl methylcellulose or polyvinylpyrrolidone, fillers such as monosaccharides, disaccharides, sugar alcohols, starch or gelatin, Ringer's solution and other suitable inert materials. The pH of the preparations can range from about pH 5 to about pH 8.5; the pharmaceutically acceptable carriers can contain pH adjusting and buffering agents or agents to adjust tonicity of the resulting pharmaceutical composition. It will be apparent to those persons skilled in the art that certain carriers may be preferable depending upon, for instance, the route of administration and concentration of composition (truncated, recombinant laminin-511, full-length laminin-511 or modulators of full-length laminin-511 expression or function) being administered.

The term "topical" or "topically", as used herein, refers to a spot, which can be in or on any part of the body, including but not limited to the epidermis, any other dermis, or any other body tissue. One particular area that is contemplated for the administration of the therapeutic agents of this application is the hair follicle bulge region. Topical administration or application means the direct contact of a therapeutic agent with tissue, such as skin which includes scalp. Methods of applying the present topical agents to the skin or scalp include liquid or semi-liquid carriers such as gels, lotions, emulsions, creams, plasters, or ointments, or non-spreading carriers which retain their form, e.g., patches, dressings and bandages. The solvents for delivery of the therapeutic agents using a microneedle device, as described in the application, are non-toxic, pharmaceutically acceptable carriers and preferably liquids. Potential solvents that are contemplated include polyhydric alcohols such as dipropylene glycol, propylene glycol, polyethylene glycol, glycerin, butylene glycol, hexylene glycol, polyoxyethylene, polypropylene glycol, sorbitol, ethylene glycol, and the like. Other suitable solvents include fatty acids such as oleic acid, linoleic acid, capric acid and the like, as well as fatty esters or alcohols. Further suitable solvents include other non-toxic, non-volatile solvents commonly used in dermal or transdermal compositions for dissolving peptide-or protein-based compositions.

Microneedles or microneedle devices, as used herein, refer to an array comprising a plurality of hollow microprojections, generally ranging from about 10 to about 2000 µm in length which are attached to a base support and which have a diameter large enough to hold a selectable volume or amount of a pharmaceutical composition comprising a therapeutic agent and a pharmaceutically acceptable carrier and to permit passage of the pharmaceutical composition for transdermal or intradermal delivery. An array may comprise a multitude of microneedles ranging in number from several to thousands and may range in area from several square millimeters to several square centimeters. In some embodiments of the invention, the microneedle array is formulated as a transdermal drug delivery patch. Microneedle arrays can be integrated with an applicator device which, upon activation, can deliver the microneedle array into the skin or scalp surface, or the microneedle arrays can be applied to the skin and the device then activated to push the microneedles through the dermal layer of the skin including the scalp.

The microneedles can be fabricated from various biodegradable or biocompatible polymers or cross-linked monomers that contain hydrolytically unstable linkages such as esters, anhydrides, orthoesters, and amides. Materials of particular interest for fabrication of the microneedles are suited for delivery of the therapeutic agent and pharmaceutical compositions comprising the therapeutic agent and encompass natural as well as synthetic materials. Natural materials may include saccharides such as galactose, maltose, dextrin and the like, while synthetic materials include polymers of α-hydroxy acids, such as lactic acid and glycolic acid, including polylactide (LPLA and DLPLA), polyglycolide (PGA), polylactide-co-glycolide, polymers of ε-caprolactone (polycaprolactones), and copolymers with polyethyleneglycol, polyanhydrides, poly(ortho)esters, polyurethanes, poly(butyric acid), poly(valeric acid), and poly(lactide-co-caprolactone). Materials may be cross-linked through ion exchange, photopolymerization and similar methods. The dose of a therapeutic agent to be delivered by a microneedle array will vary and may range from about 1 ng/microneedle array to several hundred µg/microneedle array or more.

Also provided herein are functional nucleic acids that modulate the expression or function of full-length laminin-511. Functional nucleic acids are nucleic acid molecules that have a specific function, such as binding a target molecule or catalyzing a specific reaction. Functional nucleic acid molecules can interact with any macromolecule, such as DNA, RNA, polypeptides, or carbohydrate chains. Thus, functional nucleic acids can interact with the mRNA, genomic DNA, or polypeptide. Often functional nucleic acids are designed to interact with other nucleic acids based on sequence homology between the target molecule and the functional nucleic acid molecule; in other situations, the specific recognition between the functional nucleic acid molecule and the target molecule is not based on sequence homology between the functional nucleic acid molecule and the target molecule, but rather is based on the formation of tertiary structure that allows specific recognition to take place.

Several assays are known in the art for determining full-length laminin-511 expression, such as verification of molecular weight of the expressed protein via gel electrophoresis, e.g. SDS-Page followed by staining or immunoblotting with a specific antibody, or for determining full-length laminin-511 function, such as conducting integrin binding assays, particularly with β1 integrins.

As contemplated herein, a modulator of full-length laminin-511 expression is an antisense oligonucleotide, typically up to about 50 nucleotides in length, capable of specifically binding (hybridizing) to full-length laminin-511 alpha-5 chain, beta-1 chain or gamma-1 chain sequences and reducing the expression thereof and/or preventing trimerization of the alpha-5, beta-1 and gamma-1 chains. Furthermore, a modulator of full-length laminin-511 expression is a small-interfering ribonucleic acid, typically less than about 50 nucleotides in length, capable of specifically binding (hybridizing) to laminin-511 alpha-5 chain, beta-1 chain or gamma-1 chain sequences and reducing the expression thereof and/or impeding trimerization of the alpha-5, beta-1 and gamma-1 chains. A modulator of full-length laminin-511 expression is a small hairpin ribonucleic acid, typically less than about 50 nucleotides in length, capable of specifically binding (hybridizing) to full-length laminin-511 alpha-5 chain, beta-1 chain or gamma-1 chain sequences and reducing the expression thereof and/or impeding trimerization of the alpha-5, beta-1 and gamma-1 chains.

As used herein, the term "antibody" or "antibodies" relates to both polyclonal and monoclonal antibodies, including intact immunoglobulin molecules, fragments, chimeras, or polymers of immunoglobulin molecules are also useful in the methods described herein, as long as they are chosen for their ability to detect the alpha-5, beta-1 and/or gamma-1 chain of full-length laminin-511.

Monoclonal antibodies can be made using various methods, for example, using hybridoma methods, such as described by Koehler and Milstein, 1975. In a hybridoma method, a mouse or other appropriate host animal is typically immunized with an immunizing agent to elicit lymphocytes that produce or are capable of producing antibodies that will specifically bind to the immunizing agent. Alternatively, the lymphocytes may be immunized in vitro. The monoclonal antibodies may also be made by recombinant DNA methods, such as those described in U.S. Pat. No. 4,816,567 by Cabilly et al. DNA encoding the disclosed monoclonal antibodies can be readily isolated and sequenced using conventional procedures, for example, by using oligonucleotide probes that are capable of binding specifically to genes encoding the heavy and light chains of murine antibodies.

The term "antibody" or "antibodies" also refers to a fully human antibody or a humanized, chimeric antibody. Examples of techniques for fully human monoclonal antibody production include production in transgenic animals in response to immunization (Jakobovits et al., 1993a/b; 2007) or from phage display libraries (Hoogenboom & Winter, 1992; Marks et al., 1991).

Antibody humanization techniques involve the use of recombinant DNA technology to manipulate the DNA sequence encoding one or more polypeptide chains of an antibody molecule, as well known in the art (Jones et al., 1986; Verhoeyen et al., 1988; U.S. Pat. No. 6,180,370 by Queen & Selick). Fragments of humanized antibodies, that include functional domains or effector domains, including Fv, Fab, Fab', Fc, are also useful in the methods described herein.

Polydimethylsiloxane (PDMS, dimethicone) is a silicon-based organic polymer, that is non-toxic, non-flammable and inert and, therefore, widely used in consumer products such as shampoos, adhesives, resins and silicon caulk. PDMS is viscoelastic and, depending on the surrounding temperature, possesses characteristics of both a viscous liquid and rubber. Curing, i.e. polymerization and cross-linking, gives PDMS an external hydrophobic surface.

Laminins

The laminin family of cell-adhesive glycoproteins is a major constituent of the basal lamina and forms an integral part of the structural scaffolding in a variety of cell types including epithelial, endothelial, muscle, nerve and fat cells. As basal lamina components, laminins are part of the extracellular matrix (ECM) and play critical roles in cell adhesion, signaling, migration, differentiation and survival. Laminins play also an important role in embryonic development and in the overall differentiation of epithelial cells. Laminin-511, similarly to Laminin-11, is ubiquitously expressed in all basal laminae during embryogenesis; laminin-511 deficiency results in severe developmental abnormalities involving multiple organs such as kidneys, lungs and muscles, reflecting poor physical strength of basal laminal membranes and reduced signaling events involving the integrin family (Taniguchi et al., 2009; Tzu & Marinkovich, 2008).

Laminins are composed of three different, glycosylated polypeptide chains, termed α, β and γ, which assemble into a disulfide-bonded trimer and which contain specific domains that are capable of interacting with cellular receptors such as integrins. Five α (α1-α5), four β (β1-β4), and three γ chains (γ1-γ3) have been identified in mammals (Miner and Yurchenco, 2004), giving rise to at least 15 different functional laminin isoforms (Aumailley et al., 2005). Accordingly, the full-length laminin-511 trimer contains one alpha-5 (α5), one beta-1 (β1) and one gamma-1 (γ1) chain.

Interaction of Laminins with Integrins

Integrins are heterodimeric cell surface receptors which facilitate attachment of cells to their surrounding tissues including extracellular matrix (ECM) structures such as laminins and which play an important role in cell signaling and signal transduction from the ECM to cells, involving cell growth, division, differentiation, survival or death. Integrins are vitally important to a wide range of multicellular organisms, since cell attachment to the ECM is a basic requirement to create a multicellular organism. At least eight integrins are known to interact with laminins including α1β1, α2β1, α5v1, α3β1, α6β1, α6β4, αvβ3, αvβ5, α7β1 (Burkin & Kaufman, 1999; Tzu et al., 2005). For endogenous full-length laminin-511, the main cellular integrin receptors are α3β1 and α6β1 (Tzu & Marinkovich, 2008).

The Morphogenesis of Hair Follicles and the Role of Laminin-511

In earlier work with the full-length laminin-511 molecule, the inventors of the present invention discovered that laminin-511 exerted control over hair morphogenesis, as reported by Li et al., 2003, and, with more detailed information about the mechanism of action, by Gao et al., 2008, Normal development and cycling of hair follicles occurs through the reciprocal interaction of the follicular epithelium with the mesenchymal dermal papilla (Hardy, 1992; Oro & Scott, 1998). Two key elements that control the cycling of hair follicles are the follicular epithelial stem cells in the hair follicle bulge region and the specialized mesenchymal cells that constitute the follicular papilla. The hair grows in cycles of various phases and each hair follicle continuously goes through three phases: the anagen growth phase, the catagen regressing or involuting phase and the telogen resting phase. In average, an anagen phase lasts about 2-3 years, the catagen phase about 2-3 weeks and the telogen phase about 3 months.

The dermal papilla secrets insulin-like growth factor 1 and fibroblast growth factor 7, both of which exert important roles in hair follicle development and cycling. Hormones, in particular androgens, modulate hair growth as well (Paus & Cotsarelis, 1999).

Utility of Truncated Laminin-511

The full-length laminin-511 holds the potential to support development of hair and mesenchymal stem cells (Gao et al., 2008). However, with its size of 800 kDa it is extremely expensive to be produced recombinantly and its recombinant production would not be economical on an industrial scale. The hair and stem cell promoting activity of the full-length laminin-511 is maintained in the truncated laminin-511 variants, which is sufficient to trigger hair formation and hair growth, as described in several embodiments of the invention, and to maintain the proliferating state of mesenchymal stem cells. Truncated laminin-511 variants, as described herein, have low molecular weight and can be easily produced recombinantly on a commercial scale. Truncated laminin-511 has utility in promoting hair growth in a range of clinical hair loss disorders such as alopecia and in promoting the growth of mesenchymal stem cells during tissue regeneration.

General Methods and Materials for Making and Using the Invention

Truncated, Recombinant Laminin-511 Variants with Sequence Identity or Substantial Sequence Identity Truncated, recombinant laminin-511 trimers comprising protein sequences according to SEQ ID NOS:1-3; 4, 3, 2; and 5, 3, 2, as contemplated herein, include variants of sequence identity or substantial sequence identity with deletions, additions or mutations of single amino acids in the alpha-5 chain, beta-1 chain and/or gamma-1 chain of such trimers, while retaining the capability of promoting hair growth in a mammalian subject. Such deletions, additions or mutations can affect as little as one amino acid or several amino acids in the alpha-5 chain, beta-1 chain and/or gamma-1 chain.

Such variants that contain amino acid substitutions, deletions or insertions are ordinarily prepared by site specific mutagenesis of nucleotides in the DNA encoding alpha-5, beta-1 and/or gamma-1 chains of laminin-511 to produce DNA encoding the variant and thereafter expressing the DNA in recombinant cells, cell culture or transgenic animals. Amino acid substitutions are typically of single residues and insertions/additions can be in the order from about 1 to 20 non-natural or natural amino acids. Similarly, deletions may range from about 1 to 20 amino acids.

Additionally or alternatively, the alpha-5 chain, beta-1 chain and/or gamma-1 chain of those truncated, recombinant laminin-511 trimers might be modified through deletions, additions or substitutions of single amino acids to increase stability, solubility, bioavailability and so forth. Such deletions, additions or mutations can affect as little as one amino acid or several amino acids in the alpha-5 chain, beta-1 chain and/or gamma-1 chain. Exemplary substitutions of single amino acids might be conservative substitutions with structurally related amino acids.

The term "sequence identity" in the context of two amino acid sequences refers to the residues in the two sequences, which are the same when aligned for maximum correspondence. Optimal alignment of sequences for comparison can be conducted, e.g., by the local homology algorithm of Smith & Waterman, 1981; by the homology alignment algorithm of Needleman & Wunsch, 1970; by the search for similarity method of Pearson & Lipman, 1988; by computerized implementations of these algorithms (GAP, BESTFIT, FASTA, and TFASTA in the Wisconsin Genetics Software Package, Genetics Computer Group, 575 Science Dr., Madison, Wis.), or by inspection. Sequence identity may be calculated on the basis of residues identical to a reference sequence. For example, for a peptide with 8 residues, one may create a peptide variant with 5 identical residues, resulting in a 5/8 or 63% sequence identity. One may also have 6/8 (75%) or 7/8 (88%) sequence identity.

The terms "substantial sequence identity" or "substantial identity", as used herein, denote a characteristic of an amino acid sequence, wherein the peptide or protein comprises a sequence that has at least 60 percent sequence identity, at least 65 percent sequence identity, at least 70 percent sequence identity, at least 75 percent sequence identity, at least 80 percent sequence identity, preferably at least 85 percent identity and often 90 to 95 percent sequence identity, more usually at least 99 percent sequence identity as compared to a reference sequence over a comparison window of the entire length of the peptide or protein. Substantial identity also includes conservative amino acid substitutions.

Conservative amino acid substitutions are substitutions that take place within a family of amino acids that are related in their side chains and so share structurally related residues. Genetically encoded amino acids are generally divided into families: (1) acidic=aspartate, glutamate; (2) basic=lysine, arginine, histidine; (3) non-polar=alanine, valine, leucine, isoleucine, proline, phenylalanine, methionine, tryptophan; and (4) uncharged polar=glycine, asparagine, glutamine, cysteine, serine, threonine, tyrosine. Thus, aspartate and glutamate share structurally related residues; lysine, arginine and histidine share structurally related residues; alanine, valine, leucine, isoleucine, proline, phenylalanine, methionine, and tryptophan share structurally related residues; glycine, asparagine, glutamine, cysteine, serine, threonine and tyrosine share structurally related residues; and so forth. Preferred families: serine and threonine are an aliphatic-hydroxy family; asparagine and glutamine are an amide-containing family; alanine, valine, leucine and isoleucine are an aliphatic family; phenylalanine, tryptophan, and tyrosine are an aromatic family, and cysteine and methionine are a sulfur-containing side chain family. For example, it is reasonable to expect that an isolated replacement of a leucine with an isoleucine or a valine, an aspartate with a glutamate, a threonine with a serine, or a similar replacement of an amino acid with a structurally related amino acid in either the alpha-5, beta-1 and/or gamma-1 chain of a truncated laminin-511 will not have a major effect on the hair-promoting characteristics of the resulting molecule, especially if the replacement does not involve an amino acid within a framework site. Preferred conservative amino acid substitution groups are: valine-leucine-isoleucine, phenylalanine-tyrosine, lysine-arginine, alanine-valine, glutamic acid-aspartic acid, cysteine-methionine, and asparagine-glutamine.

In making such changes, the hydropathic index of amino acids may be considered. The importance of the hydropathic amino acid index in conferring interactive biologic function on a protein is generally understood in the art (Kyte and Doolittle, 1982). It is generally accepted that the relative hydropathic character of the amino acid contributes to the secondary structure of the resultant protein, which in turn defines the interaction of the protein with other molecules, for example, enzymes, substrates, receptors, DNA, antibodies, antigens, and the like. Each amino acid has been assigned a hydropathic index on the basis of its hydrophobicity and charge characteristics (Kyte and Doolittle, 1982), as follows: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5).

In modifying the presently exemplified sequences (SEQ ID NOS 1-3; 4, 2, 3; and 5, 2, 3), certain amino acids may be substituted by other amino acids having a similar hydropathic index or score and still result in a protein with similar biological activity, i.e., still obtain a biological functionally equivalent protein. In making such changes, the substitution of amino acids whose hydropathic indices are within ±2 is preferred, those that are within ±1 are particularly preferred, and those within ±0.5 are even more particularly preferred.

Substitution of like amino acids can also be made effectively on the basis of hydrophilicity. U.S. Pat. No. 4,554,101, incorporated herein by reference, states that the greatest local average hydrophilicity of a protein, as governed by the hydrophilicity of its adjacent amino acids, correlates with a biological property of the protein. As detailed in U.S. Pat. No. 4,554,101, the following hydrophilicity values have been assigned to amino acid residues: arginine (+3.0); lysine (+3.0); aspartate (+3.0±1); glutamate (+3.0±1); serine (+0.3); asparagine (+0.2); glutamine (+0.2); glycine (0); threonine (−0.4); proline (−0.5±1); alanine (−0.5); histidine (−0.5); cysteine (−1.0); methionine (−1.3); valine (−1.5); leucine (−1.8); isoleucine (−1.8); tyrosine (−2.3); phenylalanine (−2.5); tryptophan (−3.4).

In modifying the presently exemplified sequences (SEQ ID NOS 1-3; 4, 2, 3; and 5, 2, 3), amino acid substitutions may also be generally based on the relative similarity of the amino acid side-chain substituents, for example, their hydrophobicity, hydrophilicity, charge, size, and the like but may nevertheless be made to highlight a particular property of the peptide. Exemplary substitutions that take various of the foregoing characteristics into consideration are well known to those of skill in the art and include: arginine and lysine, which, with histidine, are basic at physiological pH; glutamate and aspartate, which are acidic; serine and threonine; glutamine and asparagine; valine, leucine and isoleucine.

Truncated Laminin-511

The minimal portion of functional integrin binding activity on laminin-511 is a fragment, discovered by early pepsin digestion studies, termed laminin-511 E8. This portion of the molecule contains a 225 amino acid (Leu1561-Leu1786), approximately 30 kDa portion, of the laminin-511 beta-1 chain (SEQ ID NO:2) and a 245 amino acid (Asn1364-Pro1609), approximately 33 kDa, portion of the laminin-511 gamma-1 chain (SEQ ID NO:3).

Earlier studies by the inventors of the present invention proved that a 35 kDa deletion of the alpha-5 chain at its C-terminus (G4/5 domains), yielding the C-terminal 788 amino acids (Ala2534-3322) portion of the laminin-511 alpha-5 chain (SEQ ID NO:4) did not affect its integrin binding (Gao et al., 2008).

In one embodiment of the present invention, the truncated laminin-511 is a trimer comprising the amino acid sequences of SEQ ID NOS 1, 2 and 3 (see Tables 1-3). In other embodiments, truncated laminin-511 is a trimer comprising SEQ ID NOS 4, 2, 3 (see Tables 2, 3 and 4) or 5, 2, 3 (see Tables 2, 3, and 5).

Protein Expression Systems for Expressing Truncated, Recombinant Laminin-511

Protein expression systems are systems specifically designed for the transcription of a nucleic acid of choice into messengerRNA (mRNA) and subsequent translation of that mRNA into a protein. Herein, a fusion protein is also contemplated that comprises a truncated, recombinant laminin-511 coupled to another functional protein, for example, for the purpose of facilitating expression of truncated laminin-511, for enhancing the therapeutic or pharmacokinetic properties of truncated laminin-511 or for facilitating detection of the expression of truncated laminin-511. Examples of fusion partners include but are not limited to human or bovine serum albumin, therapeutic agents, cytotoxic molecules, radionucleotides, fluorescent proteins and so forth.

Following expression, truncated, recombinant laminin-511 is purified or isolated. Truncated laminin-511 may be isolated or purified in various ways known to those skilled in the art. Standard purification techniques include electrophoretic, molecular, immunological and chromatographic techniques, including ion exchange, hydrophobic, affinity and reverse-phase high-performance liquid chromatography (HPLC), and chromatofocusing.

E. coli Expression Systems. *Escherichia coli* (*E. coli*) is one of the most widely used and best characterized hosts for the production of heterologous, non-glycosylated proteins, particularly for the large-scale, cost-effective manufacturing of recombinant proteins. It is contemplated that recombinant, truncated laminin-511 can be expressed in a variety of *E. coli* expression vectors, possibly with the use of fusion proteins or expression tags to enhance solubility of the resulting protein, if needed.

Yeast Expression Systems. Yeast expression systems provide the additional capability of post-translational modification, so they are suited for the expression of glycosylated proteins.

Mammalian Cell Expression Systems. Proteins for human therapies, vaccinations or diagnostic applications are predominantly produced in mammalian cell expression systems.

Viral Expression Systems. Viral vectors encompass baculoviruses, retroviruses including lentiviruses, adenoviruses and phages. Lentiviruses are a special type of retrovirus and capable of infecting all types of human cells, they are often used to create stable, continuously proliferating cell lines given the appropriate medium.

Methods of Treatment

Conditions of interest for treatment with a truncated, recombinant laminin-511 in accordance to the methods of the present invention include, without limitation, cases of androgenic alopecia, such as male pattern baldness as well as female pattern baldness, and other hair loss disorders, all in which the hair follicles have maintained their cycling transformation capability. Furthermore, the methods of the present invention address conditions of unwanted hair overgrowth, such as hirsutism or hypertrichosis, or unwanted hair growth for cosmetic reasons on legs, arms etc. by decreasing hair growth using modulators of full-length laminin-511 expression or function.

One aspect of the present invention is a method for treating a subject, who is suffering from a hair loss disorder, by administering a therapeutically effective amount of a truncated, recombinant laminin-511 with a suitable pharmaceutical carrier. In various embodiments, a therapeutically effective amount of a truncated, recombinant laminin-511 is administered to the skin, particularly the scalp and more particularly to the hair follicle bulge region, of a subject topically, subcutaneously or intradermally, preferably with a microneedle array delivery device. In an alternative embodiment, truncated, recombinant laminin-511 is embedded into an injectable, biodegradable hydrogel and implanted subcutaneously or intradermally for sustained, controlled release of therapeutically effective amounts, particularly to the hair follicle bulge region.

Another aspect of the present invention is a method for treating a subject, who is suffering from a hair overgrowth disorder, by administering a therapeutically effective amount of a modulator of full-length laminin-511 expression or function. In various embodiments, a therapeutically effective amount of a modulator of full-length laminin-511 expression or function is administered to the skin, particularly the scalp and more particularly to the hair follicle bulge region, of a subject topically, subcutaneously or intradermally, preferably with a microneedle array delivery device. Alternatively, a modulator of full-length laminin-511 expression or function is embedded into an injectable, biodegradable hydrogel, implanted subcutaneously or intradermally for sustained, controlled release of therapeutically effective amounts.

Gene expression can effectively be silenced in a highly specific manner through ribonucleic acid (RNA) interference (RNAi). Short Interfering RNAs (siRNAs) are double-stranded RNA that can induce sequence-specific post-transcriptional gene silencing, thereby decreasing or even inhibiting gene expression. In one aspect, an siRNA triggers the specific degradation of homologous RNA molecules, such as mRNAs, within the region of sequence identity between both the siRNA and the target RNA, sequence specific gene silencing can be achieved in mammalian cells using synthetic, short double-stranded RNAs that mimic siRNAs produced by the enzyme dicer. siRNA can be chemically or in vitro-synthesized or can be the result of short double-stranded hairpin-like RNAs (shRNAs) that are processed into siRNAs inside the cell.

Antisense oligonucleotides are designed to interact with a target nucleic acid molecule through either canonical or non-canonical base pairing. The interaction of the antisense oligonucleotide and the target molecule is designed to promote the destruction of the target molecule through RNA-DNA hybrid degradation. Alternatively, the antisense oligonucleotide is designed to interrupt a processing function that normally would take place on the target molecule, such as transcription or replication. Antisense oligonucleotides can be designed based on the sequence of the target molecule. Various methods for optimization of antisense efficiency by finding the most accessible regions of the target molecule are known in the art.

Administration of Truncated, Recombinant Laminin-511

Truncated, recombinant laminin-511 can be administered for the treatment of clinical hair growth disorders in various ways. Preferred ways of administration are topically on the scalp or by subcutaneous or intradermal injection. Systemic delivery of truncated laminin-511 is also contemplated. Intradermal delivery of truncated, recombinant laminin-511 can be effected, for example, using microneedles in various assemblies and arrays. In one embodiment of the present invention, an assembly of microneedles is placed on the scalp and pressure is applied for a predetermined time, for example 30 or 60 seconds, to facilitate microneedle insertion. The assembly of microneedles can then remain in place for another predetermined time, such as 1, 2, 3, 4, 5 minutes or more, and is designed to deliver a therapeutically effective amount for either increasing hair growth or decreasing hair loss, or for decreasing hair growth.

In another aspect of the present invention, a truncated, recombinant laminin-511 can be embedded in an injectable, biodegradable polymer for controlled, sustained release. For example, truncated, recombinant laminin-511 can be embedded into an injectable, biodegradable hydrogel with a narrow transition point between liquid and hydrogel, and the hydrogel implanted subcutaneously or intradermally.

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible. In the following, experimental procedures and examples will be described to illustrate parts of the invention.

EXPERIMENTAL PROCEDURES

The following methods and materials were used in the examples that are described further below.

Exogenous proteins and hair rescuing assay. Truncated, recombinant laminin-511 (trimer of SEQ ID NOS: 4, 2, 3) was obtained from Dr. Kiyotoshi Sekiguchi from Japan (Osaka, Japan). As described (Li et. al, 2003), freshly isolated E16.5 lama5−/− null dorsal skin was incubated with either 80 μg/ml of truncated, recombinant laminin-511 or PBS as negative control overnight at 4° C. (n=6). Soaked skin was grafted onto the back of nude mice, and skins were harvested after 9 to 12 days.

Synchronization of Hair Cycle by Depilation-Induced Anagen Induction. 7-week-old mice were ordered by Stanford ARF. Briefly, on day 0, mice were anesthetized, and then a wax and rosin mixture was applied to the dorsal skin of mice with all hair follicles in telogen phase, as evidenced by the pink back skin color. Peeling off the wax/rosin mixture removed all hair shafts and immediately induced homogeneous anagen development over the entire depilated back skin area of the mouse, thus inducing a highly synchronized anagen development.

Pharmacological manipulations in vivo. Full-length laminin-511 was purchased from BioLamina (Solna, Sweden); 200 μl of Affi-gel blue beads (Bio-Rad, Hercules, Calif.; 100 μm in diameter) were soaked with 200 μl of BSA (control) or 200 μl of 100 μg/ml of full-length laminin-511. Beads were then injected into the back skin of mice, with all hair follicles in the telogen stage (n=6 for the control group and n=6 for the group treated with full-length laminin-511), as identified by their pink back skin color. 50 μl of laminin-511 in a concentration of 100 μg/ml was injected intradermally every day post-injection for 5 days. Skin was harvested on day 7 after the last injection, when all depilated control hair follicles had reached the late anagen phase.

Chemotherapy-induced alopecia (CIA) model and treatment with full-length laminin-511 (trimer of SEQ ID NOS: 6-8). The back skin of C57BL/6 mice was depilated to induce late anagen phase VI. Mice received a single IP dose of 120 mg/kg cyclophosphamide (CYP) 9 days after depilation to reproduce alopecia. Mice were euthanized for macroscopic and microscopic tests at selected time points between days 10 and 32 following anagen induction. Quantitative histomorphometry was performed on Giemsa-stained 8 μm formalin-fixed, paraffin-embedded sections, which were taken from defined back skin regions of different hair cycle stages. The degree of hair follicle (HF) dystrophy was evaluated using recently defined morphologic guidelines for classifying hair follicle dystrophy (Hendrix et al., 2005). Mice were treated with full-length laminin-511 starting 1 day before CYP injection, once daily for 5 days. Assessments of hair loss, HF cycling and HF dystrophy were performed according to the beforementioned morphologic guidelines for classifying hair follicle dystrophy.

Statistical methods. Data from in vitro and in vivo experiments are expressed as the mean±SD of at least triplicate determinations. Statistical comparisons were performed by Student's t test, and differences were considered significant at $P<0.05$.

EXAMPLES

The following examples are put forth so as to provide those of ordinary skill in the art with a complete disclosure and description of how to make and use the present invention; they are not intended to limit the scope of what the inventors regard as their invention. Unless indicated otherwise, part are parts by weight, molecular weight is average molecular weight, temperature is in degrees Centigrade, and pressure is atmospheric or near atmospheric.

Example 1

Localization of Hair Promoting Domain in Truncated, Recombinant Laminin-511

The truncated, recombinant laminin-511 trimer of SEQ ID NOS: 4, 2, 3 was tested in developing embryonic skin at embryonic day E16.5 in wildtype and laminin-511 deficient mice (lama5−/− null) for its ability to rescue hair formation and to promote hair growth.

As described (Li et al., 2003), freshly isolated E16.5 lama5−/− null dorsal skin was incubated with either 80 μg/ml truncated, recombinant laminin-511 or phosphate buffered saline (PBS) as negative control overnight at 4° C. (n=6). Soaked skin was grafted onto the back of nude mice, skins were harvested after 9-12 days and hair follicles in the skins were counted in hematoxylin and eosin stain (H & E).

As observable in FIGS. 1B and 1C, the number of hair follicles was significantly increased in lama5−/− null skin that had been treated with truncated, recombinant laminin-511 versus treatment with PBS or BSA as negative control (FIG. 1A), indicating that truncated laminin-511 was active, on a qualitative basis, in promoting significant hair growth in the mouse xenograft compared to the untreated group.

Example 2

Full-Length Laminin-511 Promotes Hair Growth in Mice

Figure 2:
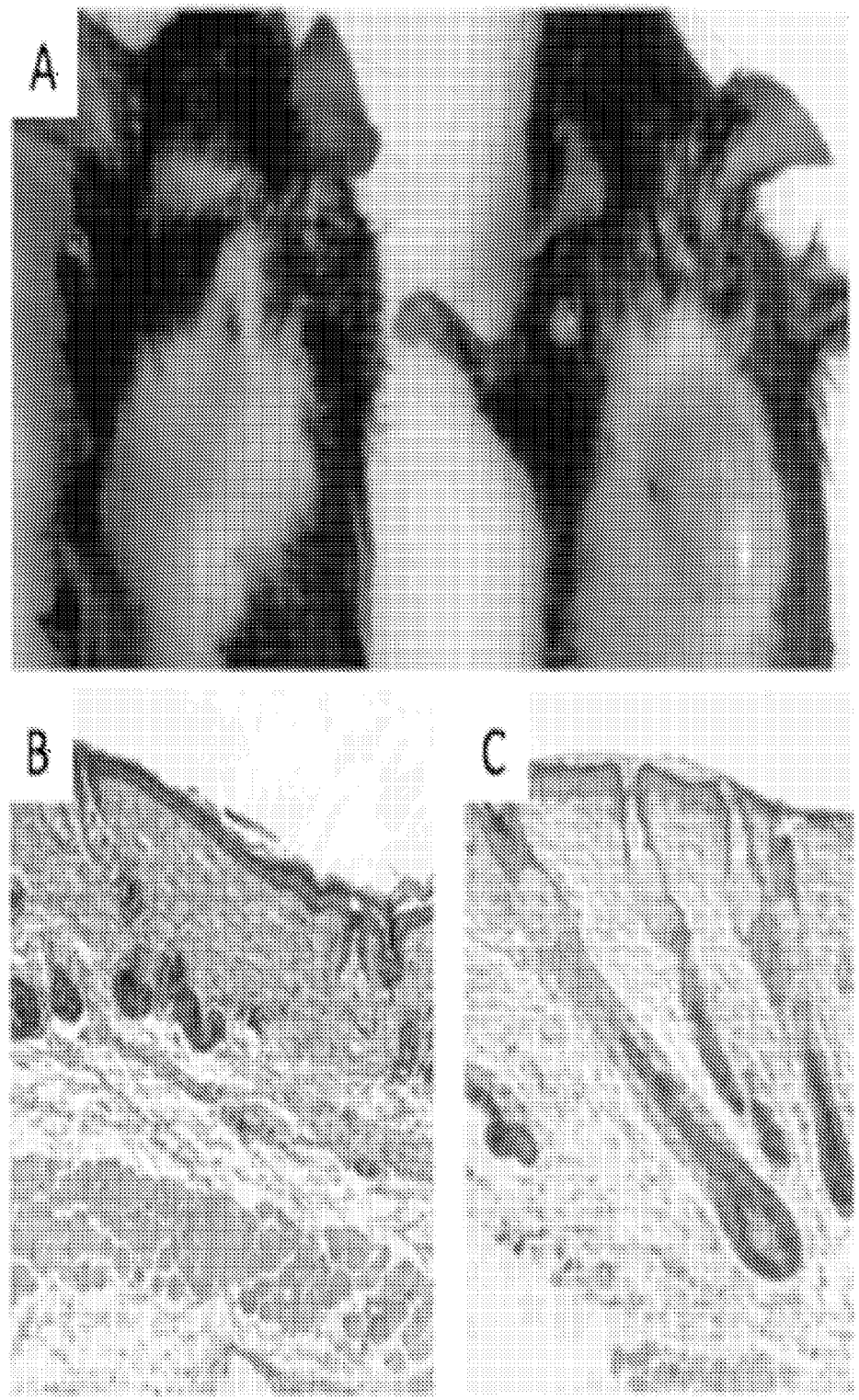
FIG. 2 illustrates that the full-length laminin-511 trimer (SEQ ID NOS:6-8) promotes hair growth when injected during the early growth (anagen) phase in the hair cycle. Anagen phase was induced by depilation. 200 μA of Affigel blue beads (Bio-Rad, Hercules, Calif.; 100 um in diameter) were soaked with 200 μA of bovine serum albumin (BSA, as control) or 200 μl of 100 μg/ml full-length laminin-511 trimer, and injected daily for 7 days into the back skin of mice. Skin was harvested on day 7 following the last injection, when all depilated control hair follicles had reached the late anagen phase. Skin areas that were treated with full-length laminin-511 showed significantly darkened skin (A right, and C), compared with the control group (A left, and B), which was indicative of increased hair follicle formation and hair growth.

Full-length laminin-511 (trimer of SEQ ID NOS:6-8) was found to be active, on a qualitative basis, in promoting significant hair growth in normal mouse skin, when injected daily for one week, following depilation (FIG. 2A right, and 2C) compared with a PBS-treated control group (FIG. 2A left, and 2B, left).

Figure 3:
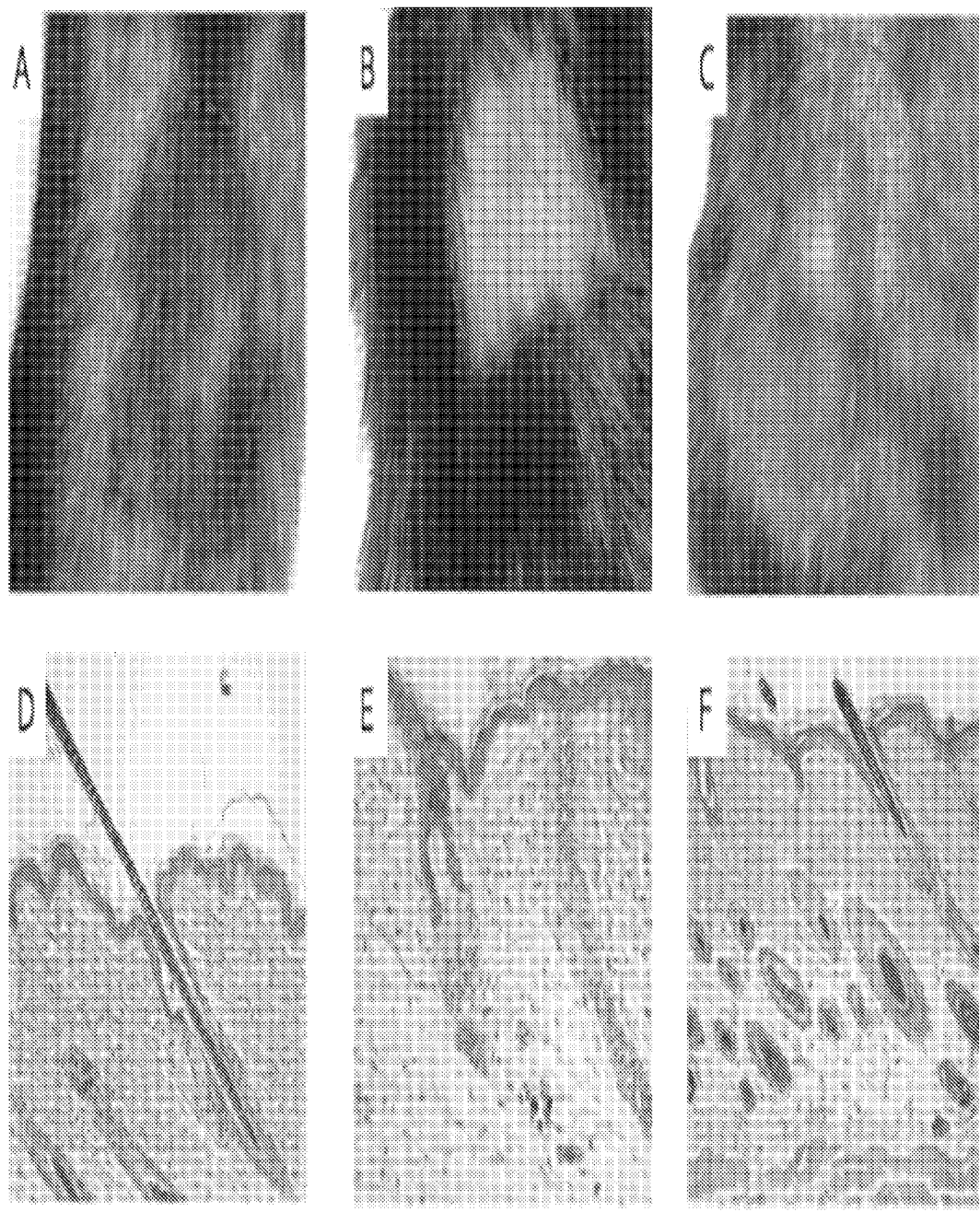
FIG. 3 illustrates the effect of full-length laminin-511 trimer (SEQ ID NOS:6-8) on pathologic hair follicle cycling in a mouse model of chemotherapy-induced alopecia (CIA). The back skin of C57BL/6 mice was depilated to induce early anagen hair cycle and mice were given a single IP dose of 120 mg/kg cyclophosphamide (CYP) 9 days after depilation to reproduce alopecia. Mice were euthanized at selected time points between days 10 and 32 following anagen induction. Gross picture (A) and H&E-stained section of control mice (D) showed complete hair growth, hair in the CYP treated mice (B, and E) was at the dystrophic catagen stage, while mice that were treated with the full-length laminin-511 trimer demonstrated clearly visible hair growth (C and F).
Figure 4:
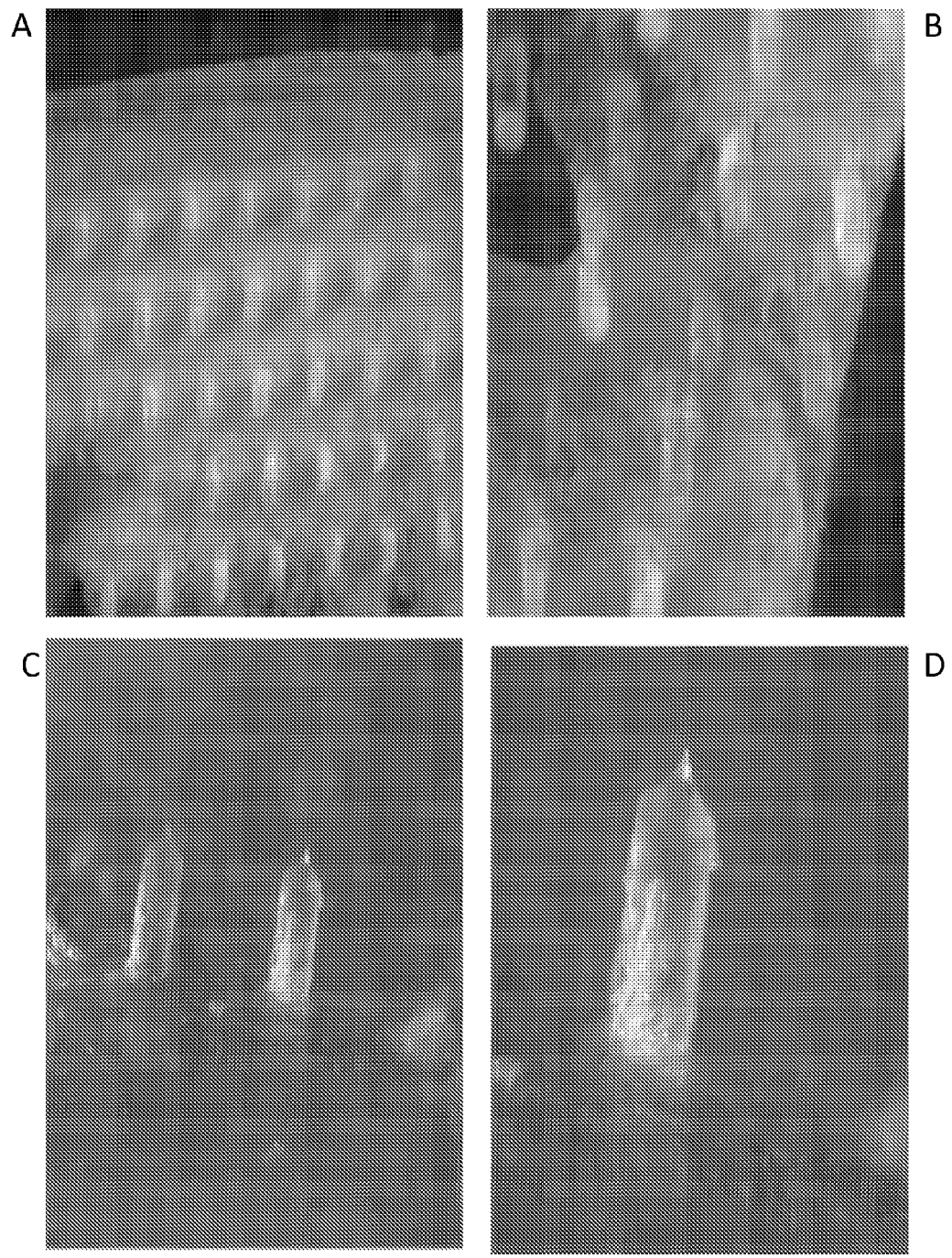
FIG. 4 shows microscopic images of PVP/mannitol microneedles with 1% lectin.

Next, the effect of full-length laminin-511 was tested following chemotherapy-induced alopecia (CIA). The back skin of C57BL/6 mice was depilated to induce early anagen hair cycle, and mice were given a single IP dose of 120 mg/kg cyclophosphamide (CYP) 9 days after depilation to reproduce alopecia. The mice reached complete baldness in average about 7 days after CYP injection, and were treated with PBS or full-length laminin-511 once daily for 7 days. Fourteen days after CYP injection (i.e. at the end of the laminin-511 7-day treatment), control normal mice that were depilated without CYP treatment showed complete hair growth (FIG. 3 A, D), hair in the CYP-treated mice was at dystrophic catagen stage (FIG. 3 B, E), while full length laminin-5,1-treated mice demonstrated hair growth (FIG. 3 C, F) much faster than the vehicle-only treated control group (FIG. 3 A, D).

Example 3

Preparation of Polydimethylsiloxane (PDMS) Mold

In one embodiment, molds for the microneedle devices of the present invention were fabricated as follows: a silicon wafer with oxide mask was patterned using standard contact lithographic techniques with thick photoresist and subjected to deep reactive ion etching. Residual photoresist was removed by oxygen plasma and the wafers were washed in sulfuric acid. To facilitate easy removal of molded materials, all wafers were silanized overnight in a vacuum chamber prior to use.

To prepare PDMS molds, PDMS monomer and curing agent (10:1 w/w, Dow Corning, Midland, Mich.) were mixed and poured onto silicon (Si)-wafers in a sterile Petri dish. To remove bubbles of trapped air, vacuum was applied for 20-30 min and the Petri dishes were gently rapped. To cure the PDMS, the Petri dish was incubated in a warm room (37° C.) overnight.

Example 4

Preparation of Protein Microneedles Arrays

In one embodiment of the present invention, 400 mg of 10 kD polyvinyl pyrolidone (PVP) and 200 mg of mannitol were dissolved in 2.5 mL of MQ filtered water (Milli-Q, Millipore). 6 mg of protein (Lectin from *Triticum* vulgaris (wheat)) was added to the resulting solution. The protein was stirred at 4° C. for 2 hours (Taieb et al., 2012).

A 1.5 cm×1.5 cm PDMS mold was drop cast with 100 μL of the above PVP/mannitol/lectin mixture. The mold was placed under vacuum for 5 min to remove the micro bubbles and stamped with steel needle array to remove micro bubbles. This process was repeated 5 times. The PDMS patch was then dried for 8 hrs. After that, 75 μL of the PVP/mannitol/lectin mixture was added. The resulting film was carefully peeled off the mold after 24 hrs.

Each microneedle has a textured surface and is sharp. The microneedles were stable at room temperature, retained its sharpness and texture in open atmosphere for several hours. The stability of the microneedles allows sufficient handing time in an open environment, which is important for its use for topical administration of the laminin-511 peptide trimers, as described infra.

TABLES

TABLE 1 depicting SEQ ID NO: 1, which is the amino acid sequence
of the truncated laminin-511 alpha-5 chain that contains
both G4 and G5 domains:
Amino acid sequence of the C-terminal 1161 amino acids
(Ala2534-Ala3695) of the laminin-511 alpha-5 chain

```
          2540       2550       2560       2570       2580
                AAEDAAG QALQQADHTW ATVVRQGLVD RAQQLLANST ALEEAMLQEQ 2590       2600       2610       2620       2630       2640
QRLGLVWAAL QGARTQLRDV RAKKDQLEAH IQAAQAMLAM DTDETSKKIA HAKAVAAEAQ 2650       2660       2670       2680       2690       2700
DTATRVQSQL QAMQENVERW QGQYEGLRGQ DLGQAVLDAG HSVSTLEKTL PQLLAKLSIL 2710       2720       2730       2740       2750       2760
ENRGVHNASL ALSASIGRVR ELIAQARGAA SKVKVPMKFN GRSGVQLRTP RDLADLAAYT 2770       2780       2790       2800       2810       2820
ALKFYLQGPE PEPGQGTEDR FVMYMGSRQA TGDYMGVSLR DKKVHWVYQL GEAGPAVLSI 2830       2840       2850       2860       2870       2880
DEDIGEQFAA VSLDRTLQFG HMSVTVERQM IQETKGDTVA PGAEGLLNLR PDDFVFYVGG 2890       2900       2910       2920       2930       2940
YPSTFTPPPL LRFPGYRGCI EMDTLNEEVV SLYNFERTFQ LDTAVDRPCA RSKSTGDPWL 2950       2960       2970       2980       2990       3000
TDGSYLDGTG FARISFDSQI STTKRFEQEL RLVSYSGVLF FLKQQSQFLC LAVQEGSLVL 3010       3020       3030       3040       3050       3060
LYDFGAGLKK AVPLQPPPPL TSASKAIQVF LLGGSRKRVL VRVERATVYS VEQDNDLELA 3070       3080       3090       3100       3110       3120
DAYYLGGVPP DQLPPSLRRL FPTGGSVRGC VKGIKALGKY VDLKRLNTTG VSAGCTADLL 3130       3140       3150       3160       3170       3180
VGRAMTFHGH GFLRLALSNV APLTGNVYSG FGFHSAQDSA LLYYRASPDG LCQVSLQQGR 3190       3200       3210       3220       3230       3240
VSLQLLRTEV KTQAGFADGA PHYVAFYSNA TGVWLYVDDQ LQQMKPHRGP PPELQPQPEG 3250       3260       3270       3280       3290       3300
PPRLLLGGLP ESGTIYNFSG CISNVFVQRL LGPQRVFDLQ QNLGSVNVST GCAPALQAQT 3310       3320       3330       3340       3350       3360
PGLGPRGLQA TARKASRRSR QPARHPACML PPHLRTTRDS YQFGGSLSSH LEFVGILARH 3370       3380       3390       3400       3410       3420
RNWPSLSMHV LPRSSRGLLL FTARLRPGSP SLALFLSNGH FVAQMEGLGT RLRAQSRQRS 3430       3440       3450       3460       3470       3480
RPGRWHKVSV RWEKNRILLV TDGARAWSQE GPHRQHQGAE HPQPHTLFVG GLPASSHSSK
```

TABLE 1-continued depicting SEQ ID NO: 1, which is the amino acid sequence of the truncated laminin-511 alpha-5 chain that contains both G4 and G5 domains:
Amino acid sequence of the C-terminal 1161 amino acids (Ala2534-Ala3695) of the laminin-511 alpha-5 chain

```
         3490       3500       3510       3520       3530       3540
    LPVTVGFSGC VKRLRLHGRP LGAPTRMAGV TPCILGPLEA GLFFPGSGGV ITLDLPGATL 3550       3560       3570       3580       3590       3600
    PDVGLELEVR PLAVTGLIFH LGQARTPPYL QLQVTEKQVL LRADDGAGEF STSVTRPSVL 3610       3620       3630       3640       3650       3660
    CDGQWHRLAV MKSGNVLRLE VDAQSNHTVG PLLAAAAGAP APLYLGGLPE PMAVQPWPPA 3670       3680       3690
    YCGCMRRLAV NRSPVAMTRS VEVHGAVGAS GCPAA
```

TABLE 2 depicting SEQ ID NO: 2, which is the amino acid sequence of the truncated laminin-511 beta-1 chain:
Amino acid sequence of the 225 amino acids (Leu1561-Leu1786), approximately 30 kDa portion, of the laminin-511beta-1 chain

```
1561   1570       1580       1590       1600       1610       1620
LQHSAADIAR AEMLLEEAKR ASKSATDVKV TADMVKEALE EAEKAQVAAE KAIKQADEDI 1630       1640       1650       1660       1670       1680
QGTQNLLTSI ESETAASEET LFNASQRISE LERNVEELKR KAAQNSGEAE YIEKVVYTVK 1690       1700       1710       1720       1730       1740
QSAEDVKKTL DGELDEKYKK VENLIAKKTE ESADARRKAE MLQNEAKTLL AQANSKLQLL 1750       1760       1770       1780
KDLERKYEDN QRYLEDKAQE LARLEGEVRS LLKDISQKVA VYSTCL
```

TABLE 3 depicting SEQ ID NO: 3, which is the amino acid sequence of the truncated Laminin-511 gamma-1 chain:
Amino acid sequence of the 245 amino acid (Asn1364-Pro1609), approximately 33 kDa portion, of the laminin-511 gamma-1 chain

```
                                  1364   1370       1380
                                     NDILNNL KDFDRRVNDN 1390       1400       1410       1420       1430       1440
KTAAEEALRK IPAINQTITE ANEKTREAQQ ALGSAAADAT EAKNKAREAE RIASAVQKNA 1450       1460       1470       1480       1490       1500
TSTKAEAERT FAEVTDLDNE VNNMLKQLQE AEKELKREQD DADQDMMMAG MASQAAQEAE 1510       1520       1530       1540       1550       1560
INARKAKNSV TSLLSIINDL LEQLGQLDTV DLNKLNEIEG TLNKAKDEMK VSDLDRKVSD 1570       1580       1590       1600
LENEAKKQEA AIMDYNRDIE EIMKDIRNLE DIRKTLPSGC FNTPSIEKP
```

TABLE 4 depicting SEQ ID NO: 4, which is the amino acid sequence of the truncated laminin-511 alpha-5 chain that lacks the G4 and G5 domains:
Amino acid sequence of the C-terminal 788 amino acids (Ala2534-3322), approximately 110 kDa portion, of the laminin-511 alpha-5 chain

```
    2534       2540       2550       2560       2570       2580
        AAEDAAG QALQQADHTW ATVVRQGLVD RAQQLLANST ALEEAMLQEQ
```

TABLE 4-continued depicting SEQ ID NO: 4, which is the amino acid sequence of the truncated laminin-511 alpha-5 chain that lacks the G4 and G5 domains:
Amino acid sequence of the C-terminal 788 amino acids (Ala2534-3322), approximately 110 kDa portion, of the laminin-511 alpha-5 chain

|  |  |  |  |  |  |
|---|---|---|---|---|---|
| 2590 | 2600 | 2610 | 2620 | 2630 | 2640 |
| QRLGLVWAAL | QGARTQLRDV | RAKKDQLEAH | IQAAQAMLAM | DTDETSKKIA | HAKAVAAEAQ |
| 2650 | 2660 | 2670 | 2680 | 2690 | 2700 |
| DTATRVQSQL | QAMQENVERW | QGQYEGLRGQ | DLGQAVLDAG | HSVSTLEKTL | PQLLAKLSIL |
| 2710 | 2720 | 2730 | 2740 | 2750 | 2760 |
| ENRGVHNASL | ALSASIGRVR | ELIAQARGAA | SKVKVPMKFN | GRSGVQLRTP | RDLADLAAYT |
| 2770 | 2780 | 2790 | 2800 | 2810 | 2820 |
| ALKFYLQGPE | PEPGQGTEDR | FVMYMGSRQA | TGDYMGVSLR | DKKVHWVYQL | GEAGPAVLSI |
| 2830 | 2840 | 2850 | 2860 | 2870 | 2880 |
| DEDIGEQFAA | VSLDRTLQFG | HMSVTVERQM | IQETKGDTVA | PGAEGLLNLR | PDDFVFYVGG |
| 2890 | 2900 | 2910 | 2920 | 2930 | 2940 |
| YPSTFTPPPL | LRFPGYRGCI | EMDTLNEEVV | SLYNFERTFQ | LDTAVDRPCA | RSKSTGDPWL |
| 2950 | 2960 | 2970 | 2980 | 2990 | 3000 |
| TDGSYLDGTG | FARISFDSQI | STTKRFEQEL | RLVSYSGVLF | FLKQQSQFLC | LAVQEGSLVL |
| 3010 | 3020 | 3030 | 3040 | 3050 | 3060 |
| LYDFGAGLKK | AVPLQPPPPL | TSASKAIQVF | LLGGSRKRVL | VRVERATVYS | VEQDNDLELA |
| 3070 | 3080 | 3090 | 3100 | 3110 | 3120 |
| DAYYLGGVPP | DQLPPSLRRL | FPTGGSVRGC | VKGIKALGKY | VDLKRLNTTG | VSAGCTADLL |
| 3130 | 3140 | 3150 | 3160 | 3170 | 3180 |
| VGRAMTFHGH | GFLRLALSNV | APLTGNVYSG | FGFHSAQDSA | LLYYRASPDG | LCQVSLQQGR |
| 3190 | 3200 | 3210 | 3220 | 3230 | 3240 |
| VSLQLLRTEV | KTQAGFADGA | PHYVAFYSNA | TGVWLYVDDQ | LQQMKPHRGP | PPELQPQPEG |
| 3250 | 3260 | 3270 | 3280 | 3290 | 3300 |
| PPRLLLGGLP | ESGTIYNFSG | CISNVFVQRL | LGPQRVFDLQ | QNLGSVNVST | GCAPALQAQT |
| 3310 | 3320 |  |  |  |  |
| PGLGPRGLQA | TARKASRRSR | QPA |  |  |  |

TABLE 5 depicting SEQ ID NO: 5, which is the amino acid sequence of the truncated laminin-511 alpha-5 chain that contains the G4 domain, but lacks the G5 domain.
Amino acid sequence of the C-terminal 910 amino acids (Ala2534-Ala3444) of the laminin-511 alpha-5 chain

|  |  |  |  |  |  |
|---|---|---|---|---|---|
| 2530 | 2540 | 2550 | 2560 | 2570 | 2580 |
|  | AAEDAAG | QALQQADHTW | ATVVRQGLVD | RAQQLLANST | ALEEAMLQEQ |
| 2590 | 2600 | 2610 | 2620 | 2630 | 2640 |
| QRLGLVWAAL | QGARTQLRDV | RAKKDQLEAH | IQAAQAMLAM | DTDETSKKIA | HAKAVAAEAQ |
| 2650 | 2660 | 2670 | 2680 | 2690 | 2700 |
| DTATRVQSQL | QAMQENVERW | QGQYEGLRGQ | DLGQAVLDAG | HSVSTLEKTL | PQLLAKLSIL |
| 2710 | 2720 | 2730 | 2740 | 2750 | 2760 |
| ENRGVHNASL | ALSASIGRVR | ELIAQARGAA | SKVKVPMKFN | GRSGVQLRTP | RDLADLAAYT |
| 2770 | 2780 | 2790 | 2800 | 2810 | 2820 |
| ALKFYLQGPE | PEPGQGTEDR | FVMYMGSRQA | TGDYMGVSLR | DKKVHWVYQL | GEAGPAVLSI |
| 2830 | 2840 | 2850 | 2860 | 2870 | 2880 |
| DEDIGEQFAA | VSLDRTLQFG | HMSVTVERQM | IQETKGDTVA | PGAEGLLNLR | PDDFVFYVGG |
| 2890 | 2900 | 2910 | 2920 | 2930 | 2940 |
| YPSTFTPPPL | LRFPGYRGCI | EMDTLNEEVV | SLYNFERTFQ | LDTAVDRPCA | RSKSTGDPWL |
| 2950 | 2960 | 2970 | 2980 | 2990 | 3000 |
| TDGSYLDGTG | FARISFDSQI | STTKRFEQEL | RLVSYSGVLF | FLKQQSQFLC | LAVQEGSLVL |

TABLE 5-continued depicting SEQ ID NO: 5, which is the amino acid sequence of the truncated laminin-511 alpha-5 chain that contains the G4 domain, but lacks the G5 domain.
Amino acid sequence of the C-terminal 910 amino acids (Ala2534-Ala3444) of the laminin-511 alpha-5 chain

```
         3010       3020       3030       3040       3050       3060
    LYDFGAGLKK AVPLQPPPPL TSASKAIQVF LLGGSRFRVL VRVERATVYS VEQDNDLELA 3070       3080       3090       3100       3110       3120
    DAYYLGGVPP DQLPPSLRRL FPTGGSVRGC VKGIKALSKY VDLKRLNTTG VSAGCTADLL 3130       3140       3150       3160       3170       3180
    VGRAMTFHGH GFLRLALSNV APLTGNVYSG FGFHSAQDSA LLYYRASPDG LCQVSLQQGR 3190       3200       3210       3220       3230       3240
    VSLQLLRTEV KTQAGFADGA PHYVAFYSNA TGVWLYVDDQ LQQMKPHRGP PPELQPQPEG 3250       3260       3270       3280       3290       3300
    PPRLLLGGLP ESGTIYNFSG CISNVFVQRL LGPQRVFDLQ QNLGSVNVST GCAPALQAQT 3310       3320       3330       3340       3350       3360
    PGLGPRGLQA TARKASRRSR QPARHPACML PPHLRTTRDS YQFGGSLSSH LEFVGILARH 3370       3380       3390       3400       3410       3420
    RNWPSLSMHV LPRSSRGLLL FTARLRPGSP SLALFLSNGH FVAQMEGLGT RLRAQSRQRS 3430       3440
    RPGRWHKVSV RWEKNRILLV TDGA
```

TABLE 6 depicting SEQ ID NO: 6, which is the amino acid sequence of the full-length laminin-511 alpha-5 chain.
Protein Name = LAMA5_HUMAN Laminin subunit alpha-5
Gene = "LAMA5"
Size = 3695 A.A.
http://www.uniprot.org/uniprot/O15230

MAKRLCAGSALCVRGPRGPAPLLLVGLALLGAARAREEAGGGFSLHPPYFNLAEGARIAA

SATCGEEAPARGSPRPTEDLYCKLVGGPVAGGDPNQTIRGQYCDICTAANSNKAHPASNA

IDGTERWWQSPPLSRGLEYNEVNVTLDLGQVFHVAYVLIKFANSPRPDLWVLERSMDFGR

TYQPWQFFASSKRDCLERFGPQTLERITRDDAAICTTEYSRIVPLENGEIVVSLVNGRPG

AMNFSYSPLLREFTKATNVRLRFLRTNTLLGHLMGKALRDPTVTRRYYYSIKDISIGGRC

VCHGHADACDAKDPTDPFRLQCTCQHNTCGGTCDRCCPGFNQQPWKPATANSANECQSCN

CYGHATDCYYDPEVDRRRASQSLDGTYQGGGVCIDCQHHTTGVNCERCLPGFYRSPNHPL

DSPHVCRRCNCESDFTDGTCEDLTGRCYCRPNFSGERCDVCAEGFTGFPSCYPTPSSSND

TREQVLPAGQIVNCDCSAAGTQGNACRKDPRVGRCLCKPNFQGTHCELCAPGFYGPGCQP

CQCSSPGVADDRCDPDTGQCRCRVGFEGATCDRCAPGYFHFPLCQLCGCSPAGTLPEGCD

EAGRCLCQPEFAGPHCDRCRPGYHGFPNCQACTCDPRGALDQLCGAGGLCRCRPGYTGTA

CQECSPGFHGFPSCVPCHCSAEGSLHAACDPRSGQCSCRPRVTGLRCDTCVPGAYNFPYC

EAGSCHPAGLAPVDPALPEAQVPCMCRAHVEGPSCDRCKPGFWGLSPSNPEGCTRCSCDL

RGTLGGVAECQPGTGQCFCKPHVCGQACASCKDGFFGLDQADYFGCRSCRCDIGGALGQS

CEPRTGVCRCRPNTQGPTCSEPARDHYLPDLHHLRLELEEAATPEGHAVRFGFNPLEFEN

FSWRGYAQMAPVQPRIVARLNLTSPDLFWLVFRYVNRGAMSVSGRVSVREEGRSATCANC

TAQSQPVAFPPSTEPAFITVPQRGFGEPFVLNPGTWALRVEAEGVLLDYVVLLPSAYYEA

ALLQLRVTEACTYRPSAQQSGDNCLLYTHLPLDGFPSAAGLEALCRQDNSLPRPCPTEQL

TABLE 6-continued depicting SEQ ID NO: 6, which is the amino acid
sequence of the full-length laminin-511 alpha-5
chain.
Protein Name = LAMA5_HUMAN Laminin subunit alpha-5
Gene = "LAMA5"
Size = 3695 A.A.
http://www.uniprot.org/uniprot/O15230

SPSHPPLITCTGSDVDVQLQVAVPQPGRYALVVEYANEDARQEVGVAVHTPQRAPQQGLL

SLHPCLYSTLCRGTARDTQDHLAVFHLDSEASVRLTAEQARFFLHGVTLVPIEEFSPEFV

EPRVSCISSHGAFGPNSAACLPSRFPKPPQPIILRDCQVIPLPPGLPLTHAQDLTPAMSP

AGPRPRPPTAVDPDAEPTLLREPQATVVFTTHVPTLGRYAFLLHGYQPAHPTFPVEVLIN

AGRVWQGHANASFCPHGYGCRTLVVCEGQALLDVTHSELTVTVRVPKGRWLWLDYVLVVP

ENVYSFGYLREEPLDKSYDFISHCAAQGYHISPSSSSLFCRNAAASLSLFYNNGARPCGC

HEVGATGPTCEPFGGQCPCHAHVIGRDCSRCATGYWGFPNCRPCDCGARLCDELTGQCIC

PPRTIPPDCLLCQPQTFGCHPLVGCEECNCSGPGIQELTDPTCDTDSGQCKCRPNVTGRR

CDTCSPGFHGYPRCRPCDCHEAGTAPGVCDPLTGQCYCKENVQGPKCDQCSLGTFSLDAA

NPKGCTRCFCFGATERCRSSSYTRQEFVDMEGWVLLSTDRQVVPHERQPGTEMLRADLRH

VPEAVPEAFPELYWQAPPSYLGDRVSSYGGTLRYELHSETQRGDVFVPMESRPDVVLQGN

QMSITFLEPAYPTPGHVHRGQLQLVEGNFRHTETRNTVSREELMMVLASLEQLQIRALFS

QISSAVFLRRVALEVASPAGQGALASNVELCLCPASYRGDSCQECAPGFYRDVKGLFLGR

CVPCQCHGHSDRCLPGSGVCVDCQHNTEGAHCERCQAGFVSSRDDPSAPCVSCPCPLSVP

SNNFAEGCVLRGGRTQCLCKPGYAGASCERCAPGFFGNPLVLGSSCQPCDCSGNGDPNLL

FSDCDPLTGACRGCLRHTTGPRCEICAPGFYGNALLPGNCTRCDCTPCGTEACDPHSGHC

LCKAGVTGRRCDRCQEGHFGFDGCGGCRPCACGPAAEGSECHPQSGQCHCRPGTMGPQCR

ECAPGYWGLPEQGCRRCQCPGGRCDPHTGRCNCPPGLSGERCDTCSQQHQVPVPGGPVGH

SIHCEVCDHCVVLLLDDLERAGALLPAIHEQLRGINASSMAWARLHRLNASIADLQSQLR

SPLGPRHETAQQLEVLEQQSTSLGQDARRLGGQAVGTRDQASQLLAGTEATLGHAKTLLA

AIRAVDRTLSELMSQTGHLGLANASAPSGEQLLRTLAEVERLLWEMRARDLGAPQAAAEA

ELAAAQRLLARVQEQLSSLWEENQALATQTRDRLAQHEAGLMDLREALNRAVDATREAQE

LNSRNQERLEEALQRKQELSRDNATLQATLHAARDTLASVFRLLHSLDQAKEELERLAAS

LDGARTPLLQRMQTFSPAGSKLRLVEAAEAHAQQLGQLALNLSSIILDVNQDRLTQRAIE

ASNAYSRILQAVQAAEDAAGQALQQADHTWATVVRQGLVDRAQQLLANSTALEEAMLQEQ

QRLGLVWAALQGARTQLRDVRAKKDQLEAHIQAAQAMLAMDTDETSKKIAHAKAVAAEAQ

DTATRVQSQLQAMQENVERWQGQYEGLRGQDLGQAVLDAGHSVSTLEKTLPQLLAKLSIL

ENRGVHNASLALSASIGRVRELIAQARGAASKVKVPMKFNGRSGVQLRTPRDLADLAAYT

ALKFYLQGPEPEPGQGTEDRFVMYMGSRQATGDYMGVSLRDKKVHWVYQLGEAGPAVLSI

DEDIGEQFAAVSLDRTLQFGHMSVTVERQMIQETKGDTVAPGAEGLLNLRPDDFVFYVGG

YPSTFTPPPLLRFPGYRGCIEMDTLNEEVVSLYNFERTFQLDTAVDRPCARSKSTGDPWL

TDGSYLDGTGFARISFDSQISTTKRFEQELRLVSYSGVLFFLKQQSQFLCLAVQEGSLVL

LYDFGAGLKKAVPLQPPPPLTSASKAIQVFLLGGSRKRVLVRVERATVYSVEQDNDLELA

DAYYLGGVPPDQLPPSLRRLFPTGGSVRGCVKGIKALGKYVDLKRLNTTGVSAGCTADLL

VGRAMTFHGHGFLRLALSNVAPLTGNVYSGFGFHSAQDSALLYYRASPDGLCQVSLQQGR

VSLQLLRTEVKTQAGFADGAPHYVAFYSNATGVWLYVDDQLQQMKPHRGPPPELQPQPEG

TABLE 6-continued depicting SEQ ID NO: 6, which is the amino acid sequence of the full-length laminin-511 alpha-5 chain.
Protein Name = LAMA5_HUMAN Laminin subunit alpha-5
Gene = "LAMA5"
Size = 3695 A.A.
http://www.uniprot.org/uniprot/O15230

PPRLLLGGLPESGTIYNFSGCISNVFVQRLLGPQRVFDLQQNLGSVNVSTGCAPALQAQT

PGLGPRGLQATARKASRRSRQPARHPACMLPPHLRTTRDSYQFGGSLSSHLEFVGILARH

RNWPSLSMHVLPRSSRGLLLFTARLRPGSPSLALFLSNGHFVAQMEGLGTRLRAQSRQRS

RPGRWHKVSVRWEKNRILLVTDGARAWSQEGPHRQHQGAEHPQPHTLFVGGLPASSHSSK

LPVTVGFSGCVKRLRLHGRPLGAPTRMAGVTPCILGPLEAGLFFPGSGGVITLDLPGATL

PDVGLELEVRPLAVTGLIFHLGQARTPPYLQLQVTEKQVLLRADDGAGEFSTSVTRPSVL

CDGQWHRLAVMKSGNVLRLEVDAQSNHTVGPLLAAAAGAPAPLYLGGLPEPMAVQPWPPA

YCGCMRRLAVNRSPVAMTRSVEVHGAVGASGCPAA

TABLE 7 depicting SEQ ID NO: 7, which is the amino acid sequence of the full-length laminin-511 beta-1 chain
Protein Name = LAMB1_HUMAN Laminin subunit beta-1
Gene = "LAMB1"
Size = 1786 A.A.
http://www.uniprot.org/uniprot/P07942

MGLLQLLAFSFLALCRARVRAQEPEFSYGCAEGSCYPATGDLLIGRAQKLSVTSTCGLHK

PEPYCIVSHLQEDKKCFICNSQDPYHETLNPDSHLIENVVTTFAPNRLKIWWQSENGVEN

VTIQLDLEAEFHFTHLIMTFKTFRPAAMLIERSSDFGKTWGVYRYFAYDCEASFPGISTG

PMKKVDDIICDSRYSDIEPSTEGEVIFRALDPAFKIEDPYSPRIQNLLKITNLRIKFVKL

HTLGDNLLDSRMEIREKYYYAVYDMVVRGNCFCYGHASECAPVDGFNEEVEGMVHGHCMC

RHNTKGLNCELCMDFYHDLPWRPAEGRNSNACKKCNCNEHSISCHFDMAVYLATGNVSGG

VCDDCQHNTMGRNCEQCKPFYYQHPERDIRDPNFCERCTCDPAGSQNEGICDSYTDFSTG

LIAGQCRCKLNVEGEHCDVCKEGFYDLSSEDPFGCKSCACNPLGTIPGGNPCDSETGHCY

CKRLVTGQHCDQCLPEHWGLSNDLDGCRPCDCDLGGALNNSCFAESGQCSCRPHMIGRQC

NEVEPGYYFATLDHYLYEAEEANLGPGVSIVERQYIQDRIPSWTGAGFVRVPEGAYLEFF

IDNIPYSMEYDILIRYEPQLPDHWEKAVITVQRPGRIPTSSRCGNTIPDDDNQVVSLSPG

SRYVVLPRPVCFEKGTNYTVRLELPQYTSSDSDVESPYTLIDSLVLMPYCKSLDIFTVGG

SGDGVVTNSAWETFQRYRCLENSRSVVKTPMTDVCRNIIFSISALLHQTGLACECDPQGS

LSSVCDPNGGQCQCRPNVVGRTCNRCAPGTFGFGPSGCKPCECHLQGSVNAFCNPVTGQC

HCFQGVYARQCDRCLPGHWGFPSCQPCQCNGHADDCDPVTGECLNCQDYTMGHNCERCLA

GYYGDPIIGSGDHCRPCPCPDGPDSGRQFARSCYQDPVTLQLACVCDPGYIGSRCDDCAS

GYFGNPSEVGGSCQPCQCHNNIDTTDPEACDKETGRCLKCLYHTEGEHCQFCRFGYYGDA

LQQDCRKCVCNYLGTVQEHCNGSDCQCDKATGQCLCLPNVIGQNCDRCAPNTWQLASGTG

CDPCNCNAAHSFGPSCNEFTGQCQCMPGFGGRTCSECQELFWGDPDVECRACDCDPRGIE

TPQCDQSTGQCVCVEGVEGPRCDKCTRGYSGVFPDCTPCHQCFALWDVIIAELTNRTHRF

LEKAKALKISGVIGPYRETVDSVERKVSEIKDILAQSPAAEPLKNIGNLFEEAEKLIKDV

TEMMAQVEVKLSDTTSQSNSTAKELDSLQTEAESLDNTVKELAEQLEFIKNSDIRGALDS

TABLE 7-continued depicting SEQ ID NO: 7, which is the amino acid
sequence of the full-length laminin-511 beta-1 chain
Protein Name = LAMB1_HUMAN Laminin subunit beta-1
Gene = "LAMB1"
Size = 1786 A.A.
http://www.uniprot.org/uniprot/P07942

ITKYFQMSLEAEEERVNASTTEPNSTVEQSALMRDRVEDVMMERESQFKEKQEEQARLLDE

LAGKLQSLDLSAAAEMTCGTPPGASCSETECGGPNCRTDEGERKCGGPGCGGLVTVAHNA

WQKAMDLDQDVLSALAEVEQLSKMVSEAKLRADEAKQSAEDILLKTNATKEKMDKSNEEL

RNLIKQIRNFLTQDSADLDSIEAVANEVLKMEMPSTPQQLQNLTEDIRERVESLSQVEVI

LQHSAADIARAEMLLEEAKRASKSATDVKVTADMVKEALEEAEKAQVAAEKAIKQADEDI

QGTQNLLTSIESETAASEETLFNASQRISELERNVEELKRKAAQNSGEAEYIEKVVYTVK

QSAEDVKKTLDGELDEKYKKVENLIAKKTEESADARRKAEMLQNEAKTLLAQANSKLQLL

KDLERKYEDNQRYLEDKAQELARLEGEVRSLLKDISQKVAVYSTCL

TABLE 8 depicting SEQ ID NO: 8, which is the amino acid
sequence of the full-length laminin-511 gamma-1
chain.
Protein Name = LAMC1_HUMAN Laminin subunit gamma-1
Gene = "LAMC1"
Size = 1609 A.A.
http://www.uniprot.org/uniprot/P11047

MRGSHRAAPALRPRGRLWPVLAVLAAAAAGCAQAAMDECTDEGGRPQRCMPEFVNAAFN

VTVVATNTCGTPPEEYCVQTGVTGVTKSCHLCDAGQPHLQHGAAFLTDYNNQADTTWWQS

QTMLAGVQYPSSINLTLHLGKAFDITYVRLKFHTSRPESFAIYKRTREDGPWIPYQYYSG

SCENTYSKANRGFIRTGGDEQQALCTDEFSDISPLTGGNVAFSTLEGRPSAYNFDNSPVL

QEWVTATDIRVTLNRLNTFGDEVFNDPKVLKSYYYAISDFAVGGRCKCNGHASECMKNEF

DKLVCNCKHNTYGVDCEKCLPFFNDRPWRRATAESASECLPCDCNGRSQECYFDPELYRS

TGHGGHCTNCQDNTDGAHCERCRENFFRLGNNEACSSCHCSPVGSLSTQCDSYGRCSCKP

GVMGDKCDRCQPGFHSLTEAGCRPCSCDPSGSIDECNIETGRCVCKDNVEGFNCERCKPG

FFNLESSNPRGCTPCFCFGHSSVCTNAVGYSVYSISSTFQIDEDGWRAEQRDGSEASLEW

SSERQDIAVISDSYFPRYFIAPAKFLGKQVLSYGQNLSFSFRVDRRDTRLSAEDLVLEGA

GLRVSVPLIAQGNSYPSETTVKYVFRLHEATDYPWRPALTPFEFQKLLNNLTSIKIRGTY

SERSAGYLDDVTLASARPGPGVPATWVESCTCPVGYGGQFCEMCLSGYRRETPNLGPYSP

CVLCACNGHSETCDPETGVCNCRDNTAGPHCEKCSDGYYGDSTAGTSSDCQPCPCPGGSS

CAVVPKTKEVVCTNCPTGTTGKRCELCDDGYFGDPLGRNGPVRLCRLCQCSDNIDPNAVG

NCNRLTGECLKCIYNTAGFYCDRCKDGFFGNPLAPNPADKCKACNCNLYGTMKQQSSCNP

VTGQCECLPHVTGQDCGACDPGFYNLQSGQGCERCDCHALGSTNGQCDIRTGQCECQPGI

TGQHCERCEVNHFGFGPEGCKPCDCHPEGSLSLQCKDDGRCECREGFVGNRCDQCEENYF

YNRSWPGCQECPACYRLVKDKVADHRVKLQELESLIANLGTGDEMVTDQAFEDRLKEAER

EVMDLLREAQDVKDVDQNLMDRLQRVNNTLSSQISRLQNIRNTIEETGNLAEQARAHVEN

TERLIEIASRELEKAKVAAANVSVTQPESTGDPNNMTLLAEEARKLAERHKQEADDIVRV

AKTANDTSTEAYNLLLRTLAGENQTAFEIEELNRKYEQAKNISQDLEKQAARVHEEAKRA

GDKAVEIYASVAQLSPLDSETLENEANNIKMEAENLEQLIDQKLKDYEDLREDMRGKELE

TABLE 8-continued depicting SEQ ID NO: 8, which is the amino acid
sequence of the full-length laminin-511 gamma-1
chain.
Protein Name = LAMC1_HUMAN Laminin subunit gamma-1
Gene = "LAMC1"
Size = 1609 A.A.
http://www.uniprot.org/uniprot/P11047

VKNLLEKGKTEQQTADQLLARADAAKALAEEAAKKGRDTLQEANDILNNLKDFDRRVNDN

KTAAEEALRKIPAINQTITEANEKTREAQQALGSAAADATEAKNKAHEAERIASAVQKNA

TSTKAEAERTFAEVTDLDNEVNNMLKQLQEAEKELKRKQDDADQDMMMAGMASQAAQEAE

INARKAKNSVTSLLSIINDLLEQLGQLDTVDLNKLNEIEGTLNKAKDEMKVSDLDRKVSD

LENEAKKQEAAIMDYNRDIEEIMKDIRNLEDIRKTLPSGCFNTPSIEKP

REFERENCES

Aumailley M et al., (2005). A simplified laminin nomenclature. *Matrix Biol* 24: 326-332.
Burkin D J & Kaufman S J (1999). The alpha7beta1 integrin in muscle development and disease. *Cell Tissue Res* 296: 183-190.
De Villez R L (1985). Topical minoxidil therapy in hereditary androgenetic alopecia. *Arch Dermatol* 121:197-202.
Gao J et al. (2008). Laminin-511 is an early epithelial message promoting dermal papilla development and function during early hair morphogenesis. *Genes Dev* 22:2111-2124.
Hardy M H (1992). The secret life of the hair follicle. *Trends Genet.* 8:55-61.
Hendrix S et al. (2005). A guide to assessing damage response pathways of the hair follicle: lessons from cyclophosphamide-induced alopecia in mice. *J Invest Dermatol* 125:42-51.
Hoogenboom H R and Winter G (1992). By-passing immunisation. Human antibodies from synthetic repertoires of germline VH gene segments rearranged in vitro. *J Mol Biol* 227:381-388.
Jakobovits A et al. (1993). Analysis of homozygous mutant chimeric mice: Deletion of the immunoglobulin heavy-chain joining region blocks B-cell development and antibody production. *Proc Natl Acad Sci USA* 90:2551.
Jakobovits A et al. (1993). Germ-line transmission and expression of a human-derived yeast artificial chromosome. *Nature* 362:255-258.
Jakobovits et al. (2007). From XenoMouse technology to panitumumab, the first fully human antibody product from transgenic mice. *Nat Biotech* 25:1134-1143.
Jones P T et al. (1986). Replacing the complementarity-determining regions in a human antibody with those from a mouse. *Nature* 321:522-525.
Koehler G & Milstein C (1975). Continuous cultures of fused cells secreting antibody of predefined specificity. *Nature* 256:495.
Krause K & Foitzik K (2006). Biology of the Hair Follicle: The Basics. *Semin Cutan Med Surg* 25:2-10.
Kyte J & Doolittle R F (1982). A simple method for displaying the hydropathic character of a protein. *J Mol Biol* 157, 105-132.
Leyden J et al. (1999). Finasteride in the treatment of men with frontal male pattern hair loss. *JAAD* 40: 930-937.
Li et al. (2003). Laminin-10 is crucial for hair morphogenesis. *The EMBO Journal* 22:2400-2410.
Marks J D et al (1991). By-passing immunization: human antibodies from V gene libraries displayed on phage. *J Mol Biol* 222:581.
Miner J H & Yurchenco P D (2004). Laminin functions in tissue morphogenesis. *Ann Rev Cell Dev Biol* 20:255-284.
Needleman S B & Wunsch C D (1970). A general method applicable to the search for similarities in the amino acid sequence of two proteins. *J Mol Biol* 48: 443-453.
Oro A E & Scott M P (1998). Splitting hairs: Dissecting roles of signaling systems in epidermal development. *Cell* 95: 575-578.
Paus R & Cotsarelis G (1999). The biology of hair follicles. *N Engl J Med* 341:491-497.
Pearson W R & Lipman D J (1988). Improved tools for biological sequence comparison. *Proc Natl Acad Sci U.S.A.* 85:2444-2448.
Smith T F & Waterman M S (1981). Comparison of biosequences. *Adv Appl Math* 2:482-489.
Taieb M et al. (2012). Hyaluronic acid plus mannitol treatment for improved skin hydration and elasticity. *J Cosmet Dermatol* 11:87-92.
Taniguchi Y et al. (2009). The C-terminal Region of Laminin β Chains Modulates the Integrin Binding Affinities of Laminins *J Biol Chem* 284:7820-7831.
Tzu J et al. (2005). Basement membrane and extracellular matrix molecules in the skin. In J. H. Miner (Ed.), *Extracellular matrix in development and disease. Advances in developmental biology* (pp. 129-151). Elsevier.
Tzu J & Marinkovich M P (2008). Bridging structure with function: structural, regulatory, and developmental role of laminins Intl J Biochem & Cell Biol 40:199-214.
Verhoeyen M et al. (1988). Reshaping human antibodies: Grafting an antilysozyme activity. *Science* 239:1534-1536.

What is claimed is:

1. A biodegradable or biocompatible microneedle device for application of a laminin-511 peptide to a subject, the device comprising an array of hollow microneedles comprising a composition comprising a truncated, recombinant laminin-511 peptide trimer and a pharmaceutically acceptable carrier in a therapeutically effective amount to increase scalp hair growth and to decrease scalp hair loss in a subject.

2. The microneedle device of claim 1, wherein the laminin-511 peptide is a truncated, recombinant laminin-511 peptide trimer comprising an alpha-5 chain comprising a sequence identical to SEQ ID NO: 1; a beta-1 chain comprising a sequence identical to SEQ ID NO: 2; and a gamma-1 chain comprising a sequence identical to SEQ ID NO: 3, and conservative variants thereof.

3. The microneedle device of claim 1, wherein the laminin-511 peptide is a truncated, recombinant laminin-511 peptide trimer comprising an alpha-5 chain comprising a sequence identical to SEQ ID NO: 4; a beta-1 chain comprising a sequence identical to SEQ ID NO: 2; and a gamma-1 chain comprising a sequence identical to SEQ ID NO: 3, and conservative variants thereof.

4. The microneedle device of claim 1, wherein the laminin-511 peptide is a truncated, recombinant laminin-511 peptide trimer comprising an alpha-5 chain comprising a sequence identical to SEQ ID NO: 5; a beta-1 chain comprising a sequence identical to SEQ ID NO: 2; and a gamma-1 chain comprising a sequence identical to SEQ ID NO: 3, and conservative variants thereof.

5. The microneedle device of claim 1, wherein said composition further comprises at least one secondary treatment product.

6. A method for delivering a laminin-511 peptide to dermal layers of a subject's scalp, the method comprising providing a biocompatible or biodegradable device comprising an array of hollow microneedles comprising a composition comprising a laminin-511 peptide and a pharmaceutically acceptable carrier in a therapeutically effective amount to a subject in need thereof to increase scalp hair growth and to decrease scalp hair loss in said subject; whereby said array is suited to be inserted into said subject's scalp with a pressure sufficient to deliver said composition to the dermal layers of said subject's scalp.

7. The method of claim 6, wherein the laminin-511 peptide is a truncated, recombinant laminin-511 peptide trimer comprising an alpha-5 chain comprising a sequence identical to SEQ ID NO: 1; a beta -1 chain comprising a sequence identical to SEQ ID NO: 2; and a gamma-1 chain comprising a sequence identical to SEQ ID NO: 3,and conservative variants thereof.

8. The method of claim 6, wherein the laminin-511 peptide is a truncated, recombinant laminin-511 peptide trimer comprising an alpha-5 chain comprising a sequence identical to SEQ ID NO: 4; a beta-1 chain comprising a sequence identical to SEQ ID NO: 2; and a gamma-1 chain comprising a sequence identical to SEQ ID NO: 3, and conservative variants thereof.

9. The method of claim 6, wherein the laminin-511 peptide is a truncated, recombinant laminin-511 peptide trimer comprising an alpha-5 chain comprising a sequence identical to SEQ ID NO: 5; a beta-1 chain comprising a sequence identical to SEQ ID NO: 2; and a gamma-1 chain comprising a sequence identical to SEQ ID NO: 3, and conservative variants thereof.

10. The method of claim 6, wherein the laminin-511 peptide is a full-length laminin-511 trimer comprising an alpha-5 chain comprising a sequence identical to SEQ ID NO:6; a beta-1 chain comprising a sequence identical to SEQ ID NO:7; and a gamma -1 chain comprising a sequence identical to SEQ ID NO:8, and conservative variants thereof.

11. The method of claim 6, wherein said composition further comprises at least one secondary treatment product.

12. A method for increasing scalp hair growth and decreasing scalp hair loss in a subject, said method comprising providing a biocompatible or biodegradable-device comprising an array of hollow microneedles comprising a composition comprising a laminin-511 peptide and a pharmaceutically acceptable carder in a therapeutically effective amount to a subject in need thereof, whereby said device is inserted into said subject's scalp with a pressure sufficient to deliver said composition to the dermal layers of said subject's scalp.

13. The method of claim 12, wherein the truncated, recombinant laminin-511 peptide comprises an alpha-5 chain comprising a sequence identical to SEQ ID NO: 1; a beta-1 chain comprising a sequence identical to SEQ ID NO: 2; and a gamma-1 chain comprising a sequence identical to SEQ ID NO: 3, and conservative variants thereof.

14. The method of claim 12, wherein the truncated, recombinant laminin-511 peptide comprises an alpha-5 chain comprising a sequence identical to SEQ ID NO: 4; a beta-1 chain comprising a sequence identical to SEQ ID NO: 2; and a gamma-1 chain comprising a sequence identical to SEQ ID NO: 3, and conservative variants thereof.

15. The method of claim 12, wherein the truncated, recombinant laminin-511 peptide comprises an alpha-5 chain comprising a sequence identical to SEQ ID NO: 5; a beta-1 chain comprising a sequence identical to SEQ ID NO: 2; and a gamma-1 chain comprising a sequence identical to SEQ ID NO: 3, and conservative variants thereof.

16. The method of claim 12, wherein the composition comprises at least one secondary treatment product.

17. A kit for carrying out a procedure to increase scalp hair growth and to decrease scalp hair loss, the kit comprising one or more biodegradable or biocompatible microneedle device for application of a laminin-511 peptide to a subject, said device comprising an array of hollow microneedles comprising a composition comprising a truncated, recombinant laminin-511 peptide trimer and a pharmaceutically acceptable carrier in a therapeutically effective amount to increase scalp hair growth and to decrease scalp hair loss in a subject, and directions for use.

18. The kit of claim 17, wherein the truncated, recombinant laminin-511 peptide comprises an alpha-5 chain comprising a sequence identical to SEQ ID NO: 1; a beta-1 chain comprising a identical to SEQ ID NO: 2; and a gamma-1 chain comprising a sequence identical to SEQ ID NO: 3, and conservative variants thereof.

19. The kit of claim 17, wherein the truncated, recombinant laminin-511 peptide comprises an alpha-5 chain comprising a sequence identical to SEQ ID NO:4; a beta-1 chain comprising a sequence identical to SEQ ID NO:2; and a gamma-1 chain comprising a sequence identical to SEQ ID NO:3, and conservative variants thereof.

20. The kit of claim 17, wherein the truncated, recombinant laminin-511 peptide comprises an alpha-5 chain comprising a sequence identical to SEQ ID NO:5; a beta-1 chain comprising a sequence identical to SEQ ID NO:2; and a gamma-chain comprising a sequence identical to SEQ ID NO:3, and conservative variants thereof.

21. The kit of claim 17, wherein said one or more microneedle devises further comprising at least one secondary treatment product.

* * * * *